(12) United States Patent
Venkatraman et al.

(10) Patent No.: US 8,945,017 B2
(45) Date of Patent: Feb. 3, 2015

(54) WEARABLE HEART RATE MONITOR

(71) Applicant: Fitbit, Inc., San Francisco, CA (US)

(72) Inventors: Subramaniam Venkatraman, Walnut Creek, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/295,122

(22) Filed: Jun. 3, 2014

(65) Prior Publication Data

US 2014/0288438 A1    Sep. 25, 2014

Related U.S. Application Data

(63) Continuation of application No. 14/292,673, filed on May 30, 2014, which is a continuation-in-part of application No. 13/924,784, filed on Jun. 24, 2013.

(60) Provisional application No. 61/662,961, filed on Jun. 22, 2012, provisional application No. 61/752,826, filed on Jan. 15, 2013, provisional application No. 61/946,439, filed on Feb. 28, 2014, provisional application No. 61/955,045, filed on Mar. 18, 2014, provisional application No. 61/973,614, filed on Apr. 1, 2014, provisional application No. 61/830,600, filed on Jun. 3, 2013, provisional application No. 62/001,624, filed on May 21, 2014, provisional application No. 62/001,585, filed on May 21, 2014.

(51) Int. Cl.
| | |
|---|---|
| *A61B 5/02* | (2006.01) |
| *A61B 5/024* | (2006.01) |
| *A61B 5/00* | (2006.01) |
| *A61B 5/0205* | (2006.01) |
| *A61B 5/11* | (2006.01) |
| *A61B 5/0402* | (2006.01) |
| *A61B 5/0245* | (2006.01) |

(52) U.S. Cl.
CPC .............. *A61B 5/02405* (2013.01); *A61B 5/721* (2013.01); *A61B 5/0205* (2013.01); *A61B 5/1118* (2013.01); *A61B 5/681* (2013.01); *A61B 5/742* (2013.01); *A61B 5/1123* (2013.01); *A61B 5/0402* (2013.01); *A61B 5/02416* (2013.01); *A61B 5/0245* (2013.01)
USPC .......................................... 600/500; 600/503

(58) Field of Classification Search
USPC .................................. 600/300, 301, 500, 503
See application file for complete search history.

(56) References Cited

U.S. PATENT DOCUMENTS

| | | |
|---|---|---|
| 4,367,752 A | 1/1983 | Jimenez et al. |
| 4,771,792 A | 9/1988 | Seale |

(Continued)

FOREIGN PATENT DOCUMENTS

EP    1 721 237    8/2012

OTHER PUBLICATIONS

U.S. Appl. No. 14/214,655, filed Mar. 14, 2014, Hong et al.

(Continued)

*Primary Examiner* — Michael D'Angelo
(74) *Attorney, Agent, or Firm* — Weaver Austin Villeneuve & Sampson LLP

(57) ABSTRACT

A biometric monitoring device is used to determine a user's heart rate by using a heartbeat waveform sensor and a motion detecting sensor. In some embodiments, the device collects collecting concurrent output data from the heartbeat waveform sensor and output data from the motion detecting sensor, detects a periodic component of the output data from the motion detecting sensor, and uses the periodic component of the output data from the motion detecting sensor to remove a corresponding periodic component from the output data from the heartbeat waveform sensor. From this result, the device may determine and present the user's heart rate.

30 Claims, 29 Drawing Sheets

(56) References Cited

U.S. PATENT DOCUMENTS

| | | | |
|---|---|---|---|
| 5,036,856 A | 8/1991 | Thornton | |
| 5,101,831 A | 4/1992 | Koyama et al. | |
| 5,318,597 A | 6/1994 | Hauck et al. | |
| 5,738,104 A | 4/1998 | Lo et al. | |
| 6,131,076 A | 10/2000 | Stephan et al. | |
| 6,241,684 B1 | 6/2001 | Amano et al. | |
| 6,418,394 B1* | 7/2002 | Puolakanaho et al. | 702/139 |
| 6,583,369 B2 | 6/2003 | Montagnino et al. | |
| 6,731,967 B1 | 5/2004 | Turcott | |
| 7,539,532 B2 | 5/2009 | Tran | |
| 8,152,745 B2 | 4/2012 | Smith et al. | |
| 8,211,503 B2* | 7/2012 | Tsao et al. | 427/347 |
| 8,346,328 B2 | 1/2013 | Mannheimer et al. | |
| 8,386,042 B2 | 2/2013 | Yudovsky et al. | |
| 8,444,578 B2 | 5/2013 | Bourget et al. | |
| 8,475,367 B1 | 7/2013 | Yuen et al. | |
| 8,579,827 B1* | 11/2013 | Rulkov et al. | 600/503 |
| 8,792,981 B2 | 7/2014 | Yudovsky et al. | |
| 2004/0236227 A1 | 11/2004 | Gueissaz | |
| 2005/0054940 A1 | 3/2005 | Almen | |
| 2005/0245793 A1 | 11/2005 | Hilton et al. | |
| 2008/0097221 A1 | 4/2008 | Florian | |
| 2009/0012433 A1 | 1/2009 | Fernstrom et al. | |
| 2010/0106044 A1 | 4/2010 | Linderman | |
| 2010/0152600 A1 | 6/2010 | Droitcour et al. | |
| 2010/0249633 A1 | 9/2010 | Droitcour et al. | |
| 2010/0292568 A1 | 11/2010 | Droitcour et al. | |
| 2010/0298650 A1 | 11/2010 | Moon et al. | |
| 2010/0298651 A1 | 11/2010 | Moon et al. | |
| 2010/0298653 A1 | 11/2010 | McCombie et al. | |
| 2010/0331145 A1 | 12/2010 | Lakovic et al. | |
| 2010/0331657 A1 | 12/2010 | Mensinger et al. | |
| 2011/0009727 A1 | 1/2011 | Mensinger et al. | |
| 2011/0032105 A1 | 2/2011 | Hoffman et al. | |
| 2011/0066010 A1 | 3/2011 | Moon et al. | |
| 2012/0083705 A1 | 4/2012 | Yuen et al. | |
| 2012/0083714 A1 | 4/2012 | Yuen et al. | |
| 2012/0083715 A1 | 4/2012 | Yuen et al. | |
| 2012/0083716 A1 | 4/2012 | Yuen et al. | |
| 2012/0084053 A1 | 4/2012 | Yuen et al. | |
| 2012/0084054 A1 | 4/2012 | Yuen et al. | |
| 2012/0123232 A1 | 5/2012 | Najarian et al. | |
| 2012/0150074 A1 | 6/2012 | Yanev et al. | |
| 2012/0172733 A1 | 7/2012 | Park | |
| 2012/0226471 A1 | 9/2012 | Yuen et al. | |
| 2012/0226472 A1 | 9/2012 | Yuen et al. | |
| 2012/0232432 A1 | 9/2012 | Kahn et al. | |
| 2012/0245439 A1 | 9/2012 | Andre et al. | |
| 2012/0255875 A1* | 10/2012 | Vicente et al. | 205/782 |
| 2012/0274508 A1 | 11/2012 | Brown et al. | |
| 2012/0316471 A1 | 12/2012 | Rahman et al. | |
| 2013/0009779 A1 | 1/2013 | Wittling et al. | |
| 2013/0073254 A1 | 3/2013 | Yuen et al. | |
| 2013/0073255 A1 | 3/2013 | Yuen et al. | |
| 2013/0077826 A1 | 3/2013 | Cowperthwaite et al. | |
| 2013/0080113 A1 | 3/2013 | Yuen et al. | |
| 2013/0106684 A1 | 5/2013 | Weast et al. | |
| 2013/0151196 A1 | 6/2013 | Yuen et al. | |
| 2013/0158369 A1 | 6/2013 | Yuen et al. | |
| 2014/0073486 A1* | 3/2014 | Ahmed et al. | 482/9 |
| 2014/0107493 A1 | 4/2014 | Yuen et al. | |
| 2014/0135631 A1 | 5/2014 | Brumback et al. | |
| 2014/0142403 A1 | 5/2014 | Brumback et al. | |
| 2014/0275821 A1 | 9/2014 | Beckman | |
| 2014/0275852 A1 | 9/2014 | Hong et al. | |
| 2014/0275854 A1 | 9/2014 | Venkatraman et al. | |
| 2014/0276119 A1 | 9/2014 | Venkatraman et al. | |
| 2014/0278139 A1 | 9/2014 | Hong et al. | |
| 2014/0288390 A1 | 9/2014 | Hong et al. | |
| 2014/0288391 A1 | 9/2014 | Hong et al. | |
| 2014/0288392 A1 | 9/2014 | Hong et al. | |
| 2014/0288435 A1 | 9/2014 | Richards et al. | |
| 2014/0288436 A1 | 9/2014 | Venkatraman et al. | |
| 2014/0303523 A1 | 10/2014 | Hong et al. | |

OTHER PUBLICATIONS

U.S. Appl. No. 14/481,020, filed Sep. 9, 2014, Hong et al.
U.S. Appl. No. 14/481,762, filed Sep. 9, 2014, Hong et al.
U.S. Appl. No. 14/484,104, filed Sep. 11, 2014, Brumback et al.
U.S. Appl. No. 14/507,173, filed Oct. 6, 2014, Hong et al.
U.S. Appl. No. 14/507,184, filed Oct. 6, 2014, Hong et al.
US Office Action, dated Aug. 4, 2014, issued in U.S. Appl. No. 13/924,784.
US Office Action, dated Oct. 22, 2014, issued in U.S. Appl. No. 14/290,884.
US Notice of Allowance, dated Sep. 23, 2014, issued in U.S. Appl. No. 14/292,669.
US Notice of Allowance (Corrected Notice of Allowability), dated Oct. 14, 2014, issued in U.S. Appl. No. 14/292,669.
US Notice of Allowance, dated Oct. 14, 2014, issued in U.S. Appl. No. 14/295,144.
US Notice of Allowance, dated Sep. 26, 2014, issued in U.S. Appl. No. 14/295,158.
US Office Action, dated Aug. 5, 2014, issued in U.S. Appl. No. 14/292,673.
US Office Action, dated Sep. 18, 2014, issued in U.S. Appl. No. 14/295,059.
US Office Action, dated Mar. 14, 2014, issued in U.S. Appl. No. 14/154,009.
US Office Action, dated Sep. 29, 2014, issued in U.S. Appl. No. 14/154,009.
US Office Action, dated Aug. 22, 2014, issued in U.S. Appl. No. 14/250,256.
US Office Action, dated Oct. 7, 2014, issued in U.S. Appl. No. 14/481,762.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior.html], 10 pp.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
Cooper, Daniel (Aug. 16, 2013) *Withings Pulse review*, http://www.engadget.com/2013/08/16/withings-pulse-revew/, 8 pages.
DesMarais, Christina (posted on Sep. 3, 2013) "Which New Activity Tracker is Best for You?" *Health and Home, Health & Fitness*, *Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch With Wireless Sync," (Mar. 2009), Garmin Ltd., 56 pp.
Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.

(56) References Cited

OTHER PUBLICATIONS

Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Larklife, User Manual, (2012) *Lark Technologies*, 7 pp.
Lark/Larkpro, User Manual, (2012) "What's in the box," *Lark Technologies*, 7 pp.
LIFETRNR, User Manual (2003, specific date unknown), NB new balance®, Implus Footcare, LLC, 3 pages.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N. D. User Manual, Polar® Listen to Your Body, *Manufactured by Polar Electro Oy*, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Rainmaker, (Jul. 25, 2013) "Basis $B_1$ Watch In-Depth Review," [retrieved on Feb. 4, 2014 at http://www.dcrainmaker.com/2013/07/basis-b1-review.html], 56 pp.
"Withings pulse, Quick Installation Guide" (Jul. 24, 2013) Withings Pulse QIG, v 1.3, withings.com/pulse, 16 pages.
Zijlstra, Wiebren, (2004) "Assessment of spatio-temporal parameters during unconstrained walking," *Eur J Appl Physiol*, 92:39-44.
US Notice of Allowance, dated Nov. 19, 2014, issued in U.S. Appl. No. 13/924,784.
US Notice of Allowance, dated Dec. 3, 2014, issued in U.S. Appl. No. 14/295,144.
US Notice of Allowance, dated Dec. 8, 2014, issued in U.S. Appl. No. 14/292,673.
US Office Action, dated Nov. 25, 2014, issued in U.S. Appl. No. 14/154,019.
US Office Action, dated Dec. 4, 2014, issued in U.S. Appl. No. 14/216,743.
US Final Office Action, dated Nov. 21, 2014, issued in U.S. Appl. No. 14/250,256.

* cited by examiner

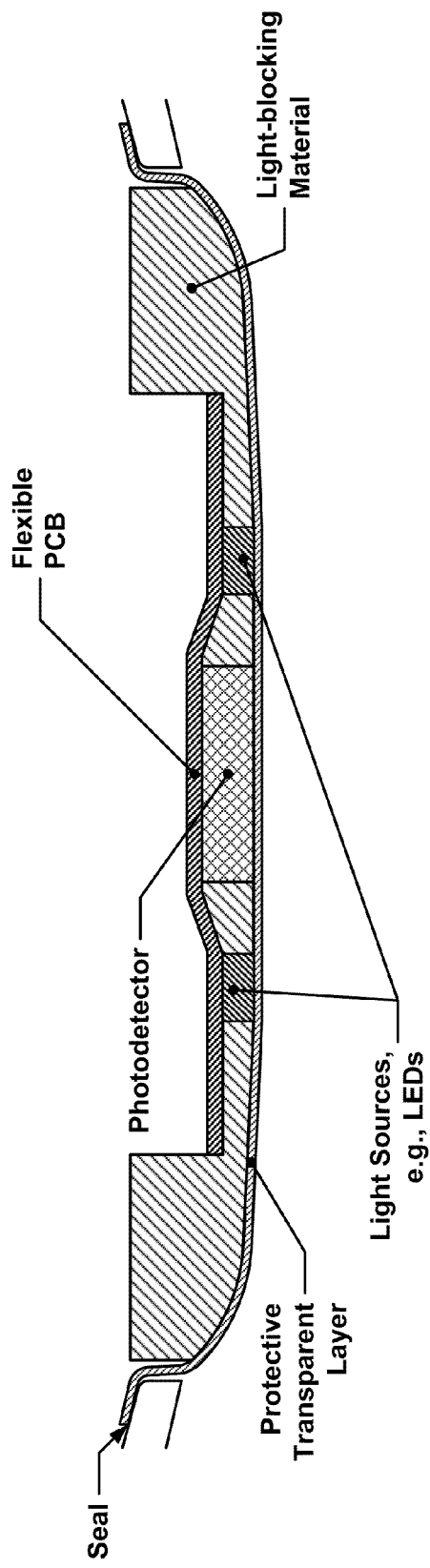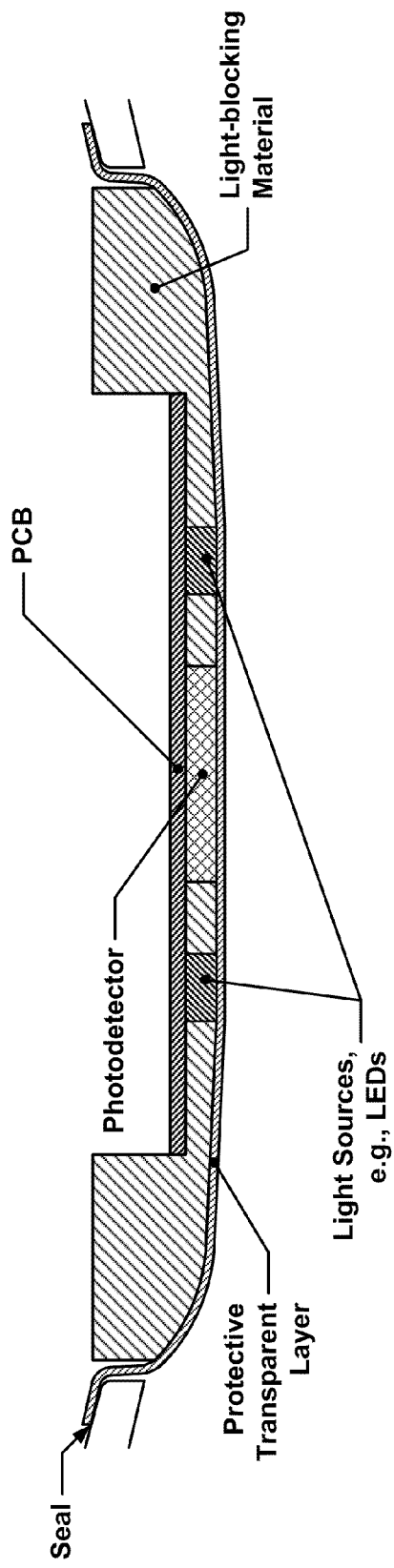
Figure 3A
Figure 3B

Band-Mounted Optical Sensors and Light Emitters

Display

Wristband

Side-Mounted Optical Heart Rate Detection Sensors and/or Emitters

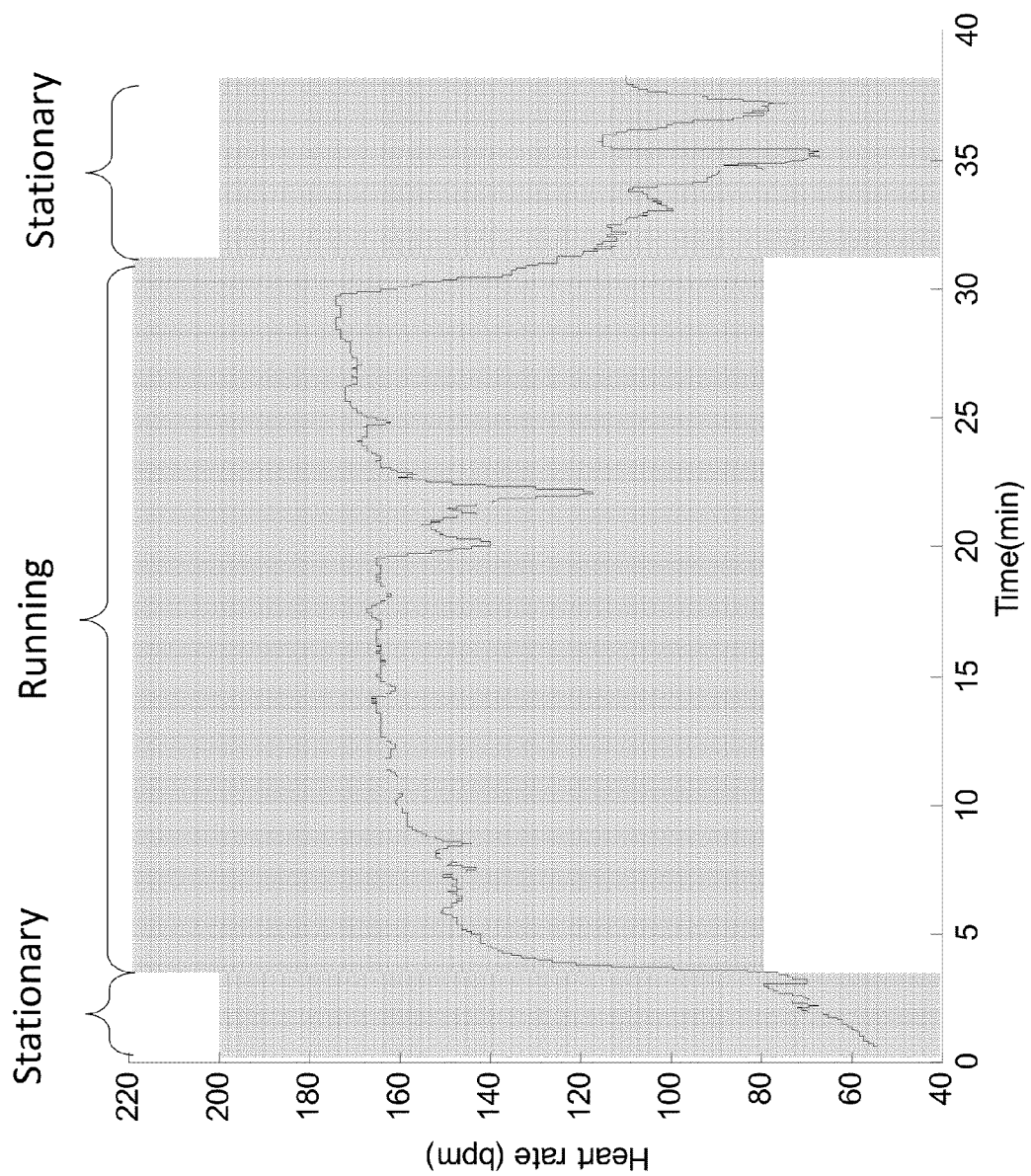

WEARABLE HEART RATE MONITOR

CROSS REFERENCE TO RELATED APPLICATIONS

This application is a continuation of U.S. patent application Ser. No. 14/292,673, titled "WEARABLE HEART RATE MONITOR" and filed on May 30, 2014, which is a continuation-in-part of U.S. patent application Ser. No. 13/924,784, titled "PORTABLE BIOMETRIC MONITORING DEVICES AND METHODS OF OPERATING SAME" and filed on Jun. 24, 2013, which claims benefit of priority under 35 U.S.C. §119(e) to U.S. Provisional Patent Application Nos. 61/662,961, titled "WIRELESS PERSONAL BIOMETRICS MONITOR" and filed on Jun. 22, 2012 and 61/752,826, titled "PORTABLE MONITORING DEVICES AND METHODS OF OPERATING SAME" and filed on Jan. 15, 2013; this application also claims benefit of priority under 35 U.S.C. §119(e) to U.S. Provisional Patent Application Nos. 61/830,600, titled "PORTABLE MONITORING DEVICES AND METHODS OF OPERATING SAME" and filed on Jun. 3, 2013, 61/946,439, titled "HEART RATE DATA COLLECTION" and filed on Feb. 28, 2014, 61/955,045, titled "GPS POWER CONSERVATION USING ENVIRONMENTAL DATA" and filed on Mar. 18, 2014, 61/973,614, titled "GPS ACCURACY REFINEMENT USING EXTERNAL SENSORS" and filed on Apr. 1, 2014, 62/001,624, titled "FITNESS MONITORING DEVICE WITH ALTIMETER" and filed on May 21, 2014, and 62/001,585, titled "WEARABLE HEART RATE MONITOR" and filed on May 21, 2014, all of which are hereby incorporated by reference herein in their entireties.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be offered in extremely small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

The disclosure provides methods and devices for activating, in energy efficient ways, HR monitor based on user motion and skin proximity. The disclosure also provides methods for operating the LED and photo detector of heart rate monitors to obtain accurate reading of heart rate tailored for different user characteristics such as skin colors.

SUMMARY

One aspect of the disclosure provides methods of determining a user's heart rate when wearing a biometric monitoring device having a plurality of sensors including a heartbeat waveform sensor and a motion detecting sensor. The methods may remove motion artifacts from heartbeat waveform signals when determining a user's heart rate. The methods may be characterized by the following operations: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) using the periodic component of the output data from the motion detecting sensor to remove a corresponding periodic component from the output data from the heartbeat waveform sensor; (d) determining the user's heart rate; and (e) presenting the user's heart rate. In some implementations, the motion detecting sensor is an accelerometer or a gyroscope. In some embodiments, the heartbeat waveform sensor may be a photoplethysmography sensor or an ECG sensor.

In certain embodiments, the method contains an additional operation of removing a harmonic of the corresponding periodic component from the output data from the heartbeat waveform sensor. In such embodiments, the periodic component of the output data from the motion detecting sensor may be a fundamental frequency produced from the user's periodic movement. In certain embodiments, the operation removing a corresponding periodic component from the output data from the heartbeat waveform sensor includes applying an adaptive filter to the output data from the heartbeat waveform sensor and the output data from the motion detecting sensor. In certain embodiments, removing a corresponding periodic component from the output data from the heartbeat waveform sensor includes the operation applying an adaptive filter function to the output data from the motion detecting sensor that minimizes the difference between the output data from the heartbeat waveform sensor and the output data from the motion detecting sensor.

In some implementations, the method includes the following additional operations: (i) determining the user's activity level and/or activity type; and (ii) determining parameters of the function based on the user's activity level and/or activity type.

In some implementations, the method includes the following additional operations: (i) analyzing the output data from the motion detecting sensor to infer that the user is substantially stationary; and (ii) temporarily suspending operation (c).

In some method implementations, the operation collecting the output data from the heartbeat waveform sensor includes the following operations: (i) pulsing a light source in the worn biometric monitoring device at a first frequency; and (ii) detecting light from the light source at the first frequency. Pulsing the light source at the first frequency may involve emitting a succession of light pulses of substantially constant intensity.

In certain embodiments, presenting the user's heart rate includes presenting the heart rate on the worn biometric monitoring device. In certain embodiments, presenting the user's heart rate includes presenting the heart rate on an external device that periodically communicates with the worn biometric monitoring device.

Another aspect of the invention pertains to wearable fitness monitoring devices designed or configured to remove motion artifacts from heartbeat waveform signals when determining a user's heart rate. Such devices may be characterized by the following features: a motion sensor configured to provide output corresponding to motion by a user wearing the fitness monitoring device; a heartbeat waveform sensor; and control logic. The control logic includes instructions for: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) using the periodic component of the output data from the motion detecting sensor to remove a corresponding periodic component from the output data from the heartbeat waveform sensor; (d) determining the user's heart rate; and (e) presenting the user's heart rate.

The control logic is typically, though not necessarily, located on the fitness monitoring device. It may be implemented as hardware, software, firmware, or any combination thereof. The data used by the control logic in executing the instructions described herein may be stored (e.g., buffered) by associated memory, registers, and the like, which may be entirely resident on the device or partially resident on a paired secondary device. Examples of suitable architectures for implementing the control logic are presented below with reference to, e.g., FIGS. 11A-G, 12A-C, 13A-B, and 14A-D.

In some devices, the motion detecting sensor is an accelerometer or a gyroscope. In certain embodiments, the device's heartbeat waveform sensor is a photoplethysmographic sensor having (i) a periodic light source, (ii) a photo detector positioned to receive periodic light emitted by the light source after interacting with the user's skin, and (iii) circuitry determining the user's heart rate from output of the photo detector. In some implementations, the photoplethysmographic sensor includes two periodic light sources straddling the photo detector. In some implementations, the photoplethysmographic sensor additionally includes a housing having a recess in which the photo detector is disposed. The housing of the photoplethysmographic sensor may have a second recess in which the periodic light source is disposed. In some designs, the housing protrudes at least about 1 mm above a base surface of the wearable fitness monitoring device arranged to press against the user's skin when worn. Further, the photoplethysmographic sensor further may include a spring configured to resist compression when the protruding housing presses against the user's skin. In certain embodiments, the photoplethysmographic sensor also includes an IML film over the photo detector and the periodic light source. In certain embodiments, the periodic light source is an LED.

In some embodiments, the device's control logic includes instructions for removing a harmonic of the corresponding periodic component from the output data from the heartbeat waveform sensor; in such cases the periodic component of the output data from the motion detecting sensor may be a fundamental frequency produced from the user's periodic movement.

In some implementations, the instructions for removing a corresponding periodic component from the output data from the heartbeat waveform sensor include instructions for applying an adaptive filter to the output data from the heartbeat waveform sensor and the output data from the motion detecting sensor. In some implementations, the instructions for removing a corresponding periodic component from the output data from the heartbeat waveform sensor include instructions for applying an adaptive filter function to the output data from the motion detecting sensor that minimizes the difference between the output data from the heartbeat waveform sensor and the output data from the motion detecting sensor.

In certain embodiments, the device's control logic additionally includes instructions for: (i) determining the user's activity level and/or activity type; and (ii) determining parameters of the function based on the user's activity level and/or activity type. In certain embodiments, the control logic further comprises instructions for: (i) analyzing the output data from the motion detecting sensor to infer that the user is substantially stationary; and (ii) temporarily suspending execution of the instructions of (c).

In some implementations, the instructions for collecting the output data from the heartbeat waveform sensor include instructions for: (i) pulsing a light source in the worn biometric monitoring device at a first frequency; and (ii) detecting light from the light source at the first frequency. The instructions for pulsing the light source at the first frequency may include instructions for emitting a succession of light pulses of substantially constant intensity.

In some cases, the instructions for presenting the user's heart rate include instructions for presenting the heart rate on the worn biometric monitoring device. In some cases, the instructions for presenting the user's heart rate include instructions for presenting the heart rate on an external device that periodically communicates with the worn biometric monitoring device.

Another aspect of this disclosure concerns methods of determining a user's heart rate when wearing a worn biometric monitoring device including a plurality of sensors including a heartbeat waveform sensor and a motion detecting sensor. The methods involve a pre-processing operation prior to motion compensation. The methods may be characterized by the following operations: (a) collecting concurrent output data from the heartbeat waveform sensor and output data from the motion detecting sensor, wherein the output data from the heart beat waveform sensor provides information about the user's heart rate and wherein the output data from the motion detecting sensor provides information about the user's periodic physical movements other than heartbeats; (b) determining a periodic component of the output data from the motion detecting sensor; (c) filtering the output data from the heartbeat waveform sensor to remove variations that are slow with respect to an expected heart rate, wherein the filtering produces high pass filtered output data from the heartbeat waveform sensor; (d) determining the user's heart rate; and (e) presenting the user's heart rate. In various implementations, the methods include using the periodic component of the output data from the motion detecting sensor to remove a corresponding periodic component from the high pass filtered output data from the heartbeat waveform sensor. The filtering may remove a frequency less than about 0.6 Hz (or less than about 0.3 Hz) from the output data from the heartbeat waveform sensor.

In some implementations, the motion detecting sensor is an accelerometer or a gyroscope. The heartbeat waveform sensor may be a photoplethysmography sensor or an ECG sensor.

In certain embodiments, methods include an additional operation of determining the expected heart rate, and from the expected heart rate, setting a high pass frequency for the filtering.

In some cases, determining the expected heart rate includes analyzing the output data from the motion detecting sensor, which may involve inferring a user activity level and/or detecting an intensity of user activity or a type of user activity. As an example, detecting the type of user activity may be detecting running, walking, standing, sitting, or lying down. As a further example, detecting the intensity of user activity may be detecting running or walking.

In some cases, the periodic movement detected by the motion sensor is a wearer's limb movements, which may be, e.g., steps, swim strokes, ankle revolutions while bicycling, and leg movements on cardio machines.

In some method implementations, the operation of collecting the output data from the heartbeat waveform sensor includes the following operations: (i) pulsing a light source in the worn biometric monitoring device at a first frequency; and (ii) detecting light from the light source at the first frequency. Pulsing the light source at the first frequency may involve emitting a succession of light pulses of substantially constant intensity.

In certain embodiments, presenting the user's heart rate includes presenting the heart rate on the worn biometric monitoring device. In certain embodiments, presenting the user's heart rate includes presenting the heart rate on an external device that periodically communicates with the worn biometric monitoring device.

In some implementations, a method additional includes the operation for determining the user's resting heart rate, and in such cases, the filtering removes a frequency less than about the frequency of the user's heart rate. In some cases, determining the user's resting heart rate involves measuring the user's heart rate soon after they wake up and are while still stationary in bed. In some cases, determining the user's resting heart rate involves measuring the user's average heart rate of the user while the user is sleeping. In some cases, determining the user's resting heart rate involves making multiple measurements of the user's heart rate when the user is awake and stationary.

Another aspect of the invention pertains to wearable fitness monitoring devices designed or configured to pre-process heartbeat waveform signals when determining a user's heart rate. The wearable fitness monitoring devices may be characterized by the following features: a motion sensor configured to provide output corresponding to motion by a user wearing the fitness monitoring device; a heartbeat waveform sensor; and control logic containing instructions for: (a) collecting concurrent output data from the heartbeat waveform sensor and output data from the motion detecting sensor, wherein the output data from the heart beat waveform sensor provides information about the user's heart rate and wherein the output data from the motion detecting sensor provides information about the user's periodic physical movements other than heartbeats; (b) determining a periodic component of the output data from the motion detecting sensor; (c) filtering the output data from the heartbeat waveform sensor to remove variations that are slow with respect to an expected heart rate, wherein the filtering produces high pass filtered output data from the heartbeat waveform sensor; (d) determining the user's heart rate; and (e) presenting the user's heart rate.

The control logic is typically, though not necessarily, located on the fitness monitoring device. It may be implemented as hardware, software, firmware, or any combination thereof. The data used by the control logic in executing the instructions described herein may be stored (e.g., buffered) by associated memory, registers, and the like, which may be entirely resident on the device or partially resident on a paired secondary device. Examples of suitable architectures for implementing the control logic are presented below with reference to, e.g., FIGS. 11A-G, 12A-C, 13A-B, and 14A-D.

In some devices, the motion detecting sensor is an accelerometer or a gyroscope. In certain embodiments, the device's heartbeat waveform sensor is a photoplethysmographic sensor having (i) a periodic light source, (ii) a photo detector positioned to receive periodic light emitted by the light source after interacting with the user's skin, and (iii) circuitry determining the user's heart rate from output of the photo detector. In some implementations, the photoplethysmographic sensor includes two periodic light sources straddling the photo detector. In some implementations, the photoplethysmographic sensor additionally includes a housing having a recess in which the photo detector is disposed. The housing of the photoplethysmographic sensor may have a second recess in which the periodic light source is disposed. In some designs, the housing protrudes at least about 1 mm above a base surface of the wearable fitness monitoring device arranged to press against the user's skin when worn. Further, the photoplethysmographic sensor further may include a spring configured to resist compression when the protruding housing presses against the user's skin. In certain embodiments, the photoplethysmographic sensor also includes an IML film over the photo detector and the periodic light source. In certain embodiments, the periodic light source is an LED.

In certain embodiments, the control logic includes instructions for using the periodic component of the output data from the motion detecting sensor to remove a corresponding periodic component from the high pass filtered output data from the heartbeat waveform sensor. In certain embodiments, the instructions for filtering include instructions for removing a frequency less than about 0.6 Hz (or less than about 0.3 Hz) from the output data from the heartbeat waveform sensor.

In certain embodiments, the control logic additionally includes instructions for determining the expected heart rate, and from the expected heart rate, setting a high pass frequency for the filtering.

In some cases, the instructions for determining the expected heart rate include instructions for analyzing the output data from the motion detecting sensor. Further, the instructions for analyzing the output data from the motion detecting sensor may include instructions for inferring a user activity level. Additionally, the instructions for analyzing the output data from the motion detection sensor may include instructions for detecting an intensity of user activity or a type of user activity. In some cases, the instructions for detecting the type of user activity include instructions for detecting running, walking, standing, sitting, or lying down. In some cases, the instructions for detecting the intensity of user activity include instructions for detecting running or walking. In some implementations, the periodic movement to be detected by the motion sensor is a wearer's limb movements.

In some implementations, the instructions for collecting the output data from the heartbeat waveform sensor include instructions for: (i) pulsing a light source in the worn biometric monitoring device at a first frequency; and (ii) detecting light from the light source at the first frequency. The instructions for pulsing the light source at the first frequency may include instructions for emitting a succession of light pulses of substantially constant intensity.

In some cases, the instructions for presenting the user's heart rate include instructions for presenting the heart rate on the worn biometric monitoring device. In some cases, the instructions for presenting the user's heart rate include instructions for presenting the heart rate on an external device that periodically communicates with the worn biometric monitoring device.

In certain embodiments, the control logic additionally includes instructions for determining the user's resting heart rate, and the instructions for filtering include instructions for removing a frequency less than about the frequency of the user's heart rate.

The instructions for determining the user's resting heart rate may include instructions for (i) measuring the user's heart rate soon after they wake up and are while still stationary in bed, (ii) measuring the user's average heart rate of the user while the user is sleeping, and/or (iii) making multiple measurements of the user's heart rate when the user is awake and stationary.

Another aspect of the disclosure provides methods of determining a user's heart rate when wearing a biometric monitoring device having a plurality of sensors including a heartbeat waveform sensor and a motion detecting sensor. The methods determine heart rate within an expected range. The methods may be characterized by the following operations: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) processing the output data from the heartbeat waveform sensor to remove the periodic component from the output data from the heartbeat waveform sensor; (d) using the output data from the motion detecting sensor, determining a range of expected heart rates; (e) determining the user's heart rate from the output data produced in (c), wherein the determined heart rate exists within the range of expected heart rates; and (f) presenting the user's heart rate. In some implementations, the motion detecting sensor is an accelerometer or a gyroscope. In some embodiments, the heartbeat waveform sensor may be a photoplethysmography sensor or an ECG sensor.

In various embodiments, the operation of determining the range of expected heart rates includes the following operations: (i) determining the user's heart rate when the output data from the motion detecting sensor indicates that the user is substantially stationary; (ii) determining the user's activity level and/or activity type from the periodic component of the output data from the motion detecting sensor; and (iii) determining the range of expected heart rates from the user's heart rate determined in (i) and the user's activity level and/or activity type determined in (ii). In some implementations, a minimum expected heart rate in the range of expected heart rates is greater than the user's heart rate determined in (i). In some implementations, the operation of determining the user's activity type includes inferring the activity type from information contained in the output data from the motion detecting sensor or detecting a manually entered selection of activity type. In certain embodiments, determining the range of expected heart rates includes determining the user's step rate from the output data from the motion detecting sensor.

In some cases, the operation of determining the user's heart rate involves calculating the spectral density of the output data produced in (c).

In some cases, the periodic movement detected by the motion sensor is a wearer's limb movements, which may be, e.g., steps, swim strokes, ankle revolutions while bicycling, and leg movements on cardio machines.

In some method implementations, the operation collecting the output data from the heartbeat waveform sensor includes the following operations: (i) pulsing a light source in the worn biometric monitoring device at a first frequency; and (ii) detecting light from the light source at the first frequency. Pulsing the light source at the first frequency may involve emitting a succession of light pulses of substantially constant intensity.

In certain embodiments, presenting the user's heart rate includes presenting the heart rate on the worn biometric monitoring device. In certain embodiments, presenting the user's heart rate includes presenting the heart rate on an external device that periodically communicates with the worn biometric monitoring device.

Another aspect of the invention pertains to wearable fitness monitoring devices designed or configured to determine user's heart rate within an expected range of rates. Such devices may be characterized by the following features: a motion sensor configured to provide output corresponding to motion by a user wearing the fitness monitoring device; a heartbeat waveform sensor; and control logic having instructions for: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) processing the output data from the heartbeat waveform sensor to remove the periodic component from the output data from the heartbeat waveform sensor; (d) using the output data from the motion detecting sensor, determining a range of expected heart rates; (e) determining the user's heart rate from the output data produced in (c), wherein the determined heart rate exists within the range of expected heart rates; and (f) presenting the user's heart rate.

The control logic is typically, though not necessarily, located on the fitness monitoring device. It may be implemented as hardware, software, firmware, or any combination thereof. The data used by the control logic in executing the instructions described herein may be stored (e.g., buffered) by associated memory, registers, and the like, which may be entirely resident on the device or partially resident on a paired secondary device. Examples of suitable architectures for implementing the control logic are presented below with reference to, e.g., FIGS. 11A-G, 12A-C, 13A-B, and 14A-D.

In some devices, the motion detecting sensor is an accelerometer or a gyroscope. In certain embodiments, the device's heartbeat waveform sensor is a photoplethysmographic sensor having (i) a periodic light source, (ii) a photo detector positioned to receive periodic light emitted by the light source after interacting with the user's skin, and (iii) circuitry determining the user's heart rate from output of the photo detector. In some implementations, the photoplethysmographic sensor includes two periodic light sources straddling the photo detector. In some implementations, the photoplethysmographic sensor additionally includes a housing having a recess in which the photo detector is disposed. The housing of the photoplethysmographic sensor may have a second recess in which the periodic light source is disposed. In some designs, the housing protrudes at least about 1 mm above a base surface of the wearable fitness monitoring device arranged to press against the user's skin when worn. Further, the photoplethysmographic sensor further may include a spring configured to resist compression when the protruding housing presses against the user's skin. In certain embodiments, the photoplethysmographic sensor also includes an IML film over the photo detector and the periodic light source. In certain embodiments, the periodic light source is an LED.

In certain embodiments, the instructions for determining the range of expected heart rates include instructions for: (i) determining the user's heart rate when the output data from the motion detecting sensor indicates that the user is substantially stationary; (ii) determining the user's activity level and/or activity type from the periodic component of the output data from the motion detecting sensor; and (iii) determining the range of expected heart rates from the user's heart rate determined in (i) and the user's activity level and/or activity type determined in (ii). The minimum expected heart rate in the range of expected heart rates may be greater than the user's heart rate determined in (i). In some embodiments, the instructions for determining the user's activity type comprise instructions for inferring the activity type from information contained in the output data from the motion detecting sensor or detecting a manually entered selection of activity type.

In certain embodiments, the instructions for determining the range of expected heart rates include instructions for determining the user's step rate from the output data from the motion detecting sensor. In some implementations, the instructions for determining the user's heart rate include instructions for calculating the spectral density of the output data produced in (c).

In some implementations, the instructions for collecting the output data from the heartbeat waveform sensor include instructions for: (i) pulsing a light source in the worn biometric monitoring device at a first frequency; and (ii) detecting light from the light source at the first frequency. The instructions for pulsing the light source at the first frequency may include instructions for emitting a succession of light pulses of substantially constant intensity.

In some cases, the instructions for presenting the user's heart rate include instructions for presenting the heart rate on the worn biometric monitoring device. In some cases, the instructions for presenting the user's heart rate include instructions for presenting the heart rate on an external device that periodically communicates with the worn biometric monitoring device.

Yet another aspect of the disclosure pertains to methods of determining a user's heart rate when wearing a biometric monitoring device having a plurality of sensors including a heartbeat waveform sensor and a motion detecting sensor. The methods involve duty cycling the operation of the heartbeat waveform sensor. The methods may be characterized by the following operations: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) processing the output data from the heartbeat waveform sensor according to a duty cycle, wherein the processing comprises removing the periodic component from the output data from the heartbeat waveform sensor; (d) determining the user's heart rate; and (e) presenting the user's heart rate.

In some implementations, the motion detecting sensor is an accelerometer or a gyroscope. The heartbeat waveform sensor may be a photoplethysmography sensor or an ECG sensor.

In certain embodiments, the duty cycle includes an active phase of about 5 to 15 seconds for acquiring collecting output data from the heartbeat waveform sensor and determining the user's heart rate, followed by an inactive phase. In some implementations, successive active phases are separated by about 1 to 10 minutes. In some implementations, the active phase is triggered by receiving user input requesting a heart rate measurement. In some cases, the heartbeat waveform sensor and output data from the motion detecting sensor is collected in (a) for about 5-15 seconds during each minute of the duty cycle.

In certain embodiments, the methods additionally include the following operations: detecting that the user is attempting to read a heart rate; and temporarily suspending the duty cycling. In some cases, the methods additionally include the following operations: analyzing the output data from the motion detecting sensor to infer a low activity level; and, in response, temporarily suspending the duty cycling.

In some cases, the periodic movement detected by the motion sensor is a wearer's limb movements, which may be, e.g., steps, swim strokes, ankle revolutions while bicycling, and leg movements on cardio machines.

In some method implementations, the operation of collecting the output data from the heartbeat waveform sensor includes the following operations: (i) pulsing a light source in the worn biometric monitoring device at a first frequency; and (ii) detecting light from the light source at the first frequency. Pulsing the light source at the first frequency may involve emitting a succession of light pulses of substantially constant intensity.

In certain embodiments, presenting the user's heart rate includes presenting the heart rate on the worn biometric monitoring device. In certain embodiments, presenting the user's heart rate includes presenting the heart rate on an external device that periodically communicates with the worn biometric monitoring device.

Another aspect of the invention pertains to wearable fitness monitoring devices designed or configured to duty cycle when determining a user's heart rate. The wearable fitness monitoring devices may be characterized by the following features: a motion sensor configured to provide output corresponding to motion by a user wearing the fitness monitoring device; a heartbeat waveform sensor; and control logic comprising instructions for: (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats; (b) determining a periodic component of the output data from the motion detecting sensor; (c) processing the output data from the heartbeat waveform sensor according to a duty cycle, wherein the processing comprises removing the periodic component from the output data from the heartbeat waveform sensor; (d) determining the user's heart rate; and (e) presenting the user's heart rate.

The control logic is typically, though not necessarily, located on the fitness monitoring device. It may be implemented as hardware, software, firmware, or any combination thereof. The data used by the control logic in executing the instructions described herein may be stored (e.g., buffered) by associated memory, registers, and the like, which may be entirely resident on the device or partially resident on a paired secondary device. Examples of suitable architectures for implementing the control logic are presented below with reference to, e.g., FIGS. 11A-G, 12A-C, 13A-B, and 14A-D.

In some devices, the motion detecting sensor is an accelerometer or a gyroscope. In certain embodiments, the device's heartbeat waveform sensor is a photoplethysmographic sensor having (i) a periodic light source, (ii) a photo detector positioned to receive periodic light emitted by the light source after interacting with the user's skin, and (iii) circuitry determining the user's heart rate from output of the photo detector. In some implementations, the photoplethysmographic sensor includes two periodic light sources straddling the photo detector. In some implementations, the photoplethysmographic sensor additionally includes a housing having a recess in which the photo detector is disposed. The housing of the photoplethysmographic sensor may have a second recess in which the periodic light source is disposed. In some designs, the housing protrudes at least about 1 mm above a base surface of the wearable fitness monitoring device arranged to press against the user's skin when worn. Further, the photoplethysmographic sensor further may include a spring configured to resist compression when the protruding housing presses against the user's skin. In certain embodiments, the photoplethysmographic sensor also includes an IML film over the photo detector and the periodic light source. In certain embodiments, the periodic light source is an LED.

In certain embodiments, the duty cycle has an active phase of about 5 to 15 seconds for acquiring collecting output data from the heartbeat waveform sensor and determining the user's heart rate, followed by an inactive phase. In some cases, the successive active phases are separated by about 1 to 10 minutes. In certain implementations, the control logic additionally includes instructions for triggering the active phase by receiving user input requesting a heart rate measurement. In some implementations, the control logic includes instructions for collecting output data from the heartbeat waveform sensor and output data from the motion detecting sensor in (a) for about 5-15 seconds during each minute of the duty cycle.

In certain embodiments, the control logic includes instructions for: (i) detecting that the user is attempting to read a heart rate; and (ii) temporarily suspending the duty cycling. In certain embodiments, the control logic includes instructions for: (i) analyzing the output data from the motion detecting sensor to infer a low activity level; and (ii) temporarily suspending the duty cycling.

In some implementations, the instructions for collecting the output data from the heartbeat waveform sensor include instructions for: (i) pulsing a light source in the worn biometric monitoring device at a first frequency; and (ii) detecting light from the light source at the first frequency. The instructions for pulsing the light source at the first frequency may include instructions for emitting a succession of light pulses of substantially constant intensity.

In some cases, the instructions for presenting the user's heart rate include instructions for presenting the heart rate on the worn biometric monitoring device. In some cases, the instructions for presenting the user's heart rate include instructions for presenting the heart rate on an external device that periodically communicates with the worn biometric monitoring device.

These and other features of the disclosed embodiments will be presented in more detail below with reference to the associated drawings.

BRIEF DESCRIPTION OF DRAWINGS

FIG. 3A provides a cross sectional view of a sensor protrusion of an example portable monitoring device.

FIG. 3B depicts a cross sectional view of a sensor protrusion of an example portable monitoring device; this protrusion is similar to that presented in FIG. 3A with the exception that the light sources and photodetector are placed on a flat and/or rigid PCB.

FIG. 19 presents a graph of typical heart rates for different user activity types.

DETAILED DESCRIPTION

Figure 1:
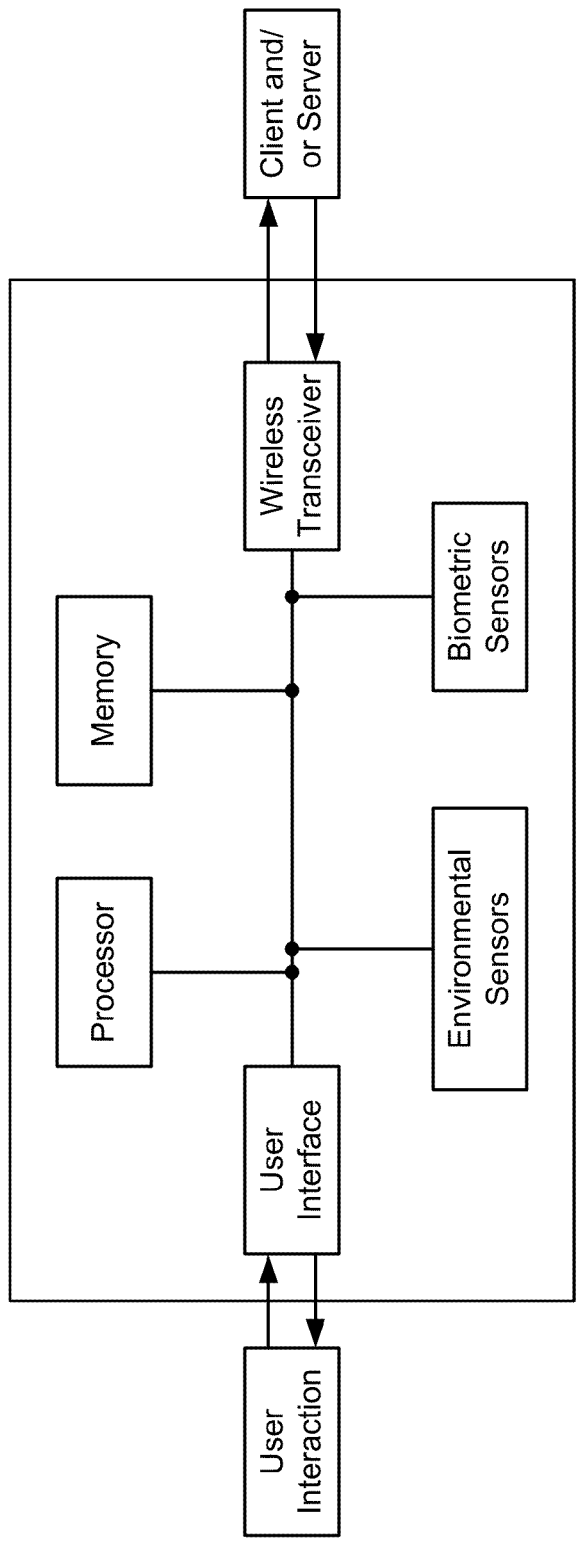
FIG. 1 illustrates an example portable monitoring device which enables user interaction via a user interface.

This disclosure is directed at biometric monitoring devices (which may also be referred to herein and in any references incorporated by reference as "biometric tracking devices," "personal health monitoring devices," "portable monitoring devices," "portable biometric monitoring devices," "biometric monitoring devices," or the like), which may be generally described as wearable devices, typically of a small size, that are designed to be worn relatively continuously by a person. When worn, such biometric monitoring devices gather data regarding activities performed by the wearer or the wearer's physiological state. Such data may include data representative of the ambient environment around the wearer or the wearer's interaction with the environment, e.g., motion data regarding the wearer's movements, ambient light, ambient noise, air quality, etc., as well as physiological data obtained by measuring various physiological characteristics of the wearer, e.g., heart rate, perspiration levels, etc.

Biometric monitoring devices, as mentioned above, are typically small in size so as to be unobtrusive for the wearer. Fitbit offers several varieties of biometric monitoring devices that are all quite small and very light, e.g., the Fitbit Flex is a wristband with an insertable biometric monitoring device that is about 0.5" wide by 1.3" long by 0.25" thick. Biometric monitoring devices are typically designed to be able to be worn without discomfort for long periods of time and to not interfere with normal daily activity.

In some cases, a biometric monitoring device may leverage other devices external to the biometric monitoring device, e.g., an external heart rate monitor in the form of an EKG sensor on a chest strap may be used to obtain heart rate data or a GPS receiver in a smartphone may be used to obtain position data. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

In general, the concepts discussed herein may be implemented in stand-alone biometric monitoring devices as well as, when appropriate, biometric monitoring devices that leverage external devices.

It is to be understood that while the concepts and discussion included herein are presented in the context of biometric monitoring devices, these concepts may also be applied in other contexts as well if the appropriate hardware is available. For example, many modern smartphones include motion sensors, such as accelerometers, that are normally included in biometric monitoring devices, and the concepts discussed herein may, if appropriate hardware is available in a device, be implemented in that device. In effect, this may be viewed as turning the smartphone into some form of biometric monitoring device (although one that is larger than a typical biometric monitoring device and that may not be worn in the same manner). Such implementations are also to be understood to be within the scope of this disclosure.

The functionality discussed herein may be provided using a number of different approaches. For example, in some implementations a processor may be controlled by computer-executable instructions stored in memory so as to provide functionality such as is described herein. In other implementations, such functionality may be provided in the form of an electrical circuit. In yet other implementations, such functionality may be provided by a processor or processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Standalone biometric monitoring devices may be provided in a number of form factors and may be designed to be worn in a variety of ways. In some implementations, a biometric monitoring device may be designed to be insertable into a wearable case or into multiple, different wearable cases, e.g., a wristband case, a belt-clip case, a pendant case, a case configured to be attached to a piece of exercise equipment such as a bicycle, etc. Such implementations are described in more detail in, for example, U.S. patent application Ser. No. 14/029,764, filed Sep. 17, 2013, which is hereby incorporated by reference for such purpose. In other implementations, a biometric monitoring device may be designed to be worn in only one manner, e.g., a biometric monitoring device that is integrated into a wristband in a non-removable manner may be intended to be worn only on a person's wrist (or perhaps ankle).

Figure 2A:
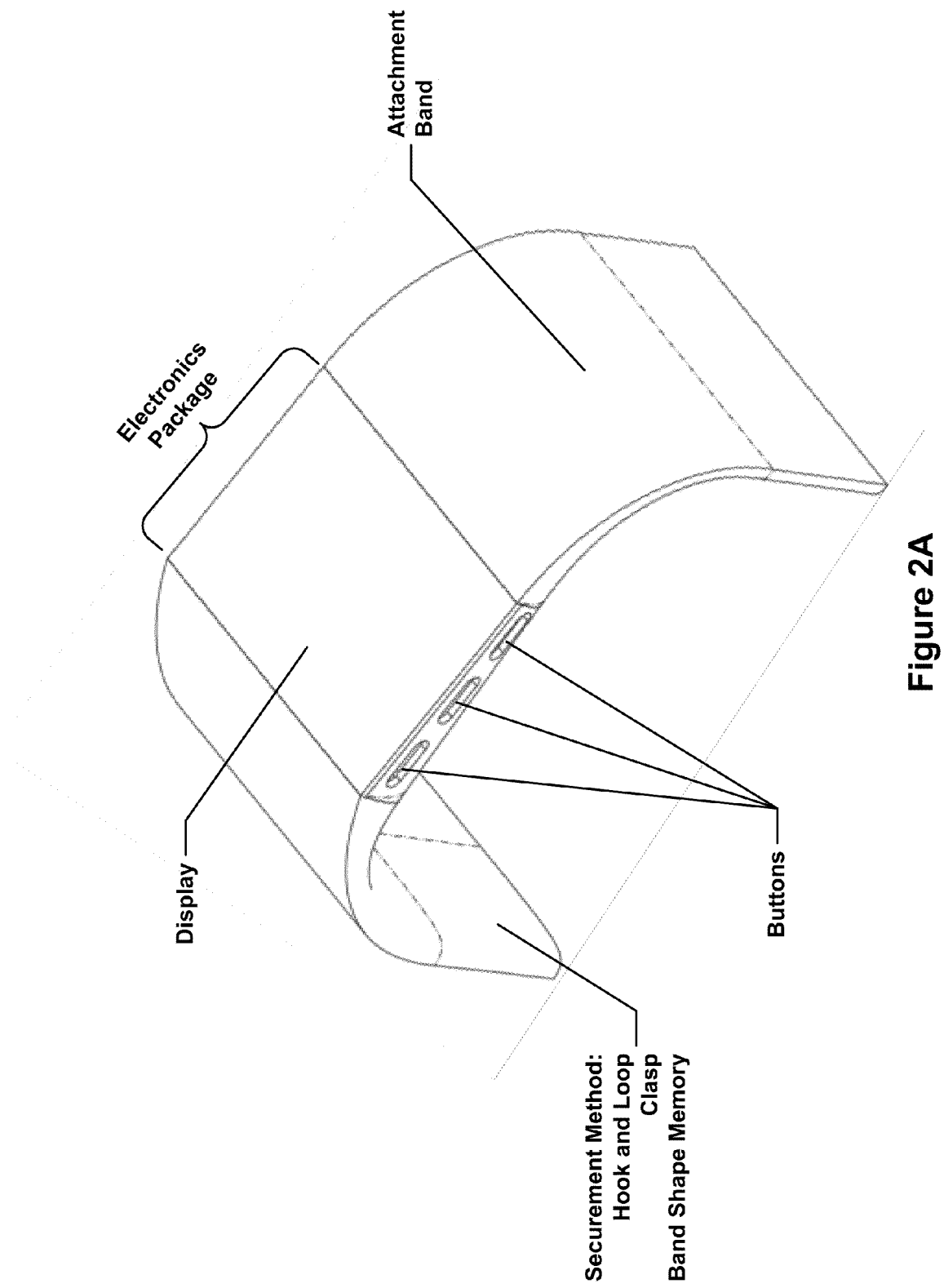
FIG. 2A illustrates an example portable monitoring device which may be secured to the user through the use of a band.
Figure 2B:
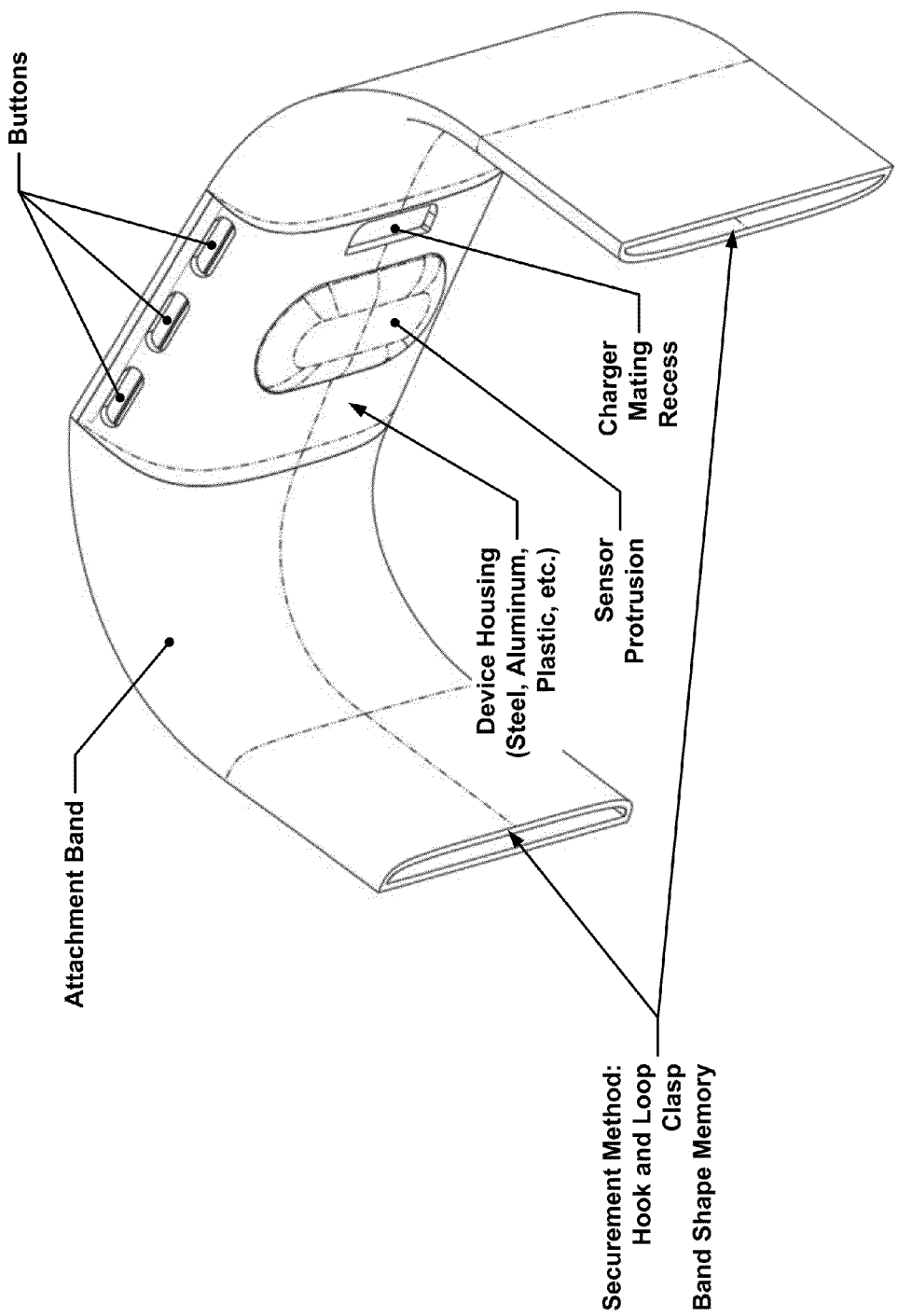
FIG. 2B provides a view of the example portable monitoring device of FIG. 2A which shows the skin-facing portion of the device.
Figure 2C:
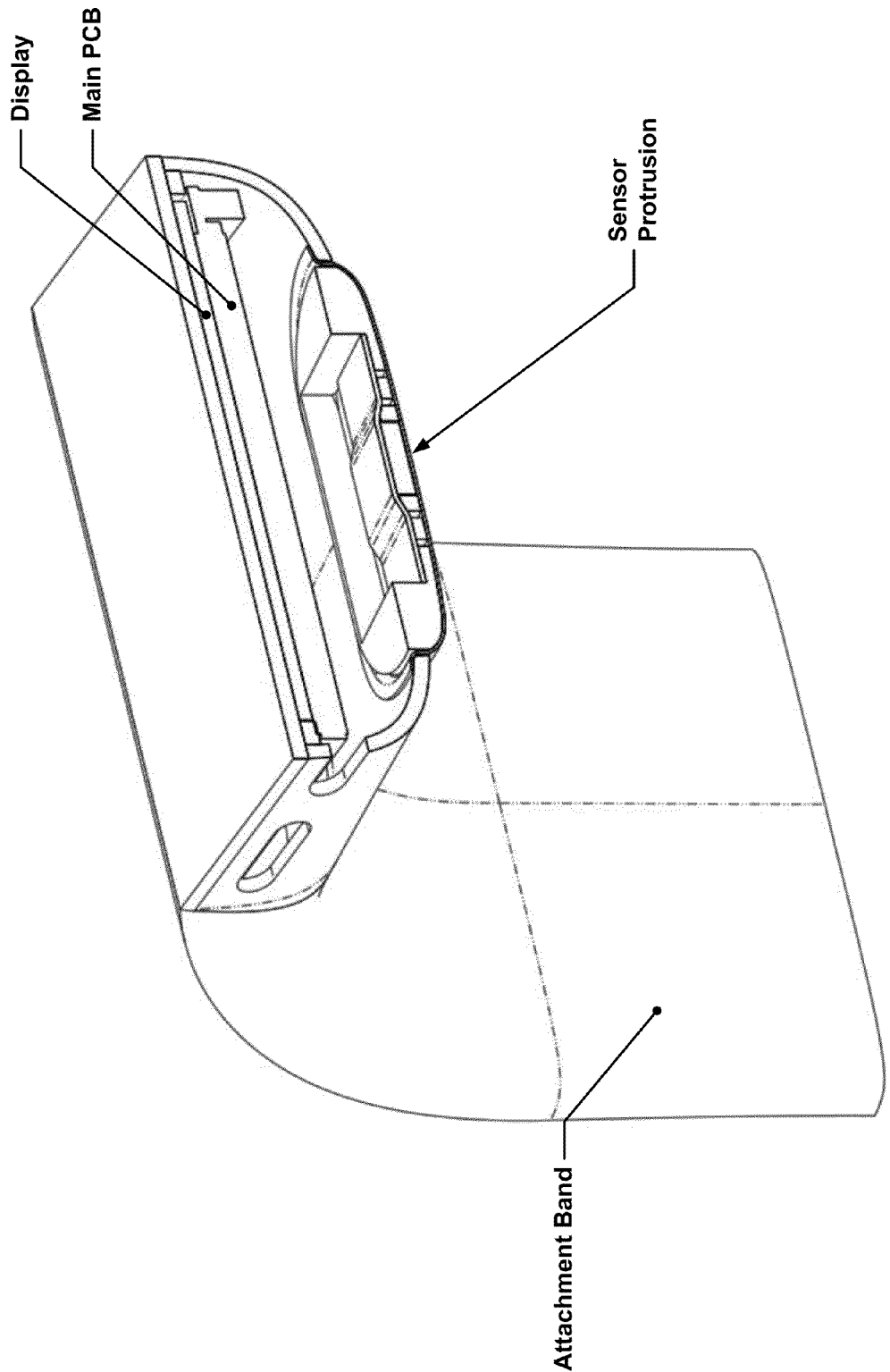
FIG. 2C provides a cross-sectional view of the portable monitoring device of FIG. 2A.

Portable biometric monitoring devices according to embodiments and implementations described herein may have shapes and sizes adapted for coupling to (e.g., secured to, worn, borne by, etc.) the body or clothing of a user. An example of a portable biometric monitoring devices is shown in FIG. 1; the example portable monitoring device may have a user interface, processor, biometric sensor(s), memory, environmental sensor(s) and/or a wireless transceiver which may communicate with a client and/or server. An example of a wrist-worn portable biometric monitoring device is shown in FIGS. 2A through 2C. This device may have a display, button(s), electronics package, and/or an attachment band. The attachment band may be secured to the user through the use of hooks and loops (e.g., Velcro), a clasp, and/or a band having memory of its shape, e.g., through the use of a spring metal band. In FIG. 2B, a sensor protrusion and recess for mating a charger and/or data transmission cable can be seen. In FIG. 2C, a cross-section through the electronics package is shown. Of note are the sensor protrusion, main PCB board, and display.

Portable biometric monitoring devices may collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the biometric monitoring device may calculate and store the user's step count using one or more biometric sensors. The biometric monitoring device may then transmit data representative of the user's step count to an account on a web service (e.g., www.fitbit.com), computer, mobile phone, or health station where the data may be stored, processed, and visualized by the user. Indeed, the biometric monitoring device may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS, GLONASS, or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics. The biometric monitoring device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the biometric monitoring device or the system collecting the data streams from the biometric monitoring device may calculate metrics derived from such data. For example, the device or system may calculate the user's stress and/or relaxation levels through a combination of heart rate variability, skin conduction, noise pollution, and sleep quality. In another example, the device or system may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Patent Application Ser. No. 13/156,304, titled "Portable Biometric Monitoring Devices and Methods of Operating Same" filed Jun. 8, 2011 and U.S. Patent Application 61/680,230, titled "Fitbit Tracker" filed Aug. 6, 2012, which are both hereby incorporated herein by reference in their entireties.

Physiological Sensors

Biometric monitoring devices as discussed herein may use one, some or all of the following sensors to acquire physiological data, including, but not limited to, the physiological data outlined in the table below. All combinations and permutations of physiological sensors and/or physiological data are intended to fall within the scope of this disclosure. Biometric monitoring devices may include but are not limited to types of one, some, or all of the sensors specified below for the acquisition of corresponding physiological data; indeed, other type(s) of sensors may also or alternatively be employed to acquire the corresponding physiological data, and such other types of sensors are also intended to fall within the scope of the present disclosure. Additionally, the biometric monitoring device may derive the physiological data from the corresponding sensor output data, but is not limited to the number or types of physiological data that it could derive from said sensor.

| Physiological Sensors | Physiological data acquired |
|---|---|
| Optical Reflectometer<br>Example Sensors:<br>Light emitter and receiver<br>Multi or single LED and photo diode arrangement<br>Wavelength tuned for specific physiological signals<br>Synchronous detection/amplitude modulation | Heart Rate, Heart Rate Variability<br>$SpO_2$ (Saturation of Peripheral Oxygen)<br>Respiration<br>Stress<br>Blood pressure<br>Arterial Stiffness<br>Blood glucose levels<br>Blood volume<br>Heart rate recovery<br>Cardiac health |
| Motion Detector<br>Example Sensors:<br>Inertial sensors, Gyroscopic sensors and/or Accelerometers<br>GPS | Activity level detection<br>Sitting/standing detection<br>Fall detection |
| Skin Temperature | Stress |
| EMG (eletromyographic sensor) | Muscle tension |
| EKG or ECG (electrocardiographic sensor)<br>Example Sensors:<br>Single-lead ECG or EKG<br>Dual-lead ECG or EKG | Heart Rate<br>Heart Rate Variability<br>Heart Rate Recovery<br>Stress<br>Cardiac health |
| Magnetometer<br>Laser Doppler<br>Power Meter | Activity level based on rotation |
| Ultrasonic Sensor | Blood flow |
| Audio Sensor | Heart Rate<br>Heart Rate Variability<br>Heart Rate Recovery<br>Laugh detection<br>Respiration<br>Respiration type, e.g., snoring, breathing, breathing problems (such as sleep apnea)<br>User's voice |
| Strain gauge<br>Example:<br>In a wrist band | Heart Rate<br>Heart Rate Variability<br>Stress |
| Wet/Immersion Sensor<br>Example Sensor:<br>Galvanic skin response | Stress<br>Swimming detection<br>Shower detection |

In one example embodiment, the biometric monitoring device may include an optical sensor to detect, sense, sample and/or generate data that may be used to determine information representative of, for example, stress (or level thereof), blood pressure, and/or heart rate of a user. (See, for example, FIGS. 2A through 3C and 11A through KKG). In such embodiments, the biometric monitoring device may include an optical sensor having one or more light sources (LED, laser, etc.) to emit or output light into the user's body, as well as light detectors (photodiodes, phototransistors, etc.) to sample, measure and/or detect a response or reflection of such light from the user's body and provide data used to determine data that is representative of stress (or level thereof), blood pressure, and/or heart rate of a user (e.g., such as by using photoplethysmography).

In one example embodiment, a user's heart rate measurement may be triggered by criteria determined by one or more sensors (or processing circuitry connected to them). For instance, when data from a motion sensor(s) indicates a period of stillness or of little motion, the biometric monitoring device may trigger, acquire, and/or obtain a heart rate measurement or data. (See, for example, FIGS. 9, 12A, and 12B).

Photoplethysmogram (PPG) signal can be recorded on the body using a light source (e.g., an LED) and a corresponding light detector (e.g., a photodiode). With each cardiac cycle the heart pumps blood to the periphery. Even though this pressure pulse is somewhat damped by the time it reaches the skin, it is enough to distend the arteries and arterioles in the subcutaneous tissue. The change in volume caused by the pressure pulse is detected by illuminating the skin with the light from a light-emitting diode (LED) and then measuring the amount of light either transmitted or reflected to a photodiode.

In certain embodiments, PPG or other technique is used to measure a heartbeat waveform. A "heartbeat waveform" generally refers to a variation of any measured signal caused by or correlated with a user's heartbeat driven blood flow. In some embodiments, the measured signal relates to blood circulation caused by the heart pumping blood through the circulatory system, which causes cardiovascular driven variations in capillary volume or other parameter. In some embodiments, the heartbeat waveform is measured by photoplethysmography (PPG). In such embodiments, the heartbeat waveform reflects blood volume changes in capillaries, which correlates with a user's heartbeat and pulse (an arterial palpation caused by the heartbeat). In some embodiments, the measured signal relates to muscular activities of the heart or electrocardiographic signals. In some embodiments, the cardiac activities or signals can be measured by ECG to obtain the heartbeat waveform. A heartbeat waveform represents information for one or more cardiac cycles, which corresponds to a complete heartbeat from its generation to the beginning of the next beat. The frequency of the cardiac cycle is described by the heart rate, which is typically expressed as beats per minute. A heartbeat waveform typically includes information about various stages of a heartbeat, e.g., amplitude, frequency, and/or shape of waveform over one or more cycles. In many embodiments, a heartbeat waveform is used to obtain a user's heart rate.

This PPG signal can thus be used to estimate the heart rate of the user. PPG reflects a combination of the underlying change in blood volume due to heart beats as well as the change in optical properties of the underlying tissue and the device—skin interface due to subject motion. Typically, the human heart rate is estimated in the range 40-240 beats per min (bpm).

Figure 12A:
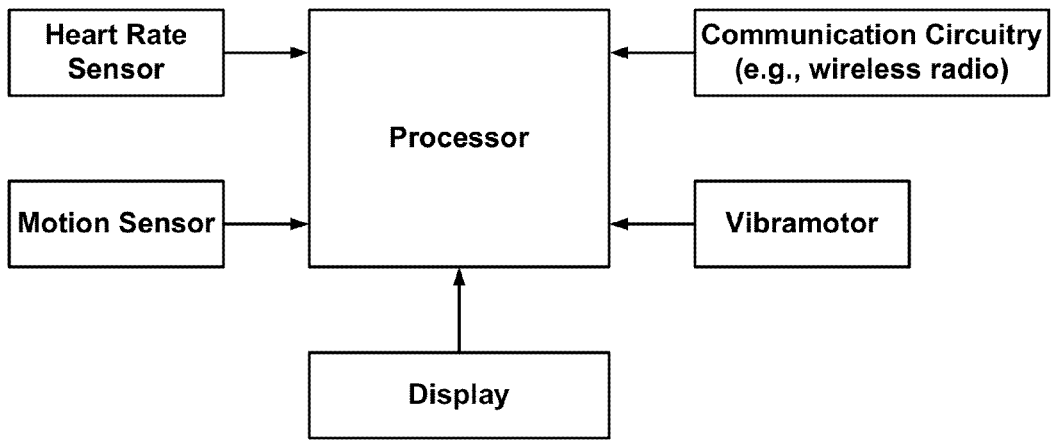
FIG. 12A illustrates an example of a portable biometric monitoring device having a heart rate or PPG sensor, motion sensor, display, vibromotor, and communication circuitry which is connected to a processor.

FIG. 12A illustrates an example of a portable biometric monitoring device having a heart rate or PPG sensor, motion sensor, display, vibromotor, and communication circuitry which is connected to a processor.

Figure 12B:
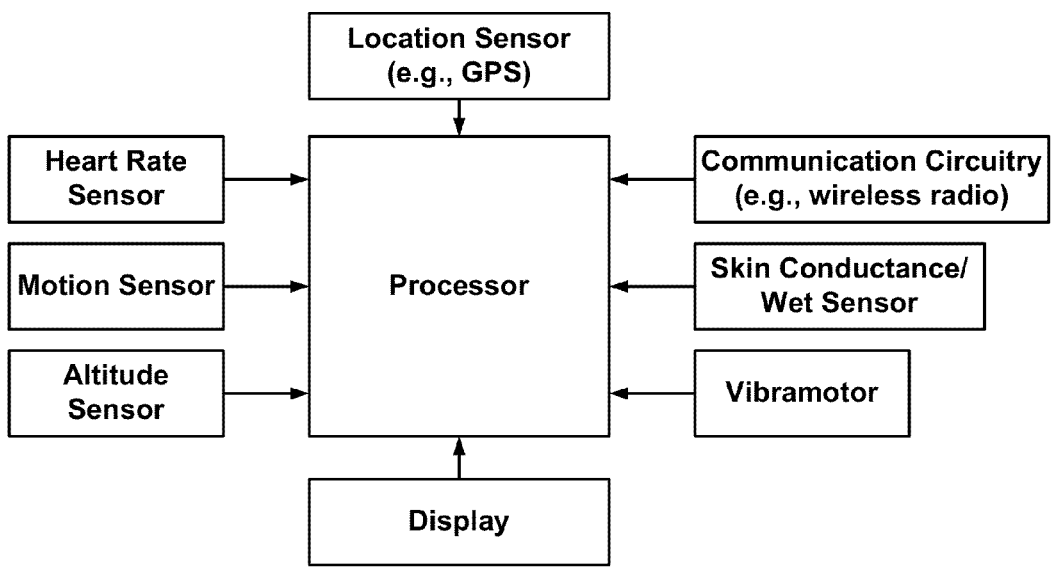
FIG. 12B illustrates an example of a portable biometric monitoring device having a heart rate or PPG sensor, motion sensor, display, vibromotor, location sensor, altitude sensor, skin conductance/wet sensor and communication circuitry which is connected to a processor.

FIG. 12B illustrates an example of a portable biometric monitoring device having a heart rate or PPG sensor, motion sensor, display, vibromotor, location sensor, altitude sensor, skin conductance/wet sensor and communication circuitry which is connected to a processor.

In one embodiment, when the motion sensor(s) indicate user activity or motion (for example, motion that is not suitable or optimum to trigger, acquire, and/or obtain desired heart rate measurement or data (for example, data used to determine a user's resting heart rate)), the biometric monitoring device and/or the sensor(s) employed to acquire and/or obtain a desired heart rate measurement or data may be placed in, or remain in, a low power state. Since heart rate measurements taken during motion may be less reliable and may be corrupted by motion artifacts, it may be desirable to decrease the frequency with which heart rate data samples are collected (thus decreasing power usage) when the biometric monitoring device is in motion.

In another embodiment, a biometric monitoring device may employ data (for example, from one or more motion sensors) indicative of user activity or motion to adjust or modify characteristics of triggering, acquiring, and/or obtaining desired heart rate measurements or data (for example, to improve robustness to motion artifact). For instance, if the biometric monitoring device receives data indicative of user activity or motion, the biometric monitoring device may adjust or modify the sampling rate and/or resolution mode of sensors used to acquire heart rate data (for example, where the amount of user motion exceeds a certain threshold, the biometric monitoring device may increase the sampling rate and/or increase the sampling resolution mode of sensors employed to acquire heart rate measurement or data.) Moreover, the biometric monitoring device may adjust or modify the sampling rate and/or resolution mode of the motion sensor(s) during such periods of user activity or motion (for example, periods where the amount of user motion exceeds a certain threshold). In this way, when the biometric monitoring device determines or detects such user activity or motion, the biometric monitoring device may place the motion sensor(s) into a higher sampling rate and/or higher sampling resolution mode to, for example, enable more accurate adaptive filtering of the heart rate signal. (See, for example, FIG. 9).

Figure 9:
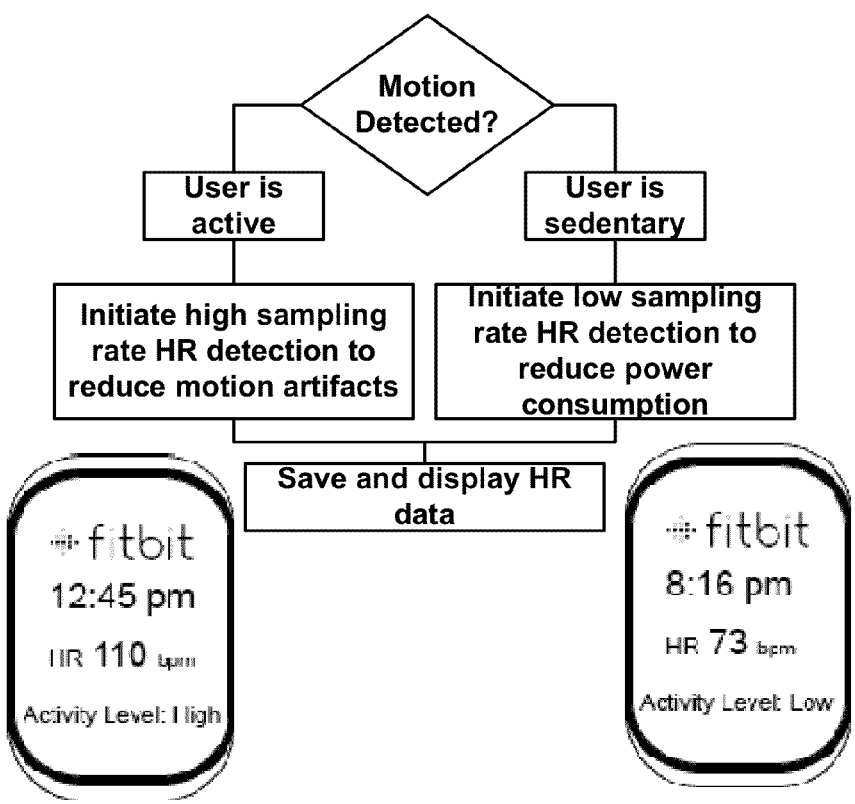
FIG. 9 illustrates an example of a portable biometric monitoring device that changes how it detects a user's heart rate based on how much movement the biometric monitoring device is experiencing.

FIG. 9 illustrates an example of a portable biometric monitoring device that changes how it detects a user's heart rate based on how much movement the biometric monitoring device is experiencing. In the case where there is motion detected (e.g., through the use of an accelerometer), the user may be considered by the biometric monitoring device to be "active" and high-sampling-rate heart rate detection may occur to reduce motion artifacts in the heart rate measurement. This data may be saved and/or displayed. In the case that the user is determined by the biometric monitoring device to not be moving (or to be relatively sedentary), low-sampling-rate heart rate detection (which does not consume as much power) may be adequate to measure a heart rate and may thus be used.

Notably, where a biometric monitoring device employs optical techniques to acquire heart rate measurements or data, e.g., by using photoplethysmography, a motion signal may be employed to determine or establish a particular approach or technique to data acquisition or measurement by the heartbeat waveform sensor (e.g., synchronous detection rather than a non-amplitude-modulated approach) and/or analysis thereof. (See, for example, FIG. 11E). In this way, the data which is indicative of the amount of user motion or activity may cause the biometric monitoring device to establish or adjust the type or technique of data acquisition or measurement used by an optical heartbeat waveform sensor or sensors.

For example, in one embodiment, a biometric monitoring device (or heart-rate measurement technique as disclosed herein) may adjust and/or reduce the sampling rate of optical heart rate sampling when motion detector circuitry detects or determines that the biometric monitoring device wearer's motion is below a threshold (for example, if the biometric monitoring device determines the user is sedentary or asleep). (See, for example, FIG. 9). In this way, the biometric monitoring device may control its power consumption. For example, the biometric monitoring device may reduce power consumption by reducing the sensor sampling rate—for instance, the biometric monitoring device may sample the heart rate (via the heartbeat waveform sensor) once every 10 minutes, or 10 seconds out of every 1 minute. Notably, the biometric monitoring device may, in addition thereto or in lieu thereof, control power consumption via controlling data processing circuitry analysis and/or data analysis techniques in accordance with motion detection. As such, the motion of the user may impact the heart rate data acquisition parameters and/or data analysis or processing thereof.

Motion Artifact Suppression in Heartbeat Waveform Sensors

As discussed above, the raw heartbeat waveform signal measured by a PPG sensor may be improved by using one or more algorithms to remove motion artifacts. In certain embodiments, data from a motion sensor is employed to gauge a user's motion and an adaptive filter is employed to remove the motion artifact from the heart rate signal when the user's motion is periodic. Movement of the user (for determining motion artifacts) may be measured using sensors including, but not limited to, accelerometers, gyroscopes, proximity detectors, magnetometers, etc. The goal of such algorithms is to remove components of the PPG signal attributable to movement (movement artifacts) using the movement signal captured from the other sensors as a guide. In one embodiment the movement artifacts in the PPG signal may be removed using an adaptive filter based on a hybrid Kalman filter and a least mean square filter or a recursive least squares filter. The heart rate or other feature of a heartbeat waveform may then be extracted from the cleaned/filtered signal using a peak counting algorithm or a power spectral density estimation algorithm. Alternatively, a Kalman filter or particle filter may be used to remove such movement artifacts.

Another approach that may be used to calculate the heart rate frequency is to create a model of the heart rate signal as $Y=Y_{dc}+\Sigma a_k^* \cos k\theta + b_k^* \sin k\theta$, where k is the order of harmonic components, and $\theta$ is a model parameter for heart rate. This model may then be fit to the signal using either an extended Kalman filter or a particle filter. This model exploits the fact that the signal is not sinusoidal so contains power both at the fundamental harmonic as well as multiple additional harmonics.

Alternately, the signal may be modeled as $Y=Y_{dc}+\Sigma a_k^* \sin(k^* w_{motion} t+\theta)+\Sigma b_k^* \sin(k^* w_{HR} t+\emptyset)$, where $w_{motion}$ is estimated directly from the accelerometer signal (or another motion sensor signal).

Various techniques may be employed to improve motion compensation. Some of these techniques are presented in the following sub-sections.

High Band Pass Filter

PPG signals tend to have slow variations due to causes other than heart beats, for example respiration, movement of blood into or out of the measurement region, user motions that change the orientation of the monitoring device. Removing these slow variations by high pass filtering the PPG signal before applying the adaptive filter may improve the performance of the adaptive filter. Therefore, certain embodiments provide a high pass filter placed in front of the adaptive filter. See FIG. 17. In some implementations, the cutoff frequency of the high pass filter is positioned as high as possible, but no higher than the lowest heart rate expected (which is around 40 bpm for typical applications), so the high pass filter cutoff may be placed somewhere between about 0.3 and 0.6 Hz.

In some implementations, the high pass cutoff frequency is chosen to be approximately the user's previously detected resting heart rate, which may be determined by a variety of techniques. These include at least the following. (1) Measuring a user's heart rate soon after she wakes up and is still stationary in bed. As described elsewhere, the biometric monitoring device may employ other algorithms to automatically detect when the user is asleep/awake. (2) Measuring the average heart rate of the user while the user is sleeping. As an example, a user's resting heart rate may be calculated from sleeping heart rate using an equation such as resting HR=sleeping HR/0.83. (3) Measuring the heart rate of the user when the user is awake and stationary. Taking a few of these measurements during the day and calculating the Nth percentile of the lowest of these measurements (e.g., N=10 or 5 or 2) provides a good approximation of resting heart rate. The method of approximating resting heart rate during all day activities can further be used to compute a user's resting heart rate at different locations. For example, the biometric monitoring device can compute a user's resting heart rate at home and at work. In addition to facilitating use in a high pass filter, such information can show trends in home and work resting heart rate over time.

High band pass filter frequency may be set based on the user's detected activity level. In such embodiments, the lowest expected heart rate differs based on activity; for example most users will have a heart rate of higher than about 50 bpm when walking or running. Therefore, in certain implementations, the PPG processing logic dynamically adjusts the frequency cutoff of the high pass filter by inferring the activity of the user using, e.g., inertial sensors such as accelerometers. As the user's level of activity increases, as inferred by motion interpreting logic, the high pass filter cutoff may be adjusted upward accordingly. In certain embodiments, when the processing logic determines that the user is engaged in walking, it increases high pass filter cutoff in proportion to the user's step rate, elevation climbed, etc. An example of the basis for such adjustments can be seen by the variation in a normal user's heart rate between running and walking as shown in FIG. 19.

Create Spectrogram Heart Rate Monitor Output (Time Domain->Frequency Domain)

Figure 18:
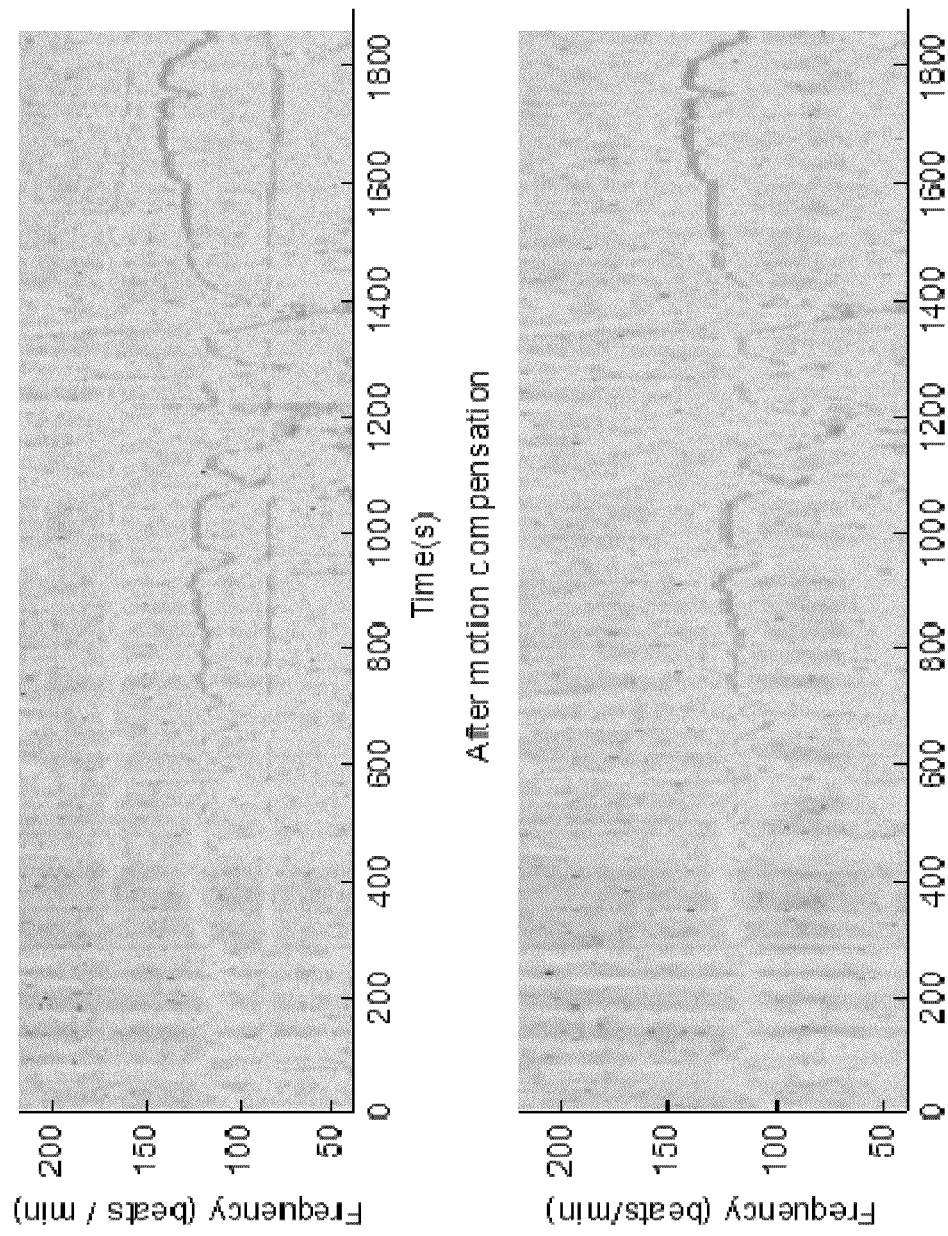
FIG. 18 presents an example of a frequency domain heartbeat waveform sensor signal that undergoes two passes of adaptive filtering. The upper panel of the figure shows the unfiltered signal and the lower panel shows the same signal after two passes of adaptive filtering.

At an appropriate time in the signal processing, the processing logic transforms the time domain signal to a frequency domain signal, which can be represented as frequency versus time. FIG. 18 presents examples of the frequency domain signal. While the processing logic may perform the transformation using a Fast Fourier Transform, other techniques may be suitable. Examples include wavelet transforms and cepstral transforms.

Motion Compensation Process

The heartbeat waveform analysis logic may track the user's motion, as detected by the device, and apply an adaptive filter to remove or reduce the motion artifact from the heart rate signal when the user's motion is periodic. In certain embodiments, the motion artifact is measured using an accelerometer, a gyroscope, or an accelerometer and a gyroscope.

In certain embodiments, the adaptive filter is applied to the heartbeat waveform data twice in series. In other word, the output of a first pass of the adaptive filter is input for the second pass of the adaptive filter. Although typically unnecessary, the logic may run the adaptive filter more than two times. This approach may be employed to remove both the fundamental frequency and the higher harmonics of the motion artifact, as measured using, e.g., an accelerometer.

On the first pass, the filter typically removes the fundamental frequency of the motion artifact, and on the second pass, it removes a second harmonic (or other lower power harmonic). For example, the user may be walking at nominal rate of 1 Hz to produce an approximately 1 Hz motion artifact in the heartbeat waveform sensor signal. The first pass through the adaptive filter may remove this artifact, but not its first harmonic at nominally 2 Hz, which may interfere with processing the heartbeat waveform signal. Passing the "cleaned" heartbeat waveform signal through the adaptive filter a second time may remove the second harmonic of the motion artifact to further clean the signal. In some implementations, no further cleaning is needed, as higher order harmonics are of low power compared the heart rate signal and/or at frequencies far removed from the heart rate signal.

FIG. 18 presents an example of a frequency domain heartbeat waveform sensor signal that undergoes two passes of adaptive filtering. The upper panel of the figure shows the unfiltered signal and the lower panel shows the same signal after two passes of adaptive filtering. Note that the motion artifacts of both higher and lower frequencies than the true heart rate signal are removed.

Identify Heartbeat Waveform Track

A heartbeat waveform track is a trace of substantially continuous points (with few or no jump discontinuities) in frequency vs. time for the processed heartbeat waveform sensor output data. The points of the trace may have a relatively constant power density.

In certain embodiments, after removing the motion artifact using the adaptive filter, the power spectral density of the signal is calculated. The peak with the highest amplitude can be chosen as the most likely estimate of the current heart rate. Alternately, techniques like dynamic programming or multi target tracking can be used to estimate the heart rate 'track' in the spectrogram in the presence of other tracks caused due to motion and its higher harmonics. In all approaches, one or more of the following techniques may be implemented to improve performance:

1. The minimum heart rate expected for a user is related to the step rate or other cadence measurement of a user who is walking or running. By measuring the step rate of a user with, e.g., an accelerometer, a heart rate monitor can set a lower bound on the expected heart rate of the user. This serves to remove many motion artifacts related peaks which typically occur at lower frequencies. A similar technique can be applied to rates of other user activities such as swim strokes, bicycle peddling cadence, and rates of other activities described herein.

2. The minimum heart rate expected for a user who is biking is related to the speed and incline at which the user is biking. By measuring the speed with a cadence sensor, GPS or other speed measurement sensor, and inclination with an altimeter, GPS or other height measuring sensor, a heart rate monitor can set a lower bound on the expected heart rate of the user. This serves to remove many motion artifacts which typically happen at lower frequencies.

3. Lower bounds on the expected heart rate can also be calculated based on different features in the accelerometer signal like the total power, standard deviation of one or more axes, power in a particular frequency band etc. Higher total accelerometer power or higher standard deviation of one or more axes are typically related to a person engaged in strenuous activity which leads to a higher heart rate.

4. The minimum heart rate of a user walking, running or biking is also higher than the sedentary heart rate of the user. This sedentary heart rate can be calculated when the user is stationary or when he or she is sleeping and may be used as a lower bound on the heart rate, alone or in addition to another mechanism for determining a lower bound (e.g., the lowest heart rate expected for the user's current activity mode).

5. The activity mode of the user like running, walking and biking can either be automatically calculated using other sensors on the device like inertial sensors, or can be manually entered by the user.

Determine Quality of the Heart Rate Estimate

In certain embodiments, the signal processing logic calculates the quality of the heart rate estimate by measuring the magnitude of the power spectral density at the output for the heartbeat trace compared to the background power. This monitor may then provide this to the user as feedback. The feedback can take various forms. In one example, it presents a confidence regarding how much the heart rate estimate can be trusted. In another example, it provides instructions for improving the generation of future heart rate measurements. For example, it may present information on whether the user needs to physically adjust the placement and tightness of the device to achieve a better signal. Further details are presented in the discussion of FIG. 17.

Example Architecture for Motion Compensation in a Heartbeat Waveform Sensor

Figure 17:
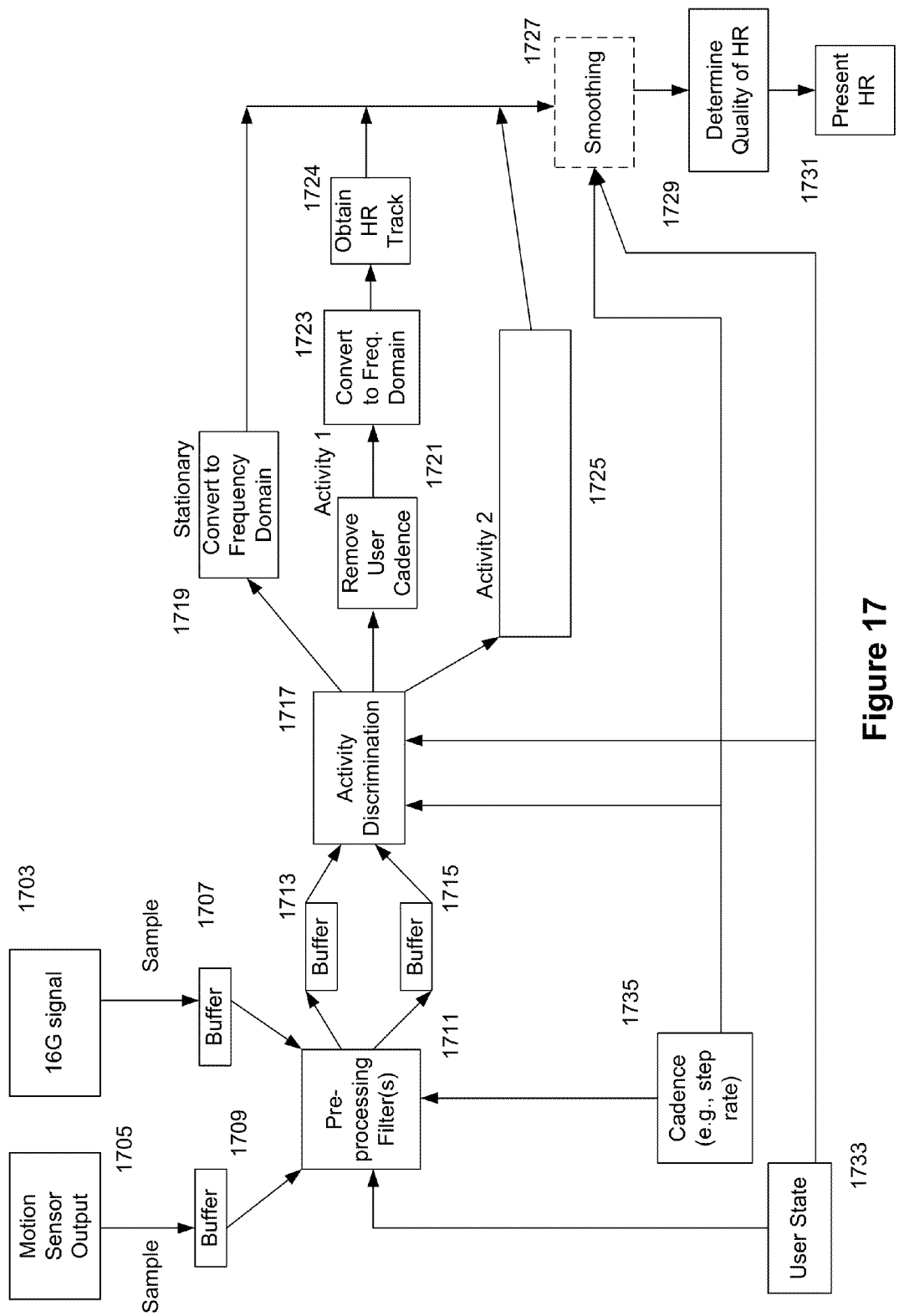
FIG. 17 presents a block diagram of signal processing logic for applying motion compensation to a heartbeat waveform signal in accordance with certain embodiments.

FIG. 17 presents an example architecture (and associated process flow) for a variety of motion compensating heartbeat waveform sensor. In the depicted example, the signal processing logic receives two input signals: (1) heartbeat waveform signals from a PPG sensor 1703, for example, and (2) motion detection sensor 1705 output. The raw output from a heartbeat waveform sensor may be sampled at a defined frequency and the samples may be buffered for processing together. Similarly, the motion signal may be sampled and stored. In certain embodiments, the heartbeat waveform sensor and/or the motion detection sensor outputs are sampled at a rate of about 20 to 200 Hz or about 20 Hz to 60 Hz. In certain embodiments, the heartbeat waveform sensor and motion detection sensor outputs are sampled at the same frequency. In one example, the two signals are sample at 25 Hz. Regardless of the sampling rates, the outputs are stored for a limited time in buffers 1707 and 1709.

In certain embodiments such as the one depicted in FIG. 17, one or more additional inputs are provided to the motion compensating logic. In some implementations, an additional input is a user activity level or activity type, as inferred from output data from the motion sensor or other sensors, or detected from a manual setting by the user. Output from device sensors such as motion detecting sensors may be employed for this purpose. In the architecture depicted in FIG. 17, the signal processing logic employs the user's current state (e.g., sedentary, participating in activity 1, participating in activity 2, etc. —see block 1733) and the user's activity rate (see block 1735), sometimes referred to as cadence. The user's activity type/state is optional in some embodiments. Examples of activity types include, in addition to sedentary, walking, running, biking, etc. In some implementations, the device includes a periodic motion rate calculator that calculates the user's step rate or other periodic motion rate. Periodic motion rates are used at various stages in the process.

The buffered heart rate and motion sensor outputs may be separately processed in some embodiments. In other embodiments, they are processed together early in the motion compensation process. In the designs embodied by the architecture of FIG. 17, both buffered output samples are subjected to the same "pre-processing" operations (see block 1711). Examples of such pre-processing operations include band pass filtering, high pass filtering, low pass filtering, and denoising. As an example, both types of sample are filtered by a filter, which may remove slow varying components of the outputs, which introduce signal processing challenges as explained above. In the example, both signals are subjected to the same pre-processing but they are not combined.

In some embodiments, pre-processing block 1711 dynamically chooses a cutoff high pass frequency based on user activity level or activity type as described above. Inputs from 1733 and 1735 may be used for this purpose. As an example, a high pass cut off of 0.7 Hz, corresponding to 42 beats per minute, may be appropriate for some user activities but not others. Therefore, in some implementations, the algorithm attempts to determine the user's current activity and choose an appropriate cut off frequency for that activity. In one example, the algorithm determines the user's step rate from the motion sensor output data and uses the step rate to choose an appropriate high pass cut off frequency.

In the embodiment depicted in FIG. 17, the signal processing logic buffers the pre-processed heartbeat waveform sensor signal in a buffer 1713 and buffers the pre-processed motion sensor signal in a buffer 1715. In certain embodiments, each buffer holds data samples from about 1 to 40 seconds or from about 5 to 20 seconds. In one example, the buffer holds about 10 seconds of data.

In certain implementations, the signal processing logic includes different channels for processing heartbeat waveform data based on different characteristics of the data. Such characteristics may depend on inferred or user-set characteristics of the user, which, in some cases, may be varied dynamically. Examples of such characteristics include user activity type, user activity level (e.g., cadence or step rate), time of day, time of the week, location, etc. In the embodiment depicted in FIG. 17, the characteristic is activity type and/or level (e.g., periodic motion rate). As shown, an activity discrimination logic block 1717 receives as inputs the user's state (from block 1733) and the user's cadence (from block 1735). The activity discrimination block may be viewed as a form of multiplexer. The signal processing logic uses this information, or other information in other embodiments, to choose a channel. In some implementations, the logic chooses a channel based on user input from a device's user interface, which may be provided on the biometric monitoring device or a secondary device. If the device detects that the user entered a particular mode like "biking," the processing logic may decide that channel for activities including biking should be used to process the heartbeat waveform. In the depicted embodiment, there are three channels: a "stationary" channel, a "first activity" channel, and a "second activity" channel. Examples of activity processing channels include a channel for walking/running, one for working out, and/or channels for more specific types of working out such as biking, swimming, elliptical training, rock climbing, tennis, etc. Of course, the stationary mode channel is inferred when sensor output suggests that the user is generally inactive. Typically, there may be two or more channels. In certain embodiments, there are 2-20 channels, or 2-10 channels, or 2-5 channels.

In each of the channels, the signal processing logic converts the time domain signals acquired from the sensors to frequency domain signals. In the depicted embodiment, this is accomplished at a logic block 1719 for the stationary mode channel, a logic block 1723 for the first activity channel, and a logic block 1725 for the second activity channel.

As an example, a stationary mode channel may be implemented as follows. First, the stationary mode is determined based on the user's motion. If the user has not moved or moved only slightly during a recent time window (e.g., 5 minutes), the processing logic (e.g., block 1717) deems the user stationary for purposes of further processing of the buffered sensor output data. In this channel, the logic assumes that there is no motion artifact, so the processing is simplified in comparison to processing other channels.

Some or all of the following operations may be performed in the stationary channel as well as one or more other "activity" channels:

A. Perform a Fast Fourier Transform or other time to frequency domain transform. This may provide an initial "estimate" of the user's heart rate. Before this transform, all processing is conducted in the time domain. As mentioned, block 1719 of FIG. 17 performs this operation in the stationary channel.

B. Identify a heart rate track in the spectral representation of the filtered output data from the heartbeat waveform sensor. This process may be performed as described above. In certain embodiments, this is performed by excluding putative heart rate tracks below an expected level for the user's activity type. In the case of the stationary mode channel, this level is about 30 beats per minute.

C. Optionally smooth the estimated time varying heart rate to provide a smoothed output heart rate. Smoothing may be performed using many different smoothing filters known to those of skill in the art. In the embodiment depicted in FIG. 17, an optional smoothing logic block 1727 smoothes the time varying heart rate signal using input from blocks 1733 (user state) and 1735 (user cadence).

D. In some implementations, the signal processing logic assesses the "confidence" of the heart rate value determined from motion compensated process. In the embodiments of FIG. 17, a logic block 1729 makes this assessment. As explained elsewhere herein, the confidence may be determined by any of various techniques. In one approach, it uses information contained in a heartbeat waveform sensor; for example, the signal-to-noise ratio of the sensor's output data. When a low signal-to-noise ratio is detected, the confidence is low; when a high signal to noise ratio is detected, the confidence is higher.

E. Typically, the signal processing logic completes its processing of buffered heartbeat waveform data by presenting its calculated heart rate to the user. See logic block 1731 in FIG. 17. In certain embodiments, the signal processing logic presents the heart rate value to the user along with the calculated confidence in the presented heart rate. In some cases, the logic presents the heart rate value along with a recommendation for adjusting the device position to improve confidence in subsequent heart rate calculations. As examples, the logic may suggest wearing the device tighter or wearing it higher on the user's forearm.

The heart rate information may be presented to the user visually, audibly, tactilely, etc. The information may be provided via the biometric monitoring device and/or an associated secondary device such as a paired phone, table, computer, or other processing device. In some implementations, the information is provided via a "one touch" heart rate monitor design. See e.g., U.S. patent application Ser. No. 14/154,009, filed Jan. 1, 2014, and incorporated herein by reference in its entirety.

Turning to the first activity mode channel, an example of the processing for this mode may be implemented as follows. Initially, the first activity mode is determined based on the user's motion. Many criteria may be employed to determine the user's activity mode. At a minimum, the devices should receive sensor output suggesting that the user is engaged in some activity and is not sedentary. In a typical implementation, a motion sensor output shows that the user or a user's limb is moving at a reasonable rate. Alternatively, the processing logic may rely on manual input from the user indicating that the user is engaged in the first activity. Regardless of how the signal processing logic (e.g., block 1717) determines that the user is participating in the first activity, it begins processing of the buffered output data via the first activity channel. In this channel, the logic assumes that there is a motion artifact that should be removed or reduced before calculating the user's heart rate. Otherwise, the channel processing may be implemented similarly to that of the stationary channel.

The first activity channel may employ an adaptive filter to remove or reduce the motion artifacts from the time domain signal. See block 1721 in the embodiments of FIG. 17. In certain implementations, the adaptive filter attempts to predict the heartbeat waveform sensor output data from the motion sensor output data. This determines the motion artifact in the heartbeat waveform sensor output because the motion artifact is the only component common to the two output signals. Stated another way, the adaptive filter subtracts the motion artifact from the heart rate output signal to provide "cleaned" heart rate output data. Examples of adaptive filtering that may be employed include least mean square filtering and recursive least squares filtering. Optionally, the processing logic passes the cleaned heartbeat waveform output signal through the adaptive filter a second time, as explained above. Examples of other motion compensation algorithms that may be employed include dynamic programming, and multi-target tracking. As mentioned, the motion compensation process may be employed two more times on the heartbeat waveform signal. The motion sensor output used in motion compensation may represent any of a variety of user physical motions. Examples include periodic limb movements such as steps, swim strokes, ankle revolutions while bicycling, and leg movements on cardio machines such as stationary bicycles, treadmills, and elliptical machines.

Further processing of the heartbeat waveform signal in the first activity channel may proceed generally as described above for the stationary channel. However, identifying the heartbeat track may employ more sophisticated processing. The following are operations that may be employed in first activity channel.

A. Employ an FFT or other frequency domain conversion technique to get an "estimate" of the user's heart rate from the time domain data output from the adaptive filter. See block 1723 for location of this operation in the embodiments of FIG. 17.

B. Identify a heart rate track in the spectral representation of the filtered output data from the heartbeat waveform sensor. See block 1724 in the embodiments of FIG. 17. In certain embodiments, this is performed by excluding putative heart rate tracks below an expected level for the user's activity type.

In the case of the stationary mode channel, this level is about 40 beats per minute. In some implementations, the logic creates or employs a band of expected heart rate frequencies for each activity type and/or activity level, and, for any given activity type, excludes all potential heart rates outside the band. Examples of information that may be used to define the bands include inferred user activity type, step rate, and defined sensor outputs (e.g., GPS speed while biking, altimeter change for bicycling). In certain embodiments, the minimum heart rate band for any activity is greater than the user's sedentary heart rate (previously determined).

C. Smooth the estimate to get a smoothed output heart rate.

D. Assess the "confidence" of the output heart rate. This process optionally uses the user's motion as determined by a different process. It may optionally use the signal-to-noise ratio of the motion sensor output.

E. Present the calculated heart rate to the user. This information may be presented along with the confidence level and/or a recommendation for adjusting device position to improve confidence. Information may be presented to the user visually, audibly, tactilely, etc. The information may be provided via the biometric monitoring device and/or an associated secondary device such as a paired phone, table, computer, or other processing device. In some implementations, the information is provided via a "one touch" heart rate monitor design. See e.g., U.S. patent application Ser. No. 14/154,009, filed Jan. 1, 2014, and incorporated herein by reference in its entirety.

As mentioned, additional activity channels may be employed, such as the channel associated with block 1725 in FIG. 17. In many implementations, the additional channels employ variations on the first activity channel depicted in FIG. 17. The variations may include the location of the boundaries on the minimum and maximum calculated heart rate and how aggressively the logic filters the signal from the heartbeat waveform sensor.

The control logic used to implement the heartbeat waveform processing described herein typically, though not necessarily, located on the fitness monitoring device. It may be implemented as hardware, software, firmware, or any combination thereof. It may be said that the instructions are provided by "programming". Such programming is understood to include logic of any form including hard coded logic in digital signal processors and other devices which have specific algorithms implemented as hardware. Programming is also understood to include software or firmware instructions that may be executed on a general purpose processor. The data used by the control logic in executing the instructions described herein may be stored (e.g., buffered) by associated memory, registers, and the like, which may be entirely resident on the device or partially resident on a paired secondary device. Examples of suitable architectures for implementing the control logic are presented below with reference to, e.g., FIGS. 11A-G, 12A-C, 13A-B, and 14A-D.

In some embodiments, the control logic includes a processor, chip, card, or board, or a combination of these, which includes logic for performing one or more control functions. In some embodiments, instructions for controlling the heartbeat waveform sensor are stored on a memory device associated with the fitness monitoring device or are provided over a network. Examples of suitable memory devices include semiconductor memory, magnetic memory, optical memory, and the like. The computer program code for controlling the heartbeat waveform sensor can be written in any conventional computer readable programming language such as assembly language, C, and the like. Compiled object code or script is executed by a processor to perform the tasks identified in the program.

Duty Cycling in Heartbeat Waveform Sensors

Device power can be saved by duty cycling the heartbeat waveform sensor during regular activities. The power savings may be achieved by turning off a PPG sensor's light source and/or light detector, and by reducing operation of the signal processing algorithm. The processing logic may duty cycle the sensor light source to correspond with the duty cycle for processing data.

Based on the determined activity state, the heart rate logic determines how frequently to generate a new heart rate reading. When in an activity state associated with high physical activity, the logic may determine the heart rate frequently (e.g., every second). However, when not engaged in a strenuous physical activity, it generates a new heart rate reading less frequently. Since a heart rate estimate requires calculation of a power spectral density, which requires PPG data for a minimum duration (e.g., about 5-15 seconds of data), the duty cycle logic should ensure that the sensor is turned on for the minimum time. In some implementations, duty cycling may be implemented as follows:

1. Once sufficient samples are obtained to calculate a heart rate estimate, the sensor (light source and light detector) may be turned off until the next sample is requested.

2. In the case where the user is actively looking at the estimate on a screen, duty cycling may be turned off and the user sees instantaneous updates in heart rate.

3. If the user is engaged in physical activity like running or biking where high resolution (e.g., 1 second resolution) is desired, again duty cycling may be turned off.

4. When a user is not operating in a way requiring frequent updates, the device logic can switch back to low power mode and can measure heart rate at a low frequency, such as once per minute. Even when the logic does not receive input suggesting that the user is interested in receiving updates, infrequent heart rate measurements may be taken for use in long term trends (e.g., day long).

5. In certain implementations, a device employing duty cycling may reduce the power consumed by an LED light source by 75% and the power consumed by the signal processing algorithm by 90%.

Ambient Light and Skin Color

Ambient light and skin color may make it difficult to extract a user's heart rate from a PPG signal. The effect of ambient light may be reduced by subtracting a value of the received detected light signal when the PPG light source is off from the value of the received detected light signal when the PPG light source is on (assuming that both signals are obtained in close temporal proximity to each other).

The effect of skin color may be reduced by changing the intensity of the PPG light source, the wavelength of the light emitted from the light source, and/or by using the ratio or difference of received signal corresponding to two different wavelengths. Skin color may be determined by using user input (e.g. the user entering their skin color), an image of the person's face, etc., and may then subsequently be used to calibrate the algorithm, light source brightness, light source wavelength, and the receiver gain. The effect of skin color (and tightness with which the user is wearing the device) on the raw PPG signal may also be measured by sending in a signal of known amplitude to the light source(s) and then measuring the received signal from the photodetector(s). Such a signal may be sent for a prolonged period of time (so as to capture data through multiple expected heart beats) and then averaged to produce a steady-state data set that is not heart-rate dependent. This amplitude may then be compared to a set of values stored in a table to determine algorithm calibration, transmitter amplitude and the receiver gain.

Heart Rate Estimate Improvement Using Heuristics

After getting an initial estimate of the heart rate (e.g., by peak counting or a power spectral density estimation), it may be useful to apply bounds on the allowable rates for heart rate. These bounds may be optimized on a per-user basis since each user will have a unique heart rate profile. For example, the sedentary rate of each user may be estimated when they are stationary and this may be used as a lower bound when the user is walking. Similarly, half the frequency of walking as calculated from the pedometer may serve as a good lower bound for the expected heart rate.

The heart rate algorithm may be tailored for each user and may learn the heart rate profile of the user and adapt to the user's behaviors and/or characteristics so as to perform better with time. For example, the algorithm may set bounds on the heart rate expected during a particular physical activity or rate of walking based on historical data from that user. This may help provide better results when the heart rate data is corrupted by noise and/or motion artifacts.

HR Quality Metric

In another example embodiment, a signal quality metric of the heart rate/PPG signal may be used to provide a quantification of the accuracy/precision of the signal being generated. Depending on the values of this metric, the algorithm that determines what the user's heart rate (or other PPG-derived metric such as respiration) is may take certain actions, including asking the user to tighten the watch band, ignoring certain portions of collected heart-rate data (e.g., sections of data that have a low quality metric), and weighting certain portions of the heart-rate data (e.g., data with a higher quality metric may be weighted more heavily when the heart rate is being calculated).

In one embodiment, the signal quality metric may be derived as follows: make a scatter plot where the x-axis is time, and the y-axis is the frequency of a peak in the PPG signal at that given instant in time. An issue to be overcome using this strategy is that there may be multiple and/or zero peaks at a given instant in time. A best fit line captures the linear relationship in this scatter plot. A high quality signal should have a set of peaks that fit well to a line (in a short time span), whereas a bad signal will have a set of peaks that are not well described by a line. Therefore, the quality of the fit to the line provides a good metric for the quality of the PPG signal itself.

Sedentary, Sleep, and Active Classified Metrics

In yet another example embodiment, the biometric monitoring device may employ sensors to calculate heart rate variability when the device determines the user to be sedentary or asleep. Here, the biometric monitoring device may operate the sensors in a higher-rate sampling mode (relative to non-sedentary periods or periods of user activity that exceed a predetermined threshold) to calculate heart rate variability. The biometric monitoring device (or an external device) may employ heart rate variability as an indicator of cardiac health or stress.

Indeed, in some embodiments, the biometric monitoring device may measure and/or determine the user's stress level and/or cardiac health when the user is sedentary and/or asleep (for example, as detected and/or determined by the biometric monitoring device). Some embodiments of a biometric monitoring device of the present disclosure may determine the user's stress level, health state (e.g., risk, onset, or progression of fever or cold), and/or cardiac health using sensor data that is indicative of the heart rate variability, galvanic skin response, skin temperature, body temperature, and/or heart rate. In this way, processing circuitry of the biometric monitoring device may determine and/or track the user's "baseline" stress levels over time and/or cardiac "health" over time. In another embodiment, the device may measure a physiologic parameter of the user during one or more periods where the user is motionless (or the user's motion is below a predetermined threshold), such as when the user is sitting, lying down, asleep, or in a sleep stage (e.g., deep sleep). Such data may also be employed by the biometric monitoring device as a "baseline" for stress-related parameters, health-related parameters (e.g., risk or onset of fever or cold), cardiac health, heart rate variability, galvanic skin response, skin temperature, body temperature and/or heart rate.

Sleep Monitoring

In some embodiments, the biometric monitoring device may automatically detect or determine when the user is attempting to go to sleep, is entering sleep, is asleep, and/or is awoken from a period of sleep. In such embodiments, the biometric monitoring device may employ physiological sensors to acquire data and the data processing circuitry of the biometric monitoring device may correlate a combination of heart rate, heart rate variability, respiration rate, galvanic skin response, motion, skin temperature, and/or body temperature data collected from sensors of the biometric monitoring device to detect or determine if the user is attempting to go to sleep, is entering sleep, is asleep, and/or is awoken from a period of sleep. In response, the biometric monitoring device may, for example, acquire physiological data (of the types, and in the manners, as described herein) and/or determine physiological conditions of the user (of the types, and in the manners, as described herein). For example, a decrease or cessation of user motion combined with a reduction in user heart rate and/or a change in heart rate variability may indicate that the user has fallen asleep. Subsequent changes in heart rate variability and galvanic skin response may then be used by the biometric monitoring device to determine transitions of the user's sleep state between two or more stages of sleep (for example, into lighter and/or deeper stages of sleep). Motion by the user and/or an elevated heart rate and/or a change in heart rate variability may be used by the biometric monitoring device to determine that the user has awoken.

Real-time, windowed, or batch processing may be used to determine the transitions between wake, sleep, and sleep stages. For instance, a decrease in heart rate may be measured in a time window where the heart rate is elevated at the start of the window and reduced in the middle (and/or end) of the window. The awake and sleep stages may be classified by a hidden Markov model using changes in motion signal (e.g., decreasing motion intensity), heart rate, heart rate variability, skin temperature, galvanic skin response, and/or ambient light levels. The transition points may be determined through a changepoint algorithm (e.g., Bayesian changepoint analysis). The transition between awake and sleep may be determined by observing periods where the user's heart rate decreases over a predetermined time duration by at least a certain threshold but within a predetermined margin of the user's resting heart rate (that is observed as, for example, the minimum heart rate of the user while sleeping). Similarly, the transition between sleep and awake may be determined by observing an increase in the user's heart rate above a predetermined threshold of the user's resting heart rate.

In some embodiments, the biometric monitoring device may be one component of a system for monitoring sleep, where the system includes a secondary device configured to communicate with the biometric monitoring device and adapted to be placed near the sleeper (e.g., an alarm clock).

The secondary device may, in some implementations, have a shape and mechanical and/or magnetic interface to accept the biometric monitoring device for safe keeping, communication, and/or charging. However, the secondary device may also be generic to the biometric monitoring device, e.g., a smartphone that is not specifically designed to physically interface with the biometric monitoring device. The communication between the biometric monitoring device and the secondary device may be provided through wired communication interfaces or through wireless communication interfaces and protocols such as Bluetooth (including, for example, Bluetooth 4.0 and Bluetooth Low Energy protocols), RFID, NFC, or WLAN. The secondary device may include sensors to assist in sleep monitoring or environmental monitoring such as, for example, sensors that measure ambient light, noise and/or sound (e.g., to detect snoring), temperature, humidity, and air quality (pollen, dust, $CO_2$, etc.). In one embodiment, the secondary device may communicate with an external service such as www.fitbit.com or a server (e.g., a personal computer). Communication with the secondary device may be achieved through wired (e.g., Ethernet, USB) or wireless (e.g., WLAN, Bluetooth, RFID, NFC, cellular) circuitry and protocols to transfer data to and/or from the secondary device. The secondary device may also act as a relay to transfer data to and/or from the biometric monitoring device to and/or from an external service such as www.fitbit.com or other service (e.g., data such as news, social network updates, email, calendar notifications) or server (e.g., personal computer, mobile phone, tablet). Calculation of the user's sleep data may be performed on one or both devices or an external service (e.g., a cloud server) using data from one or both devices.

The secondary device may be equipped with a display to display data obtained by the secondary device or data transferred to it by the biometric monitoring device, the external service, or a combination of data from the biometric monitoring device, the secondary device, and/or the external service. For example, the secondary device may display data indicative of the user's heart rate, total steps for the day, activity and/or sleep goal achievement, the day's weather (measured by the secondary device or reported for a location by an external service), etc. In another example, the secondary device may display data related to the ranking of the user relative to other users, such as total weekly step count. In yet another embodiment, the biometric monitoring device may be equipped with a display to display data obtained by the biometric monitoring device, the secondary device, the external service, or a combination of the three sources. In embodiments where the first device is equipped with a wakeup alarm (e.g., vibramotor, speaker), the secondary device may act as a backup alarm (e.g., using an audio speaker). The secondary device may also have an interface (e.g., display and buttons or touch screen) to create, delete, modify, or enable alarms on the first and/or the secondary device.

Sensor-Based Standby Mode

In another embodiment, the biometric monitoring device may automatically detect or determine whether it is or is not attached to, disposed on, and/or being worn by a user. In response to detecting or determining that the biometric monitoring device is not attached to, disposed on, and/or being worn by a user, the biometric monitoring device (or selected portions thereof) may implement or be placed in a low power mode of operation—for example, the optical heartbeat waveform sensor and/or circuitry may be placed in a lower power or sleep mode. For example, in one embodiment, the biometric monitoring device may include one or more light detectors (photodiodes, phototransistors, etc.). If, at a given light intensity setting (for example, with respect to the light emitted by a light source that is part of the biometric monitoring device), one or more light detectors provides a low return signal, the biometric monitoring device may interpret the data as indicative of the device not being worn. Upon such a determination, the device may reduce its power consumption—for example, by "disabling" or adjusting the operating conditions of the stress and/or heart rate detection sensors and/or circuitry in addition to other device circuitry or displays (for example, by reducing the duty cycle of or disabling the light source(s) and/or detector(s), turning off the device display, and/or disabling or attenuating associated circuitry or portions thereof). In addition, the biometric monitoring device may periodically determine (e.g., once per second) if the operating conditions of the stress and/or heart rate detection sensors and/or associated circuitry should be restored to a normal operating condition (for example, light source(s), detector(s) and/or associated circuitry should return to a normal operating mode for heart rate detection). In another embodiment, the biometric monitoring device may restore the operating conditions of the stress and/or heart rate detection sensors and/or associated circuitry upon detection of a triggerable event—for example, upon detecting motion of the device (for example, based on data from one or more motion sensor(s)) and/or detecting a user input via the user interface (for example, a tap, bump or swipe interaction with the biometric monitoring device). In some related embodiments, the biometric monitoring device may, for power saving purposes, reduce its default rate of heart rate measurement collection to, for instance, one measurement per minute while the user is not highly active and the user may have the option of putting the device into a mode of operation to generate measurements on demand or at a faster rate (e.g., once per second), for instance, by pushing a button.

Optical Sensor(s)

In one embodiment, the optical sensors (sources and/or detectors) may be disposed on an interior or skin-side of the biometric monitoring device (i.e., a side of the biometric monitoring device that contacts, touches, and/or faces the skin of the user (hereinafter "skin-side"). (See, for example, FIGS. 2A through 3C). In another embodiment, the optical sensors may be disposed on one or more sides of the device, including the skin-side and one or more sides of the device that face or are exposed to the ambient environment (environmental side). (See, for example, FIGS. 6A through 7).

Figure 6A:
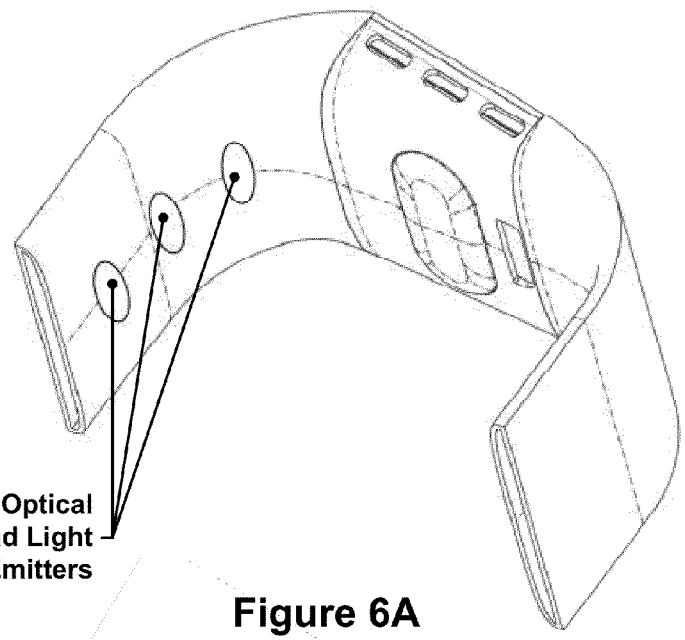
FIG. 6A illustrates an example of a portable monitoring device having a band; optical sensors and light emitters may be placed on the band.

FIG. 6A illustrates an example of a portable monitoring device having a band; optical sensors and light emitters may be placed on the band.

Figure 6B:
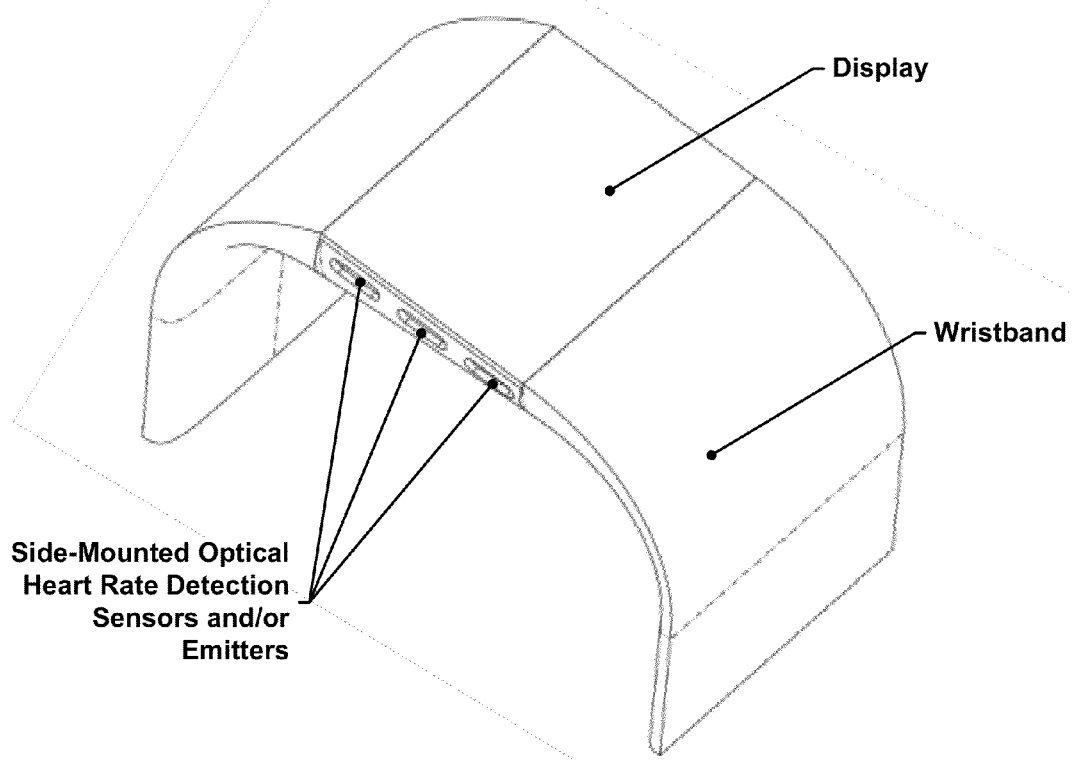
FIG. 6B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

FIG. 6B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

Figure 7:
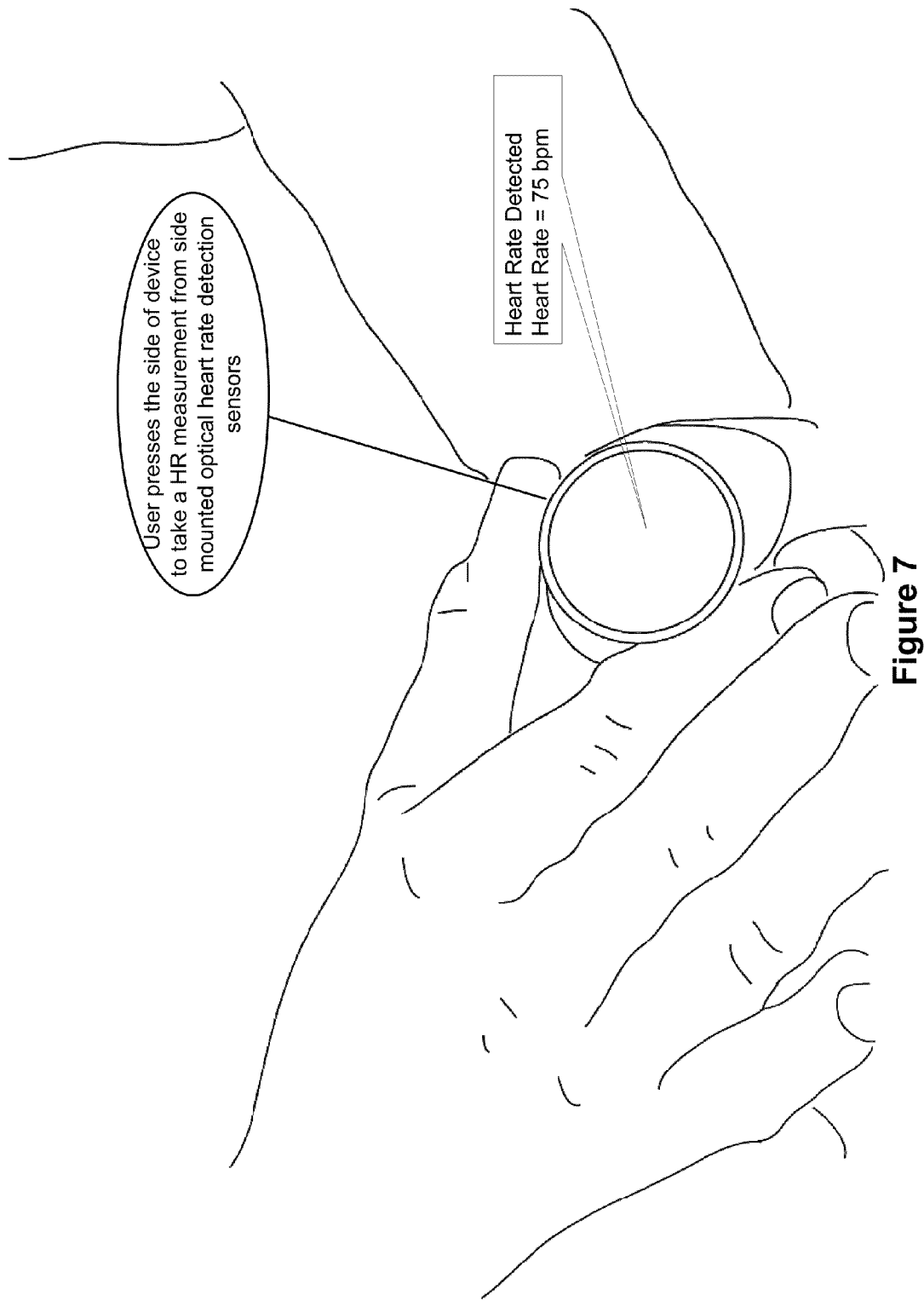
FIG. 7 depicts a user pressing the side of a portable biometric monitoring device to take a heart rate measurement from a side-mounted optical heart rate detection sensor. The display of the biometric monitoring device may show whether or not the heart rate has been detected and/or display the user's heart rate.

FIG. 7 depicts a user pressing the side of a portable biometric monitoring device to take a heart rate measurement from a side-mounted optical heart rate detection sensor. The display of the biometric monitoring device may show whether or not the heart rate has been detected and/or display the user's heart rate.

Notably, the data from such optical sensors may be representative of physiological data and/or environmental data. Indeed, in one embodiment, the optical sensors provide, acquire and/or detect information from multiple sides of the biometric monitoring device whether or not the sensors are disposed on one or more of the multiple sides. For example, the optical sensors may obtain data related to the ambient light conditions of the environment.

Where optical sensors are disposed or arranged on the skin-side of the biometric monitoring device, in operation, a light source in the biometric monitoring device may emit light upon the skin of the user and, in response, a light detector in the biometric monitoring device may sample, acquire, and/or detect corresponding reflected and/or emitted light from the skin (and from inside the body). The one or more light sources and light detectors may be arranged in an array or pattern that enhances or optimizes the signal-to-noise ratio and/or serves to reduce or minimize power consumption by the light sources and light detectors. These optical sensors may sample, acquire and/or detect physiological data which may then be processed or analyzed (for example, by resident processing circuitry) to obtain data that is representative of, for example, a user's heart rate, respiration, heart rate variability, oxygen saturation ($SpO_2$), blood volume, blood glucose, skin moisture, and/or skin pigmentation level.

The light source(s) may emit light having one or more wavelengths that are specific or directed to a type of physiological data to be collected. Similarly, the optical detectors may sample, measure and/or detect one or more wavelengths that are also specific or directed to a type of physiological data to be collected and/or a physiological parameter (of the user) to be assessed or determined. For instance, in one embodiment, a light source emitting light having a wavelength in the green spectrum (for example, an LED that emits light having wavelengths corresponding to the green spectrum) and a photodiode positioned to sample, measure, and/or detect a response or reflection corresponding with such light may provide data that may be used to determine or detect heart rate. In contrast, a light source emitting light having a wavelength in the red spectrum (for example, an LED that emits light having wavelengths corresponding to the red spectrum) and a light source emitting light having a wavelength in the infrared spectrum (for example, an LED that emits light having wavelengths corresponding to the IR spectrum) and photodiode positioned to sample, measure and/or detect a response or reflection of such light may provide data used to determine or detect $SpO_2$.

Indeed, in some embodiments, the color or wavelength of the light emitted by the light source, e.g., an LED (or set of LEDs), may be modified, adjusted, and/or controlled in accordance with a predetermined type of physiological data being acquired or conditions of operation. Here, the wavelength of the light emitted by the light source may be adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity. (See, for example, FIG. 11D).

The biometric monitoring device, in some embodiments, may include a window (for example, a window that is, to casual inspection, opaque) in the housing to facilitate optical transmission between the optical sensors and the user. Here, the window may permit light (for example, of a selected wavelength) to be emitted by, for example, one or more LEDs, onto the skin of the user and a response or reflection of that light to pass back through the window to be sampled, measured, and/or detected by, for example, one or more photodiodes. In one embodiment, the circuitry related to emitting and receiving light may be disposed in the interior of the device housing and underneath or behind a plastic or glass layer (for example, painted with infrared ink) or an infrared lens or filter that permits infrared light to pass but not light in the human visual spectrum. In this way, the light transmissivity of the window may be invisible to the human eye.

The biometric monitoring device may employ light pipes or other light-transmissive structures to facilitate transmission of light from the light sources to the user's body and skin. (See, for example, FIGS. 4A through 5). In this regard, in some embodiments, light may be directed from the light source to the skin of the user through such light pipes or other light-transmissive structures. Scattered light from the user's body may be directed back to the optical circuitry in the biometric monitoring device through the same or similar structures. Indeed, the light-transmissive structures may employ a material and/or optical design to facilitate low light loss (for example, the light-transmissive structures may include a lens to facilitate light collection, and portions of the light-transmissive structures may be coated with or adjacent to reflective materials to promote internal reflection of light within the light-transmissive structures) thereby improving the signal-to-noise-ratio of the photo detector and/or facilitating reduced power consumption of the light source(s) and/or light detectors. In some embodiments, the light pipes or other light-transmissive structures may include a material that selectively transmits light having one or more specific or predetermined wavelengths with higher efficiency than others, thereby acting as a bandpass filter. Such a bandpass filter may be tuned to improve the signal of a specific physiological data type. For example, in one embodiment, an In-Mold-Labeling or "IML" light-transmissive structure may be implemented wherein the light-transmissive structure uses a material with predetermined or desired optical characteristics to create a specific bandpass characteristic, for example, so as to pass infrared light with greater efficiency than light of other wavelengths (for example, light having a wavelength in human visible spectrum). In another embodiment, a biometric monitoring device may employ a light-transmissive structure having an optically opaque portion (including certain optical properties) and an optically-transparent portion (including optical properties different from the optically-opaque portion). Such a light-transmissive structure may be provided via a double-shot or two-step molding process wherein optically opaque material and optically transparent material are separately injected into a mold. A biometric monitoring device implementing such a light-transmissive structure may include different light transmissivity properties for different wavelengths depending on the direction of light travel through the light-transmissive structure. For example, in one embodiment, the optically-opaque material may be reflective to a specific wavelength range so as to more efficiently transport light from the user's body back to the light detector (which may be of a different wavelength(s) relative to the wavelength(s) of the emitted light).

In another embodiment, reflective structures may be placed in the field of view of the light emitter(s) and/or light detector(s). For example, the sides of holes that channel light from light emitter(s) to a user's skin and/or from the user's skin to light detector(s) (or through which light-transmissive structures that perform such channeling travel) may be covered in a reflective material (e.g., chromed) to facilitate light transmission. The reflective material may increase the efficiency with which the light is transported to the skin from the light source(s) and then from the skin back into the detector(s). The reflectively-coated hole may be filled in with an optical epoxy or other transparent material to prevent liquid from entering the device body while still allowing light to be transmitted with low transmission loss.

In another embodiment that implements light-transmissive structures (for example, structures created or formed through IML), such light-transmissive structures may include a mask consisting of an opaque material that limits the aperture of one, some, or all of the light source(s) and/or detector(s). In this way, the light-transmissive structures may selectively "define" a preferential volume of the user's body that light is emitted into and/or detected from. Notably, other mask configurations may be employed or implemented in connection with the concepts described and/or illustrated herein; all such masking configurations to, for example, improve the photoplethysmography signal and which are implemented in connection with the concepts described and/or illustrated herein are intended to fall within the scope of the present disclosure.

In another embodiment, the light emitter(s) and/or detector(s) may be configured to transmit light through a hole or series of holes in the device exterior. This hole or series of holes may be filled in with light-transmissive epoxy (e.g. optical epoxy). The epoxy may form a light pipe that allows light to be transmitted from the light emitter(s) to the skin and from the skin back into the light detector(s). This technique also has the advantage that the epoxy may form a watertight seal, preventing water, sweat or other liquid from entering the device body though the hole(s) on the device exterior that allow the light emitter(s) and detector(s) to transmit to, and receive light from, the biometric monitoring device body exterior. An epoxy with a high thermal conductivity may be used to help prevent the light source(s) (e.g., LED's) from overheating.

In any of the light-transmissive structures described herein, the exposed surfaces of the optics (light-transmissive structures) or device body may include a hard coat paint, hard coat dip, or optical coatings (such as anti-reflection, scratch resistance, anti-fog, and/or wavelength band block (such as ultraviolet light blocking) coatings). Such characteristics or materials may improve the operation, accuracy and/or longevity of the biometric monitoring device.

Figure 4A:
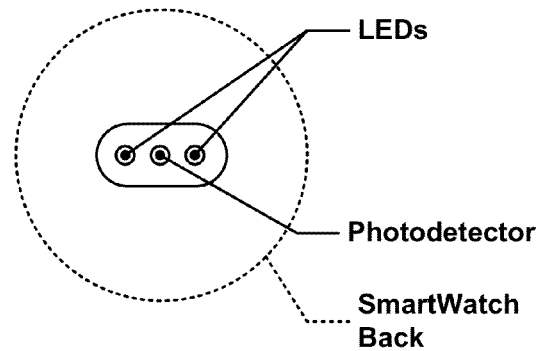
FIG. 4A illustrates an example of one potential PPG light source and photodetector geometry.

FIG. 4A illustrates an example of one potential PPG light source and photodetector geometry. In this embodiment, two light sources are placed on either side of a photodetector. These three devices are located in a protrusion on the back of a wristband-type biometric monitoring device (the side which faces the skin of the user).

Figure 4B:
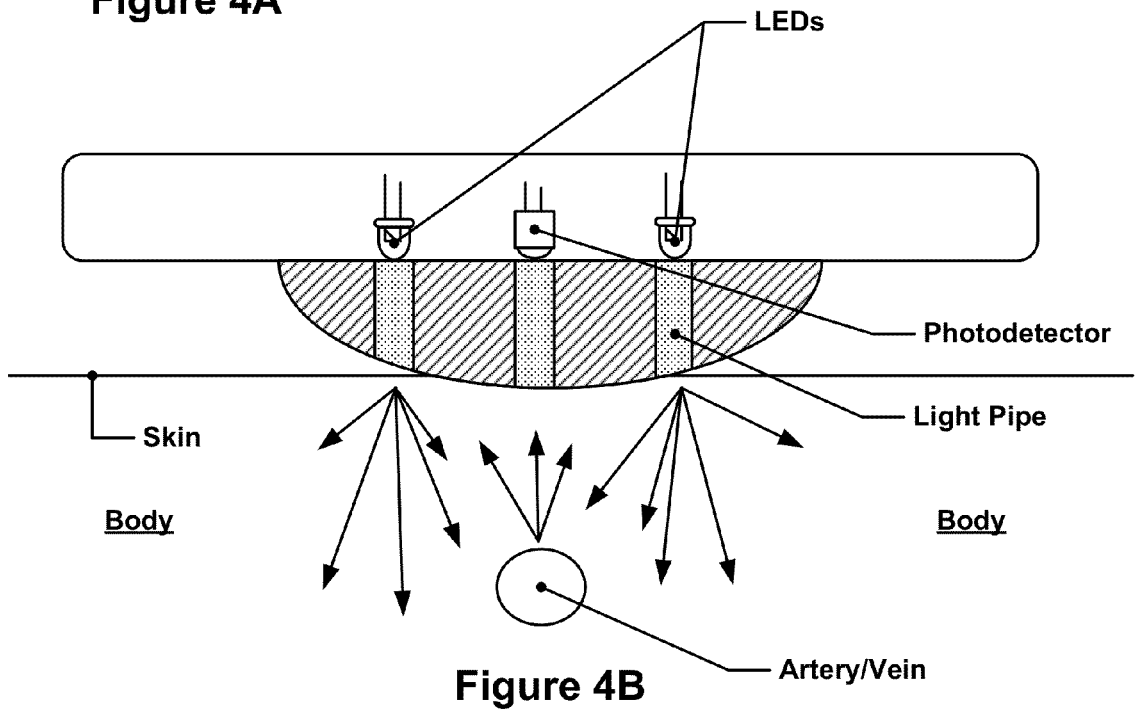
FIGS. 4B and 4C illustrate examples of a PPG sensor having a photodetector and two LED light sources.
Figure 4C:
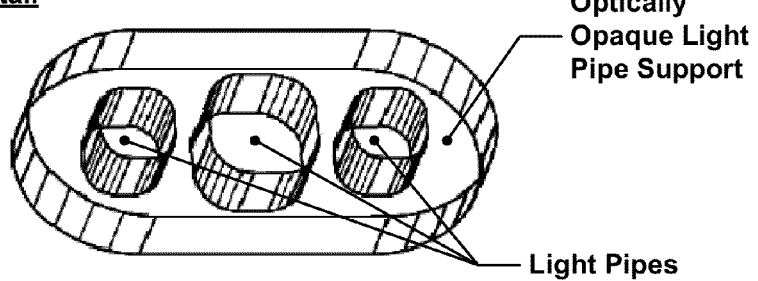

FIGS. 4B and 4C illustrate examples of a PPG sensor having a photodetector and two LED light sources. These components are placed in a biometric monitoring device that has a protrusion on the back side. Light pipes optically connect the LEDs and photodetector with the surface of the user's skin. Beneath the skin, the light from the light sources scatters off of blood in the body, some of which may be scattered or reflected back into the photodetector.

Figure 5:
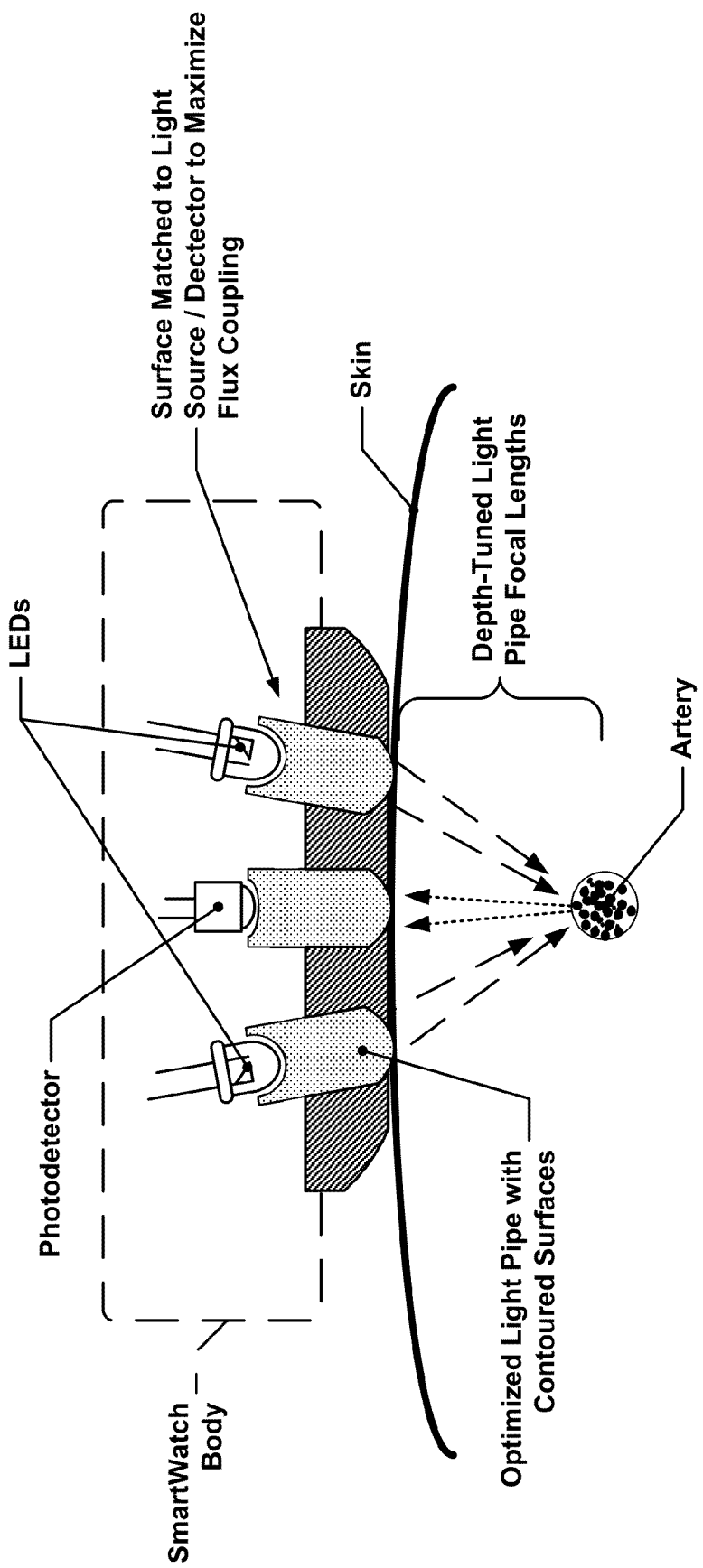
FIG. 5 Illustrates an example of an optimized PPG detector that has a protrusion with curved sides so as not to discomfort the user.

FIG. 5 Illustrates an example of a biometric monitoring device with an optimized PPG detector that has a protrusion with curved sides so as not to discomfort the user. Additionally, the surface of light pipes that optically couple the photodetector and the LEDs to the wearer's skin are contoured to maximize light flux coupling between the LEDs and photodetectors and the light pipes. The ends of the light pipes that face the user's skin are also contoured. This contour may focus or defocus light to optimize the PPG signal. For example, the contour may focus emitted light to a certain depth and location that coincides with an area where blood flow is likely to occur. The vertex of these foci may overlap or be very close together so that the photodetector receives the maximum possible amount of scattered light.

In some embodiments, the biometric monitoring device may include a concave or convex shape, e.g., a lens, on the skin-side of the device, to focus light towards a specific volume at a specific depth in the skin and increase the efficiency of light collected from that point into the photodetector. (See, for example, FIGS. 4A through 5). Where such a biometric monitoring device also employs light pipes to selectively and controllably route light, it may be advantageous to shape the end of the light pipe with a degree of cylindricity, e.g., the end of the light pipe may be a be a cylindrical surface (or portion thereof) defined by a cylinder axis that is nominally parallel to the skin-side (for example, rather than use an axially-symmetric lens). For example, in a wristband-style biometric monitoring device, such a cylindrical lens may be oriented such that the cylinder axis is nominally parallel to the wearer's forearm, which may have the effect of limiting the amount of light that enters such a lens from directions parallel to the person's forearm and increasing the amount of light that enters such a lens from directions perpendicular to the person's forearm—since ambient light is more likely to reach the sensor detection area from directions that are not occluded by the straps of the biometric monitoring device, i.e., along the user's forearm axis, than from directions that are occluded by the straps, i.e., perpendicular to the user's forearm. Such a configuration may improve the signal-to-noise-ratio by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's skin/body response to such emitted light (signal or data that is representative of the response to the emitted light).

In another embodiment, light-transmissive epoxy may be molded into a concave or convex shape so as to provide beneficial optical properties to sensors as well. For example, during the application of light transmissive epoxy, the top of the light-transmissive structure that is formed by the epoxy may be shaped into a concave surface so that light couples more effectively into the light-transmissive structure.

In one embodiment, the components of the optical sensor may be positioned on the skin-side of the device and arranged or positioned to reduce or minimize the distance between (i) the light source(s) and/or the associated detector(s) and (ii) the skin of the user. See, for example, FIG. 3A, which provides a cross-sectional view of a sensor protrusion of an example portable monitoring device. In FIG. 3A, two light sources (e.g., LEDs) are placed on either side of a photodetector to enable PPG sensing. A light-blocking material is placed between the light sources and the photodetector to prevent any light from the light sources from reaching photodetector without first exiting the body of the biometric monitoring device. A flexible transparent layer may be placed on the lower surface of the sensor protrusion to form a seal. This transparent layer may serve other functions such as preventing liquid from entering the device where the light sources or photodetectors are placed. This transparent layer may be formed through in-mold labeling or "IML". The light sources and photodetector may be placed on a flexible PCB.

Such a configuration may improve the efficiency of light flux coupling between the components of the optical sensor and the user's body. For example, in one embodiment, the light source(s) and/or associated detector(s) may be disposed on a flexible or pliable substrate that may flex, allowing the skin-side of the biometric monitoring device, which may be made from a compliant material, to conform (for example, without additional processing) or be capable of being shaped (or compliant) to conform to the shape of the body part (for example, the user's wrist, arm, ankle, and/or leg) to which the biometric monitoring device is coupled to or attached during normal operation so that the light source(s) and/or associated detector(s) are/is close to the skin of the user (i.e., with little to no gap between the skin-side of the device and the adjacent surface of the skin of the user. See, for example, FIG. 6A. In one embodiment, the light source(s) and/or associated detector(s) may be disposed on a Flat Flex Cable or "FFC" or flexible PCB. In this embodiment, the flexible or pliable substrate (for example, an FFC or flexible PCB) may connect to a second substrate (for example, PCB) within the device having other components disposed thereon (for example, the data processing circuitry). Optical components of differing heights may be mounted to different "fingers" of flexible substrate and pressed or secured to the housing surface such that the optical components are flush to the housing surface. In one embodiment, the second substrate may be a relatively inflexible or non-pliable substrate, fixed within the device, having other circuitry and components (passive and/or active) disposed thereon.

FIG. 3B depicts a cross-sectional view of a sensor protrusion of an example portable monitoring device; this protrusion is similar to that presented in FIG. 3A with the exception that the light sources and photodetector are placed on a flat and/or rigid PCB.

Figure 3C:
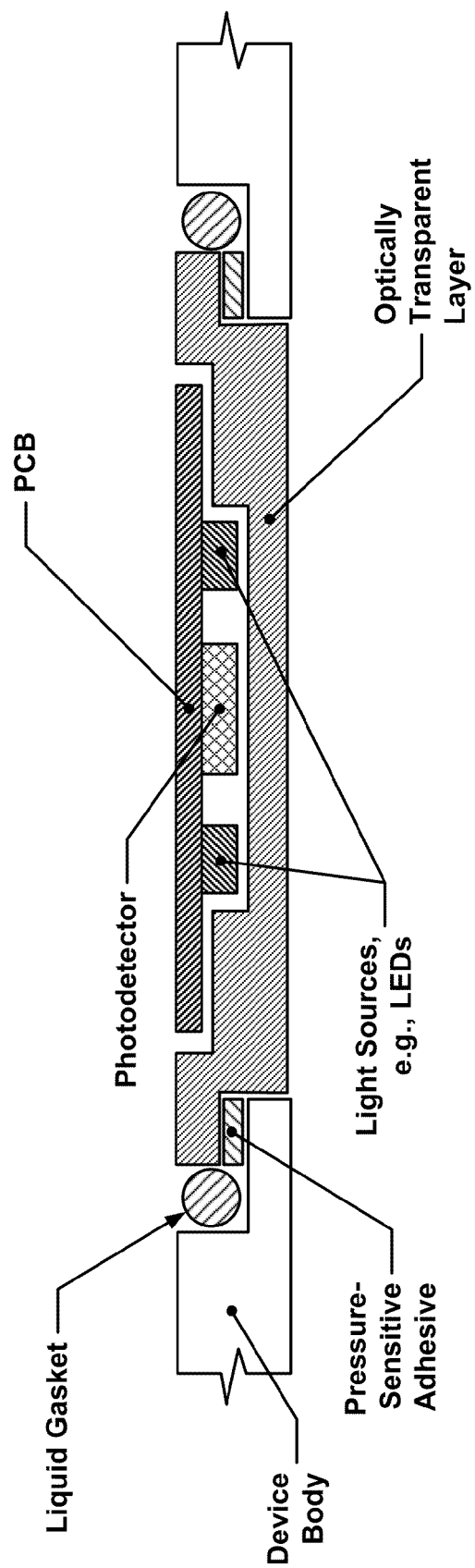
FIG. 3C provides another cross-sectional view of an example PPG sensor implementation.

FIG. 3C provides another cross-sectional view of an example PPG sensor implementation. Of note in this PPG sensor is the lack of a protrusion. Additionally, a liquid gasket and/or a pressure sensitive adhesive are used to prevent liquid from entering the biometric monitoring device body.

Some embodiments of biometric monitoring devices may be adapted to be worn or carried on the body of a user. In some embodiments including the optical heart rate monitor, the device may be a wrist-worn or arm-mounted accessory such as a watch or bracelet. (See, for example, FIGS. 2A through 7). In one embodiment, optical elements of the optical heart rate monitor may be located on the interior or skin-side of the biometric monitoring device, for example, facing the top of the wrist (i.e., the optical heart rate monitor may be adjacent to and facing the wrist) when the biometric monitoring device is worn on the wrist. (See, for example, FIGS. 2A through 3C).

In another embodiment, the optical heart rate monitor may be located on one or more external or environmental side surfaces of the biometric monitoring device. (See, for example, FIGS. 6B and 7). In such embodiments, the user may touch an optical window (behind which optical elements of the optical heart rate monitor are located) with a finger on the opposing hand to initiate a heart rate measurement (and/or other metrics related to heart rate such as heart rate variability) and/or collect data which may be used to determine the user's heart rate (and/or other metrics related to heart rate). (See, for example, FIG. 6B). In one embodiment, the biometric monitoring device may trigger or initiate the measurement(s) by detecting a (sudden) drop in incident light on the photodiode—for example, when the user's finger is placed over the optical window. In addition thereto, or in lieu thereof, a heart rate measurement (or other such metric) may be trigged by an IR-based proximity detector and/or capacitive touch/proximity detector (which may be separate from other detectors). Such IR-based proximity detector and/or capacitive touch/proximity detector may be disposed in or on and/or functionally, electrically and/or physically coupled to the optical window to detect or determine the presence of, for example, the user's finger.

In yet another embodiment, the biometric monitoring device may include a button that, when depressed, triggers or initiates heart rate measurement (and/or other metrics related to heart rate). The button may be disposed in close proximity to the optical window to facilitate the user pressing the button while the finger is disposed on the optical window. (See, for example, FIG. 7). In one embodiment, the optical window may be embedded in a push button. Thus, when the user presses the button, it may trigger a measurement of the finger that depresses the button. Indeed, the button may be given a shape and/or resistance to pressing that enhances or optimizes a pressure profile of the button against the finger to provide a high signal-to-noise-ratio during measurement or data acquisition. In other embodiments (not illustrated), the biometric monitoring device may take the form of a clip, a smooth object, a pendant, an anklet, a belt, etc. that is adapted to be worn on the body, clipped or mounted to an article of clothing, deposited in clothing (e.g., in a pocket), or deposited in an accessory (e.g., handbag).

In one specific embodiment, the biometric monitoring device may include a protrusion on the skin- or interior side of the device. (See, FIGS. 2A through 6A). When coupled to the user, the protrusion may engage the skin with more force than the surrounding device body. In this embodiment, an optical window or light transmissive structure (both of which are discussed in detail above) may form or be incorporated in a portion of the protrusion. The light emitter(s) and/or detector(s) of the optical sensor may be disposed or arranged in the protrusion near the window or light transmissive structure. (See, for example, FIGS. 2B and 6A). As such, when attached to the user's body, the window portion of the protrusion of the biometric monitoring device may engage the user's skin with more force than the surrounding device body—thereby providing a more secure physical coupling between the user's skin and the optical window. That is, the protrusion may cause sustained contact between the biometric monitoring device and the user's skin that may reduce the amount of stray light measured by the photodetector, decrease relative motion between the biometric monitoring device and the user, and/or provide improved local pressure to the user's skin; all of which may increase the quality of the cardiac signal of interest. Notably, the protrusion may contain other sensors that benefit from close proximity and/or secure contact to the user's skin. These may be included in addition to or in lieu of a heartbeat waveform sensor and include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

In addition thereto, or in lieu thereof, a portion of the skin-side of the biometric monitoring device may include a friction enhancing mechanism or material. For example, the skin-side of the biometric monitoring device may include a plurality of raised or depressed regions or portions (for example, small bumps, ridges, grooves, and/or divots). Moreover, a friction enhancing material (for example, a gel-like material such as silicone or other elastomeric material) may be disposed on the skin-side. Indeed, a device back made out of gel may also provide friction while also improving user comfort and preventing stray light from entering. As noted above, a friction-enhancing mechanism or material may be used alone or in conjunction with the biometric monitoring device having a protrusion as described herein. In this regard, the biometric monitoring device may include a plurality of raised or depressed regions or portions (for example, small bumps, ridges, grooves, and/or divots) in or on the protrusion portion of the device. Indeed, such raised or depressed regions or portions may be incorporated/embedded into or on a window portion of the protrusion. In addition thereto, or in lieu thereof, the protrusion portion may consist of or be coated with a friction enhancing material (for example, a gel-like material such as silicone). Notably, the use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motion of the biometric monitoring device (and thus of the sensor) relative to the user's skin during operation, especially while the user is in motion.

Some or all of the interior or skin-side housing of the biometric monitoring device may also consist of a metal material (for example, steel, stainless steel, aluminum, magnesium, or titanium). Such a configuration may provide a structural rigidity. (See, for example, FIG. 2B). In such an embodiment, the device body may be designed to be hypoallergenic through the use of a hypoallergenic "nickel-free" stainless steel. Notably, it may be advantageous to employ (at least in certain locations) a type of metal that is at least somewhat ferrous (for example, a grade of stainless steel that is ferrous). In such embodiments, the biometric monitoring device (where it includes a rechargeable energy source (for example, rechargeable battery)) may interconnect with a charger via a connector that secures itself to the biometric monitoring device using magnets that couple to the ferrous material. In addition, biometric monitoring device may also engage a dock or dock station, using such magnetic properties, to facilitate data transfer. Moreover, such a housing may provide enhanced electromagnetic shielding that would enhance the integrity and reliability of the optical heartbeat waveform sensor and the heart rate data acquisition process/operation. Furthermore, a skin temperature sensor may be physically and thermally coupled, for example, with thermal epoxy, to the metal body to sense the temperature of the user. In embodiments including a protrusion, the sensor may be positioned near or in the protrusion to provide secure contact and localized thermal coupling to the user's skin.

In a preferred embodiment, one or more components of the optical sensor (which may, in one embodiment, be located in a protrusion, and/or in another embodiment, may be disposed or placed flush to the surface of the biometric monitoring device) are attached, fixed, included, and/or secured to the biometric monitoring device via a liquid-tight seal (i.e., a method/mechanism that prevents liquid ingress into the body of the biometric monitoring device). For example, in one embodiment, a device back made out of a metal such as, but not limited to, stainless steel, aluminum, magnesium, or titanium, or from a rigid plastic may provide a structure that is stiff enough to maintain the structural integrity of the device while accommodating a watertight seal for the sensor package. (See, for example, FIGS. 2B through 3C).

In a preferred embodiment, a package or module of the optical sensor may be connected to the device with a pressure-sensitive adhesive and a liquid gasket. See, for example, FIG. 3C, which provides another cross-sectional view of a PPG sensor implementation. Of note in this PPG sensor is the lack of a protrusion. Additionally, a liquid gasket and/or a pressure sensitive adhesive are used to prevent liquid from entering the device body. Screws, rivets or the like may also be used, for example, if a stronger or more durable connection is required between the optical sensor package/module and the device body. Notably, the present embodiments may also use watertight glues, hydrophobic membranes such as Gore-Tex, o-rings, sealant, grease, or epoxy to secure or attach the optical sensor package/module to the biometric monitoring device body.

As discussed above, the biometric monitoring device may include a material disposed on the skin- or interior side that includes high reflectivity characteristics—for example, polished stainless steel, reflective paint, and polished plastic. In this way, light scattered off the skin-side of the device may be reflected back into the skin in order to, for example, improve the signal-to-noise-ratio of an optical heartbeat waveform sensor. Indeed, this effectively increases the input light signal as compared with a device body back that is non-reflective (or less reflective). Notably, in one embodiment, the color of the skin or interior side of the biometric monitoring device may be selected to provide certain optical characteristics (for example, reflect certain or predetermined wavelengths of light), in order to improve the signal with respect to certain physiological data types. For example, where the skin- or interior side of the biometric monitoring device is green, the measurements of the heart rate may be enhanced due to the preferential emission of a wavelength of the light corresponding to the green spectrum. Where the skin- or interior side of the biometric monitoring device is red, the measurements of the SpO2 may be enhanced due to the preferential emission of a wavelength of the light corresponding to the red spectrum. In one embodiment, the color of the skin- or interior side of the biometric monitoring device may be modified, adjusted and/or controlled in accordance with a predetermined type of physiological data being acquired.

Figure 11A:
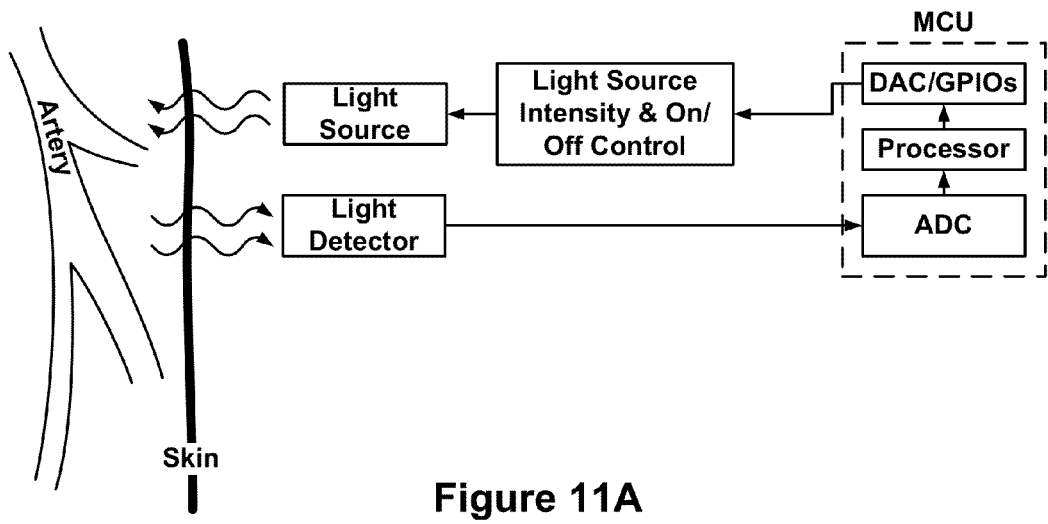
FIG. 11A illustrates an example block diagram of a PPG sensor which has a light source, light detector, ADC, processor, DAC/GPIOs, and light source intensity and on/off control.
Figure 11B:
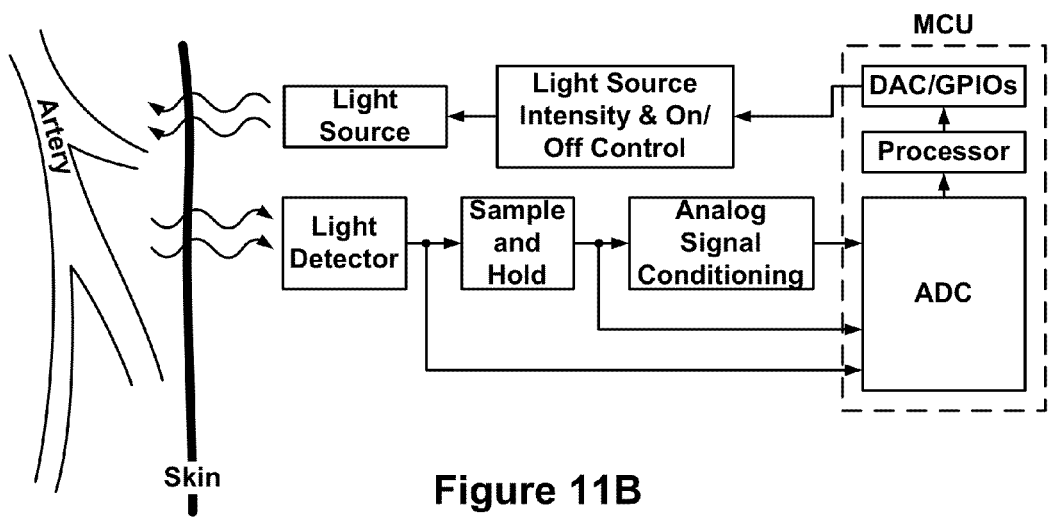
FIG. 11B illustrates an example block diagram of a PPG sensor that is similar to that of FIG. 11A which additionally uses a sample-and-hold circuit as well as analog signal conditioning.
Figure 11C:
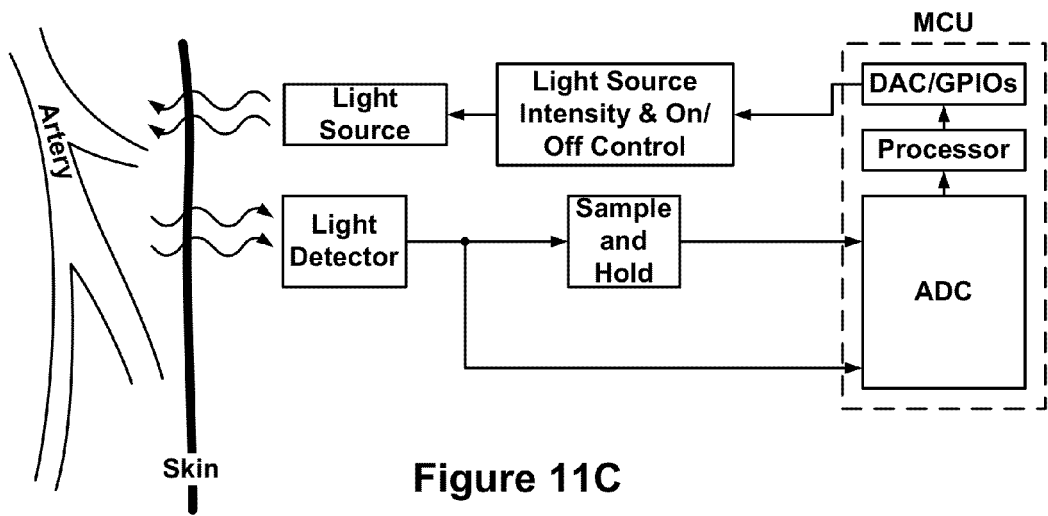
FIG. 11C illustrates an example block diagram of a PPG sensor that is similar to that of FIG. 11A which additionally uses a sample-and-hold circuit.
Figure 11D:
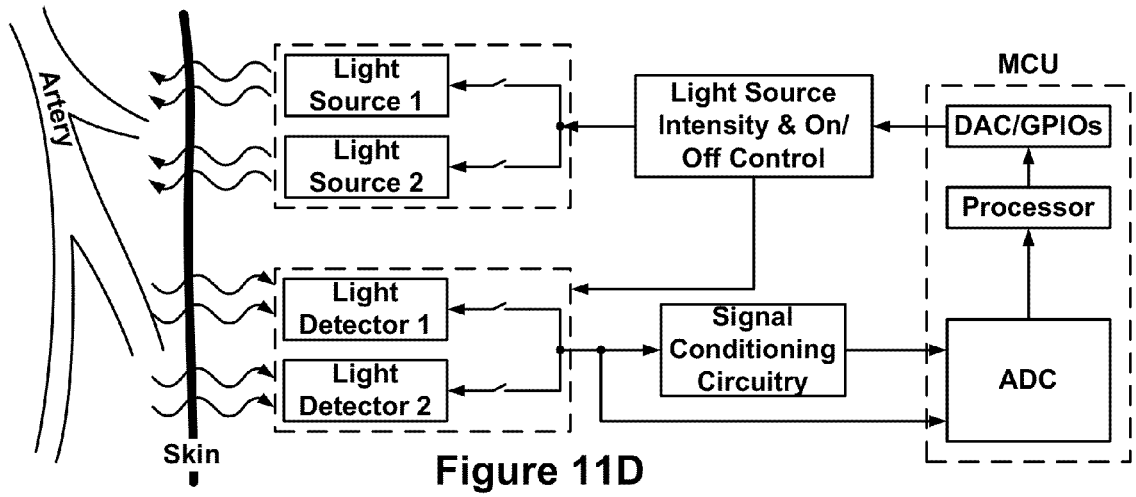
FIG. 11D illustrates an example block diagram of a a PPG sensor having multiple switchable light sources and detectors, light source intensity/on and off control, and signal conditioning circuitry.
Figure 11E:
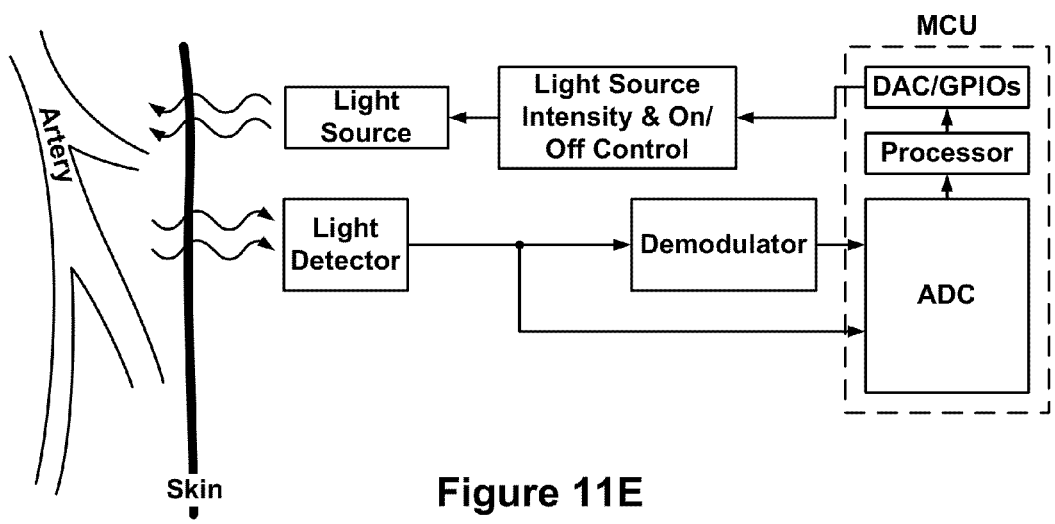
FIG. 11E illustrates an example block diagram of a PPG sensor which uses synchronous detection. To perform this type of PPG detection, it has a demodulator.
Figure 11F:
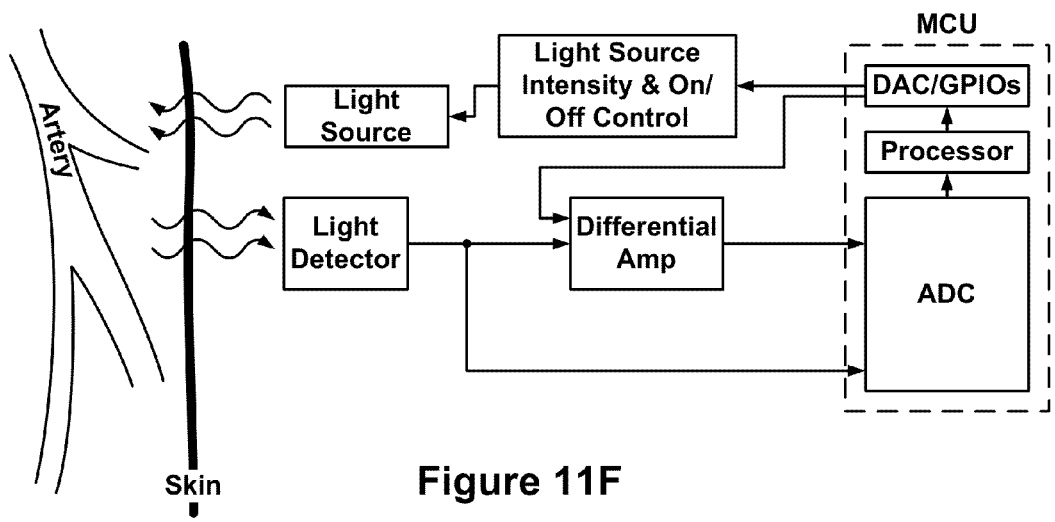
FIG. 11F illustrates an example block diagram of a PPG sensor which, in addition to the features of the sensor illustrated in FIG. 11A, has a differential amplifier.
Figure 11G:
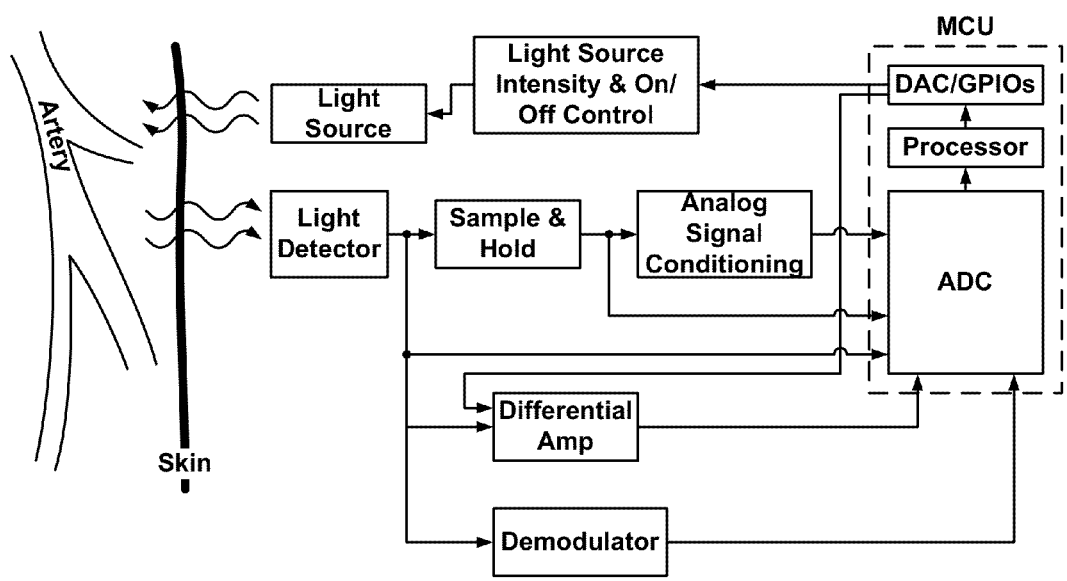
FIG. 11G illustrates an example block diagram of a PPG sensor which has the features of the PPG sensors shown in FIGS. 11A-KKF.

FIG. 11A depicts an example schematic block diagram of an optical heartbeat waveform sensor where light is emitted from a light source toward the user's skin and the reflection of such light from the skin/internal body of the user is sensed by a light detector, the signal from which is subsequently digitized by an analog to digital converter (ADC). The intensity of the light source may be modified (e.g., through a light source intensity control module) to maintain a desirable reflected signal intensity. For example, the light source intensity may be reduced to avoid saturation of the output signal from the light detector. As another example, the light source intensity may be increased to maintain the output signal from the light detector within a desired range of output values. Notably, active control of the system may be achieved through linear or nonlinear control methods such as proportional-integral-derivative (PID) control, fixed step control, predictive control, neural networks, hysteresis, and the like, and may also employ information derived from other sensors in the device such as motion, galvanic skin response, etc. FIG. 11A is provided for illustration and does not limit the implementation of such a system to, for instance, an ADC integrated within a MCU, or the use of a MCU for that matter. Other possible implementations include the use of one or more internal or external ADCs, FPGAs, ASICs, etc.

In another embodiment, system with an optical heartbeat waveform sensor may incorporate the use of a sample-and-hold circuit (or equivalent) to maintain the output of the light detector while the light source is turned off or attenuated to save power. In embodiments where relative changes in the light detector output are of primary importance (e.g., heart rate measurement), the sample-and-hold circuit may not have to maintain an accurate copy of the output of the light detector. In such cases, the sample-and-hold may be reduced to, for example, a diode (e.g., Schottky diode) and capacitor. The output of the sample-and-hold circuit may be presented to an analog signal conditioning circuit (e.g., a Sallen-Key bandpass filter, level shifter, and/or gain circuit) to condition and amplify the signal within frequency bands of interest (e.g., 0.1 Hz to 10 Hz for cardiac or respiratory function), which may then be digitized by the ADC. See, for example, FIG. 11B.

In operation, circuit topologies such as those already described herein (e.g. a sample-and-hold circuit) remove the DC and low frequency components of the signal and help resolve the AC component related to heart rate and/or respiration. The embodiment may also include the analog signal conditioning circuitry for variable gain settings that can be controlled to provide a suitable signal (e.g., not saturated). The performance characteristics (e.g., slew rate and/or gain bandwidth product) and power consumption of the light source, light detector, and/or sample-and-hold may be significantly higher than the analog signal conditioning circuit to enable fast duty cycling of the light source. In some embodiments, the power provided to the light source and light detector may be controlled separately from the power provided to the analog signal conditioning circuit to provide additional power savings. Alternatively or additionally, the circuitry can use functionality such as an enable, disable and/or shutdown to achieve power savings. In another embodiment, the output of the light detector and/or sample-and-hold circuit may be sampled by an ADC in addition to or in lieu of the analog signal conditioning circuit to control the light intensity of the light source or to measure the physiologic parameters of interest when, for example, the analog signal conditioning circuit is not yet stable after a change to the light intensity setting. Notably, because the physiologic signal of interest is typically small relative to the inherent resolution of the ADC, in some embodiments, the reference voltages and/or gain of the ADC may be adjusted to enhance signal quality and/or the ADC may be oversampled. In yet another embodiment, the device may digitize the output of only the sample-and-hold circuit by, for example, oversampling, adjusting the reference voltages and/or gain of the ADC, or using a high resolution ADC. See, for example, FIG. 11C.

PPG DC Offset Removal Techniques

In another embodiment, the sensor device may incorporate a differential amplifier to amplify the relative changes in the output of the light detector. See, for example, FIG. 11F. In some embodiments, a digital average or digital low-pass filtered signal may be subtracted from the output of the light detector. This modified signal may then be amplified before it is digitized by the ADC. In another embodiment, an analog average or analog low-pass filtered signal may be subtracted from the output of the light detector through, for example, the use of a sample-and-hold circuit and analog signal conditioning circuitry. The power provided to the light source, light detector, and differential amplifier may be controlled separately from the power provided to the analog signal conditioning circuit to improve power savings.

In another embodiment, a signal (voltage or current, depending on the specific sensor implementation) may be subtracted from the raw PPG signal to remove any bias in the raw PPG signal and therefore increase the gain or amplification of the PPG signal that contains heart rate (or other circulatory parameters such as heart rate variability) information. This signal may be set to a default value in the factory, to a value based on the user's specific skin reflectivity, absorption, and/or color, and/or may change depending on feedback from an ambient light sensor, or depending on analytics of the PPG signal itself. For example, if the PPG signal is determined to have a large DC offset, a constant voltage may be subtracted from the PPG signal to remove the DC offset and enable a larger gain, therefore improving the PPG signal quality. The DC offset in this example may result from ambient light (for example from the sun or from indoor lighting) reaching the photodetector from or reflected light from the PPG light source.

In another embodiment, a differential amplifier may be used to measure the difference between current and previous samples rather than the magnitude of each signal. Since the magnitude of each sample is typically much greater than the difference between each sample, a larger gain can be applied to each measurement, therefore improving the PPG signal quality. The signal may then be integrated to obtain the original time domain signal.

In another embodiment, the light detector module may incorporate a transimpedance amplifier stage with variable gain. Such a configuration may avoid or minimize saturation from bright ambient light and/or bright emitted light from the light source. For example, the gain of the transimpedance amplifier may be automatically reduced with a variable resistor and/or multiplexed set of resistors in the negative feedback path of the transimpedance amplifier. In some embodiments, the device may incorporate little to no optical shielding from ambient light by amplitude-modulating the intensity of the light source and then demodulating the output of the light detector (e.g., synchronous detection). See, for instance, FIG. 11E. In other aspects, if the ambient light is of sufficient brightness to obtain a heart rate signal, the light source may be reduced in brightness and/or turned off completely.

In yet another embodiment, the aforementioned processing techniques may be used in combination to optically measure physiological parameters of the user. See, for example, FIG. 11G. This topology may allow the system to operate in a low power measurement state and circuit topology when applicable and adapt to a higher power measurement state and circuit topology as necessary. For instance, the system may measure the physiologic parameter (e.g., heart rate) of interest using analog signal-conditioning circuitry while the user is immobile or sedentary to reduce power consumption, but switch to oversampled sampling of the light detector output directly while the user is active.

In embodiments where the biometric monitoring device includes a heart rate monitor, processing of the signal to obtain heart rate measurements may include filtering and/or signal conditioning such as band-pass filtering (e.g., Butterworth filter). To counteract large transients that may occur in the signal and/or to improve convergence of said filtering, nonlinear approaches may be employed such as neural networks or slew rate limiting. Data from the sensors on the device such as motion, galvanic skin response, skin temperature, etc., may be used to adjust the signal conditioning methods employed. Under certain operating conditions, the heart rate of the user may be measured by counting the number of signal peaks within a time window or by utilizing the fundamental frequency or second harmonic of the signal (e.g., through a fast Fourier transform (FFT)). In other cases, such as heart rate data acquired while the user is in motion, FFTs may be performed on the signal and spectral peaks extracted, which may then be subsequently processed by a multiple-target tracker which starts, continues, merges, and deletes tracks of the spectra. In some embodiments, a similar set of operations may be performed on the motion signal and the output may be used to do activity discrimination (e.g., sedentary, walking, running, sleeping, lying down, sitting, biking, typing, elliptical, weight training) which is used to assist the multiple-target tracker. For instance, it may be determined that the user was stationary and has begun to move. This information may be used to preferentially bias the track continuation toward increasing frequencies. Similarly, the activity discriminator may determine that the user has stopped running or is running slower and this information may be used to preferentially bias the track continuation toward decreasing frequencies. Tracking may be achieved with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc. A track selector module may use the output tracks from the multiple-spectra tracker and estimate the user's heart rate. The estimate may be taken as the maximum likelihood track, a weight sum of the tracks against their probabilities of being the heart rate, etc. The activity discriminator may furthermore influence the selection and/or fusion to get the heart rate estimate. For instance, if the user is sleeping, sitting, lying down, or sedentary, a prior probability may be skewed toward heart rates in the 40-80 bpm range; whereas if the user is running, jogging, or doing other vigorous exercise, a prior probability may be skewed toward elevated heart rates in the 90-180 bpm range. The influence of the activity discriminator may be based on the speed of the user. The estimate may be shifted toward (or wholly obtained by) the fundamental frequency of the signal when the user is not moving. The track that corresponds to the user's heart rate may be selected based on criteria that are indicative of changes in activity; for instance, if the user begins to walk from being stationary, the track that illustrates a shift toward higher frequency may be preferentially chosen.

The acquisition of a good heart rate signal may be indicated to the user through a display on the biometric monitoring device or another device in wired or wireless communication with the biometric monitoring device (e.g., a Bluetooth Low Energy-equipped mobile phone). In some embodiments, the biometric monitoring device may include a signal-strength indicator that is represented by the pulsing of an LED viewable by the user. The pulsing may be timed or correlated to be coincident with the user's heartbeat. The intensity, pulsing rate and/or color of the LED may be modified or adjusted to suggest signal strength. For example, a brighter LED intensity may represent a stronger signal or in an RGB LED configuration, a green colored LED may represent a stronger signal.

In some embodiments, the strength of the heart rate signal may be determined by the energy (e.g., squared sum) of the signal in a frequency band of, for instance, 0.5 Hz to 4 Hz. In other embodiments, the biometric monitoring device may have a strain gauge, pressure sensor, force sensor, or other contact-indicating sensor that may be incorporated or constructed into the housing and/or in the band (in those embodiments where the biometric monitoring device is attached to or mounted with a band like a watch, bracelet, and/or armband—which may then be secured to the user). A signal quality metric (e.g. heart rate signal quality) may be calculated based on data from these contact sensors either alone or in combination with data from the heart rate signal.

In another embodiment, the biometric monitoring device may monitor heart rate optically through an array of photodetectors such as a grid of photodiodes or a CCD camera. Motion of the optical device with respect to the skin may be tracked through feature-tracking of the skin and/or adaptive motion correction using an accelerometer and gyroscope. The detector array may be in contact with the skin or offset at a small distance away from the skin. The detector array and its associated optics may be actively controlled (e.g., with a motor) to maintain a stabilized image of the target and acquire a heart rate signal. This optomechanical stabilization may be achieved using information from motion sensors (e.g., a gyroscope) or image features. In one embodiment, the biometric monitoring device may implement relative motion cancellation using a coherent or incoherent light source to illuminate the skin and a photodetector array with each photodetector associated with comparators for comparing the intensity between neighboring detectors—obtaining a so-called speckle pattern which may be tracked using a variety of image tracking techniques such as optical flow, template matching, edge tracking, etc. In this embodiment, the light source used for motion tracking may be different than the light source used in the optical heart rate monitor.

In another embodiment, the biometric monitoring device may consist of a plurality of photodetectors and photoemitters distributed along a surface of the device that touches the user's skin (i.e., the skin-side of the biometric monitoring device). (See, for example, FIGS. 2A through 6A). In the example of a bracelet, for instance, there may be a plurality of photodetectors and photoemitters placed at various sites along the circumference of the interior of the band. (See, for example, FIG. 6A). A heart rate signal-quality metric associated with each site may be calculated to determine the best or set of best sites for estimating the user's heart rate. Subsequently, some of the sites may be disabled or turned off to, for example, reduce power consumption. The device may periodically check the heart rate signal quality at some or all of the sites to enhance, monitor and/or optimize signal and/or power efficiency.

In another embodiment, a biometric monitoring device may include a heart rate monitoring system including a plurality of sensors such as optical, acoustic, pressure, electrical (e.g., ECG or EKG), and motion and fuse the information from two or more of these sensors to provide an estimate of heart rate and/or mitigate noise induced from motion.

In addition to heart rate monitoring (or other biometric monitoring), or in lieu thereof, the biometric monitoring device, in some embodiments, may include optical sensors to track or detect time and duration of ultraviolet light exposure, total outdoor light exposure, the type of light source and duration and intensity of that light source (fluorescent light exposure, incandescent bulb light exposure, halogen, etc.), exposure to television (based on light type and flicker rate), whether the user is indoors or outdoors, time of day and location based on light conditions. In one embodiment, the ultraviolet detection sensor may consist of a reverse biased LED emitter driven as a light detector. The photocurrent produced by this detector may be characterized by, for instance, measuring the time it takes for the LED's capacitance (or alternately a parallel capacitor) to discharge.

All of the optical sensors discussed herein may be used in conjunction with other sensors to improve detection of the data described above or be used to augment detection of other types of physiological or environmental data.

Where the biometric monitoring device includes an audio or passive acoustic sensor, the device may contain one or more passive acoustic sensors that detect sound and pressure and that can include, but are not limited to, microphones, piezo films, etc. The acoustic sensors may be disposed on one or more sides of the device, including the side that touches or faces the skin (skin-side) and the sides that face the environment (environmental sides).

Skin-side acoustic or audio sensors may detect any type of sound transmitted through the body and such sensors may be arranged in an array or pattern that optimizes both the signal-to-noise-ratio and power consumption of such sensors. These sensors may detect respiration (e.g., by listening to the lung), respiratory sounds (e.g., breathing, snoring) and problems (e.g., sleep apnea, etc.), heart rate (listening to the heart beat), user's voice (via sound transmitted from the vocal cords throughout the body).

The biometric monitoring devices of the present disclosure may also include galvanic skin-response (GSR) circuitry to measure the response of the user's skin to emotional and physical stimuli or physiological changes (e.g., the transition of sleep stage). In some embodiments, the biometric monitoring device may be a wrist- or arm-mounted device incorporating a band made of conductive rubber or fabric so that the galvanic skin response electrodes may be hidden in the band. Because the galvanic skin response circuitry may be subjected to changing temperatures and environmental conditions, it may also include circuitry to enable automatic calibration, such as two or more switchable reference resistors in parallel or in series with the human skin/electrode path that allows real-time measurement of known resistors to characterize the response of the galvanic skin response circuit. The reference resistors may be switched into and out of the measurement path such that they are measured independently and/or simultaneously with the resistance of the human skin.

Circuits for Performing PPG

PPG circuitry may be optimized to obtain the best quality signal regardless of a variety of environmental conditions including, but not limited to, motion, ambient light, and skin color. The following circuits and techniques may be used to perform such optimization (see FIGS. 16A through 16J);

- a sample-and-hold circuit and differential/instrumentation amplifier which may be used in PPG sensing. The output signal is an amplified difference between current and previous sample, referenced to a given voltage.
- controlled current source to offset "bias" current prior to transimpedance amplifier. This allows greater gain to be applied at transimpedance amplifier stage.
- a sample-and-hold circuit for current feedback applied to photodiode (prior to transimpedance amplifier). This can be used for ambient light removal, or "bias" current removal, or as a pseudo differential amplifier (may require dual rails).
- a differential/instrumentation amplifier with ambient light cancellation.
- a photodiode offset current generated dynamically by a DAC.
- a photodiode offset current generated dynamically by controlled voltage source.
- ambient light removal using a "switched capacitor" method.
- photodiode offset current generated by a constant current source (also can be done with a constant voltage source and a resistor).
- ambient light removal and differencing between consecutive samples.
- ambient light removal and differencing between consecutive samples.

Figure 16A:
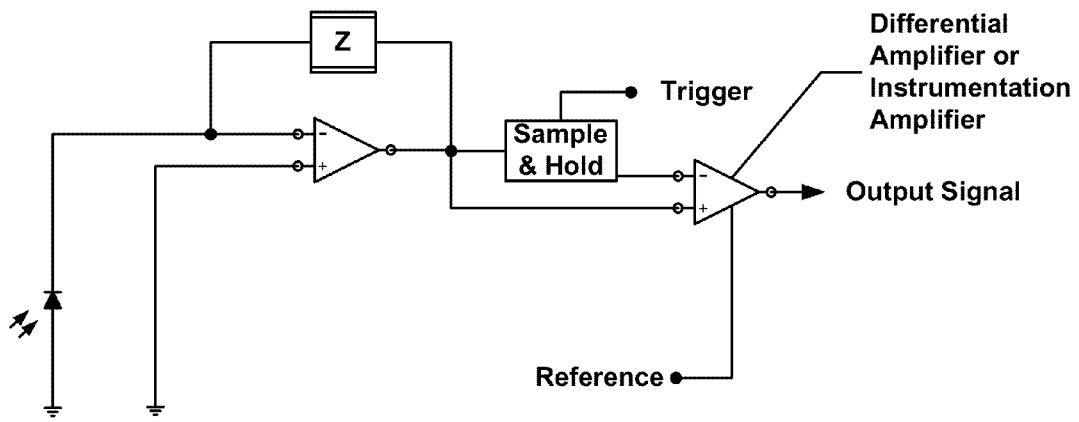
FIG. 16A illustrates an example schematic of a sample-and-hold circuit and differential/instrumentation amplifier which may be used in PPG sensing.

FIG. 16A illustrates an example schematic of a sample-and-hold circuit and differential/instrumentation amplifier which may be used in PPG sensing. The output signal in such a circuit may be an amplified difference between a current sample and a previous sample, referenced to a given voltage.

Figure 16B:
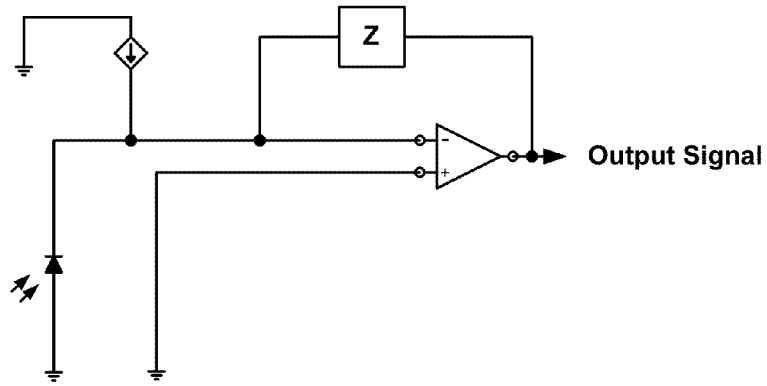
FIG. 16B illustrates an example schematic of a circuit for a PPG sensor using a controlled current source to offset "bias" current prior to a transimpedance amplifier

FIG. 16B illustrates an example schematic of a circuit for a PPG sensor using a controlled current source to offset "bias" current prior to a transimpedance amplifier. This allows greater gain to be applied at the transimpedance amplifier stage.

Figure 16C:
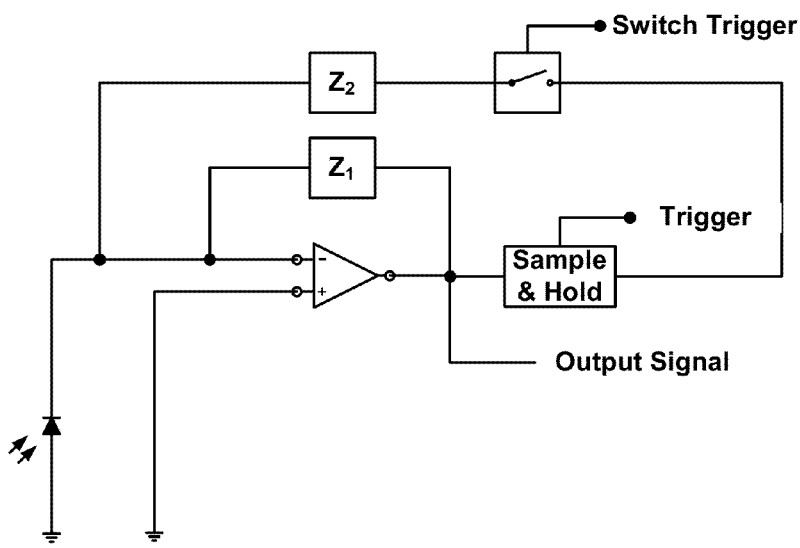
FIG. 16C illustrates an example schematic of a circuit for a PPG sensor using a sample-and-hold circuit for current feedback applied to photodiode (prior to a transimpedance amplifier).

FIG. 16C illustrates an example schematic of a circuit for a PPG sensor using a sample-and-hold circuit for current feedback applied to photodiode (prior to a transimpedance amplifier). This circuit may be used for ambient light removal, or "bias" current removal, or as a pseudo-differential amplifier.

Figure 16D:
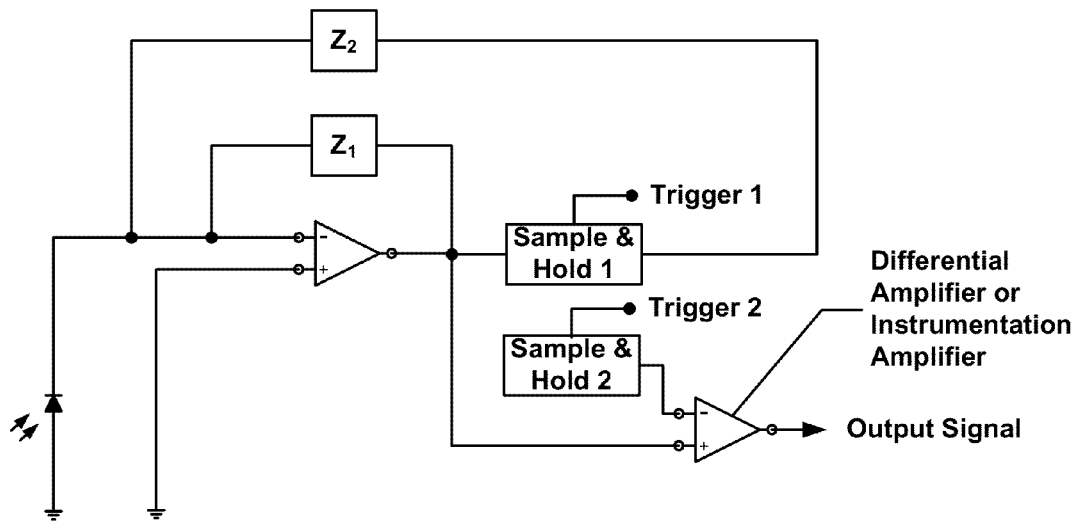
FIG. 16D illustrates an example schematic of a circuit for a PPG sensor using a differential/instrumentation amplifier with ambient light cancellation functionality.

FIG. 16D illustrates an example schematic of a circuit for a PPG sensor using a differential/instrumentation amplifier with ambient light cancellation functionality.

Figure 16E:
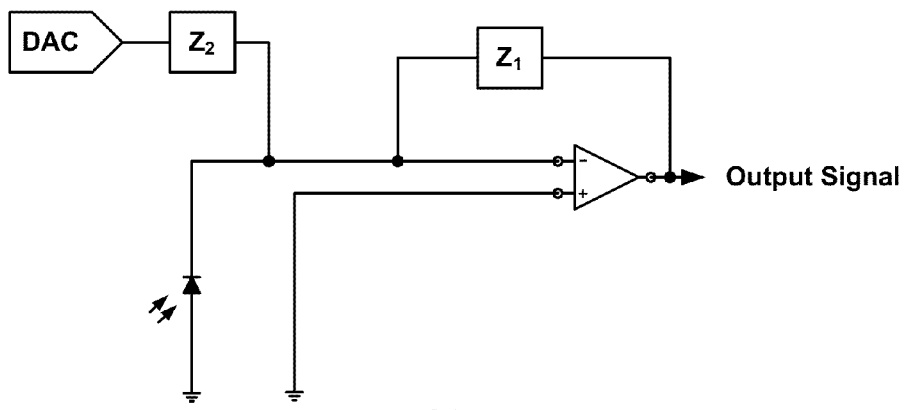
FIG. 16E illustrates an example schematic of a circuit for a PPG sensor using a photodiode offset current generated dynamically by a DAC.

FIG. 16E illustrates an example schematic of a circuit for a PPG sensor using a photodiode offset current generated dynamically by a DAC.

Figure 16F:
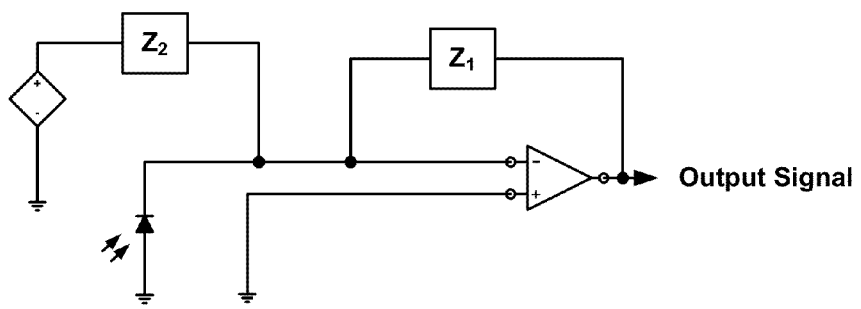
FIG. 16F illustrates an example schematic of a circuit for a PPG sensor using a photodiode offset current generated dynamically by a controlled voltage source.

FIG. 16F illustrates an example schematic of a circuit for a PPG sensor using a photodiode offset current generated dynamically by a controlled voltage source.

Figure 16G:
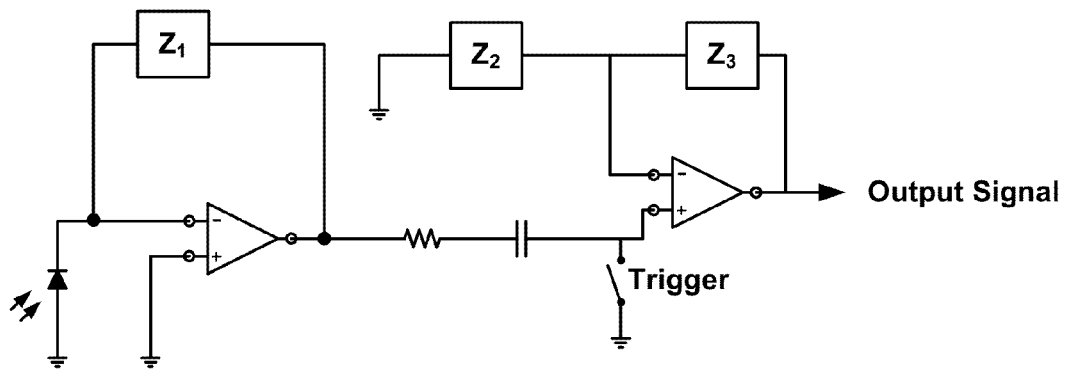
FIG. 16G illustrates an example schematic of a circuit for a PPG sensor including ambient light removal functionality using a "switched capacitor" method.

FIG. 16G illustrates an example schematic of a circuit for a PPG sensor including ambient light removal functionality using a "switched capacitor" method.

Figure 16H:
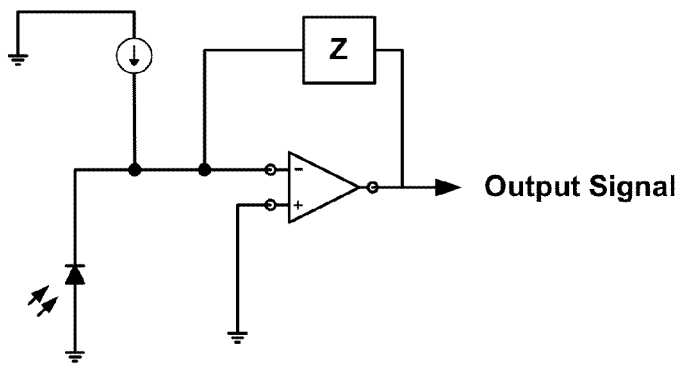
FIG. 16H illustrates an example schematic of a circuit for a PPG sensor that uses a photodiode offset current generated by a constant current source (this may also be done using a constant voltage source and a resistor).

FIG. 16H illustrates an example schematic of a circuit for a PPG sensor that uses a photodiode offset current generated by a constant current source (this may also be done using a constant voltage source and a resistor).

Figure 16I:
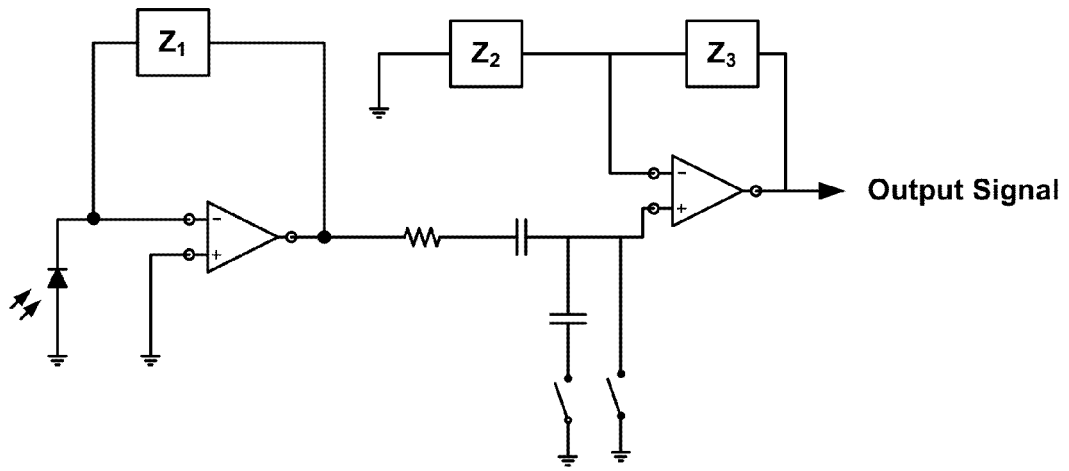
FIG. 16I illustrates an example schematic of a circuit for a PPG sensor that includes ambient light removal functionality and differencing between consecutive samples.

FIG. 16I illustrates an example schematic of a circuit for a PPG sensor that includes ambient light removal functionality and differencing between consecutive samples.

Figure 16J:
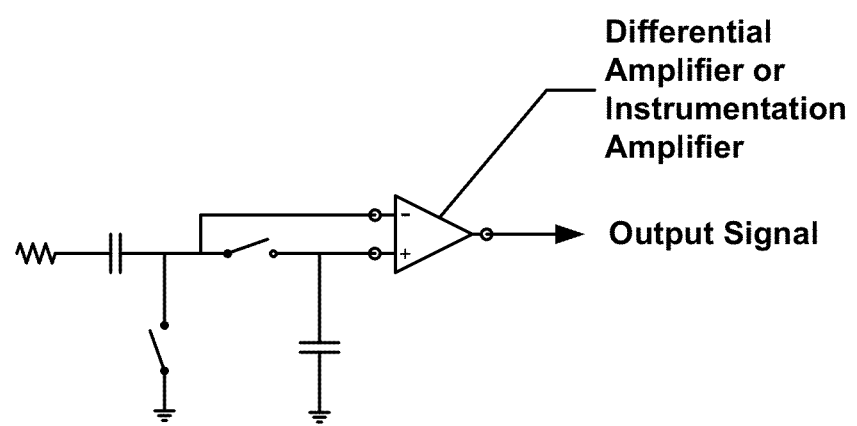
FIG. 16J illustrates an example schematic of a circuit for ambient light removal and differencing between consecutive samples.

FIG. 16J illustrates an example schematic of a circuit for ambient light removal and differencing between consecutive samples.

Various circuits and concepts related to heart rate measurement using a PPG sensor are discussed in more detail in U.S. Provisional Patent Application No. 61/946,439, filed Feb. 28, 2014, which was previously incorporated herein by reference in the "Cross-Reference to Related Applications" section and which is again hereby incorporated by reference with respect to content directed at heart rate measurements with a PPG sensor and at circuits, methods, and systems for performing such measurements, e.g., to compensate for sensor saturation, ambient light, and skin tone.

Biometric Feedback

Some embodiments of biometric monitoring devices may provide feedback to the user based on one or more biometric signals. In one embodiment, a PPG signal may be presented to the user as a real-time or near-real-time waveform on a display of the biometric monitoring device (or on a display of a secondary device in communication with the biometric monitoring device). This waveform may provide similar feedback to the waveform displayed on an ECG or EKG machine. In addition to providing the user with an indication of the PPG signal which may be used to estimate various heart metrics (e.g., heart rate), the waveform may also provide feedback that may enable the user to optimize the position and pressure with which they are wearing the biometric monitoring device. For example, the user may see that the waveform has a low amplitude. In response to this, the user may try moving the position of the biometric monitoring device to a different location which gives a higher amplitude signal. In some implementations, the biometric monitoring device may, based on such indications, provide instructions to the user to move or adjust the fit of the biometric monitoring device so as to improve the signal quality.

In another embodiment, feedback about the quality of the PPG signal may be provided to the user through a method other than displaying the waveform. The biometric monitoring device may emit an auditory alarm (e.g. a beep) if the signal quality (e.g. signal to noise ratio) exceeds a certain threshold. The biometric monitoring device may provide a visual cue (through the use of a display for example) to the user to either change the position of the sensor and/or increase the pressure with which the device is being worn (for example by tightening a wrist strap in the case that the device is worn on the wrist).

Biometric feedback may be provided for sensors other than PPG sensors. For example, if the device uses ECG, EMG, or is connected to a device which performs either of these, it may provide feedback to the user regarding the waveform from those sensors. If the signal-to-noise-ratio of these sensors is low, or the signal quality is otherwise compromised, the user may be instructed on how they can improve the signal. For example, if the heart rate cannot be detected from the ECG sensor, the device may provide a visual message to the user instructing them to wet or moisten the ECG electrodes to improve the signal.

Environmental Sensors

Some embodiments of biometric monitoring devices of the present disclosure may use one, some or all of the following environmental sensors to, for example, acquire the environmental data, including environmental data outlined in the table below. Such biometric monitoring devices are not limited to the number or types of sensors specified below but may employ other sensors that acquire environmental data outlined in the table below. All combinations and permutations of environmental sensors and/or environmental data are intended to fall within the scope of the present disclosure. Additionally, the device may derive environmental data from the corresponding sensor output data, but is not limited to the types of environmental data that it could derive from said sensor.

Notably, embodiments of biometric monitoring devices of the present disclosure may use one or more, or all of the environmental sensors described herein and one or more, or all of the physiological sensors described herein. Indeed, biometric monitoring device of the present disclosure may acquire any or all of the environmental data and physiological data described herein using any sensor now known or later developed—all of which are intended to fall within the scope of the present disclosure.

outside of the gel. The gel may act as a relatively impervious, incompressible, yet flexible, membrane that transmits external pressure variations to the altimeter while physically separating the altimeter (and other internal components) from the outside environment. The use of a gel-filled altimeter may give the device a higher level of environmental protection with or without the use of an environmentally sealed vent. The device may have a higher survivability rate with a gel-filled altimeter in locations including, but not limited to, locations that have high humidity, clothes washers, dish washers, clothes dryers, a steam room or sauna, a shower, a pool, a bath, and any location where the device may be exposed to moisture, exposed to liquid, or submerged in liquid.

Sensors integration/Signal Processing

Some embodiments of the biometric monitoring devices of the present disclosure may use data from two or more sensors to calculate the corresponding physiological or environmental data as seen in the table below (for example, data from two or more sensors may be used in combination to determine metrics such as those listed below). The biometric monitoring device may include, but is not limited to, the number, types, or combinations of sensors specified below. Additionally, such biometric monitoring devices may derive the included data from the corresponding sensor combinations, but are not limited to the number or types of data that may be calculated from the corresponding sensor combinations.

| Environmental Sensors | Environmental data acquired |
| --- | --- |
| Motion Detector<br>Potential Embodiments:<br>Inertial, Gyroscopic or Accelerometer-based Sensors<br>GPS | Location |
| Pressure/Altimeter sensor | Elevation |
| Ambient Temp | Temperature |
| Light Sensor | Indoor vs outdoor<br>Watching TV (spectrum/flicker rate detection)<br>Optical data transfer-initiation, QR codes, etc.<br>Ultraviolet light exposure |
| Audio | Indoor vs. Outdoor |
| Compass<br>Potential Embodiments:<br>3 Axis Compass | Location and/or orientation |

Figure 12C:
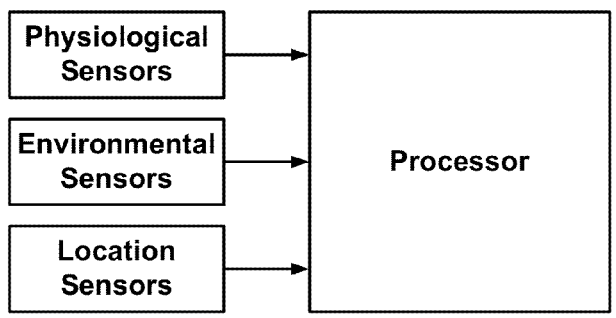
FIG. 12C illustrates an example of a portable biometric monitoring device having physiological sensors, environmental sensors, and location sensors connected to a processor.
Figure 13A:
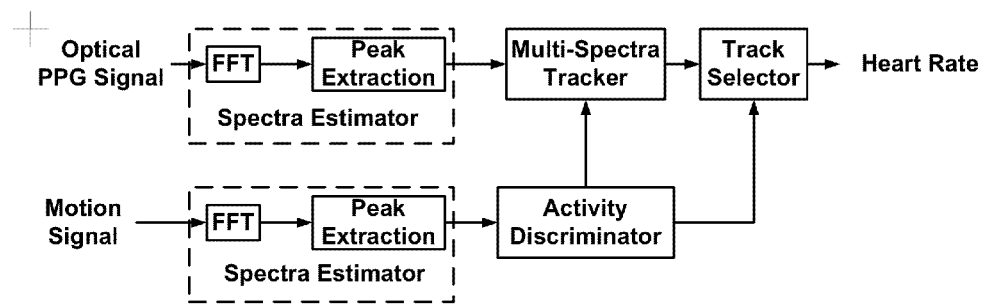
FIG. 13A illustrates an example of the use of a motion signal and an optical PPG signal to measure a heart rate.
Figure 13B:
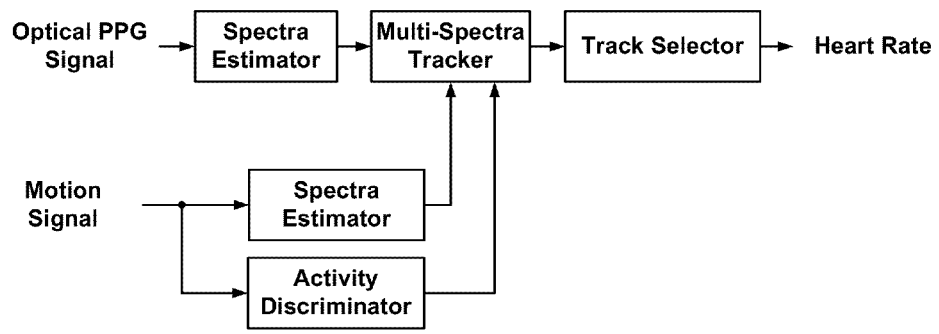
FIG. 13B illustrates another example of the use of a motion signal and an optical PPG signal to measure heart rate.
Figure 14A:
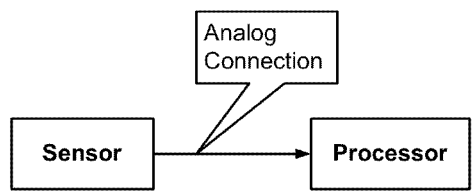
FIG. 14A illustrates an example of a sensor which has an analog connection to a sensor processor.
Figure 14B:
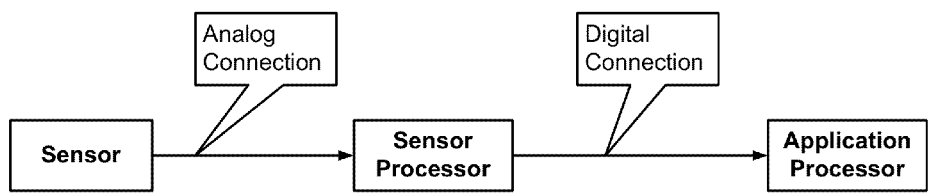
FIG. 14B illustrates an example of a sensor which has an analog connection to a sensor processor which, in turn, has a digital connection to an application processor.
Figure 14C:
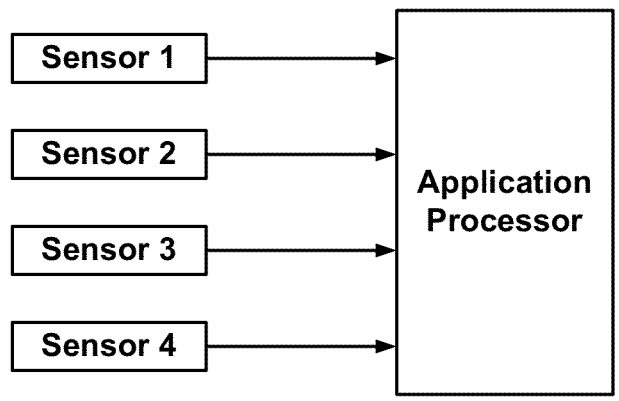
FIG. 14C illustrates an example of a sensor device which has one or multiple sensors connected to an application processor.
Figure 14D:
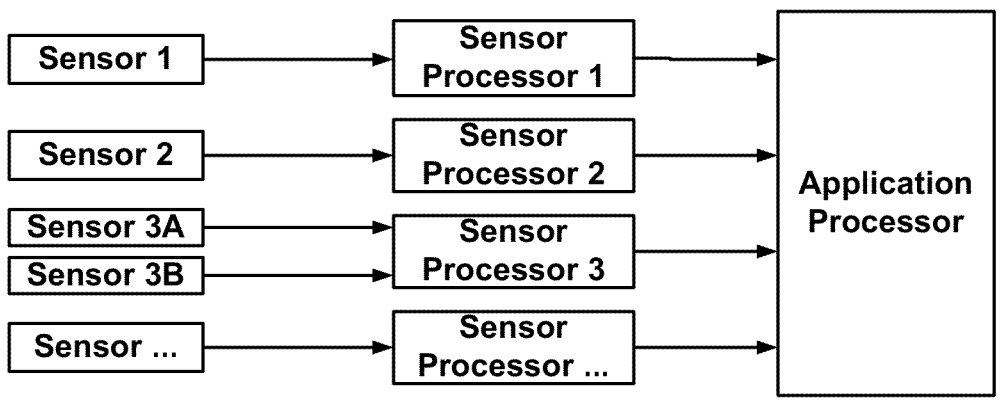
FIG. 14D illustrates an example of a sensor device which has one or multiple sensors connected to sensor processors which, in turn, are connected to an application processor.

In one embodiment, the biometric monitoring device may include an altimeter sensor, for example, disposed or located in the interior of the device housing. (See, for example, FIGS. 12B and 12C; FIG. 12C illustrates an example of a portable biometric monitoring device having physiological sensors, environmental sensors, and location sensors connected to a processor). In such a case, the device housing may have a vent that allows the interior of the device to measure, detect, sample and/or experience any changes in exterior pressure. In one embodiment, the vent may prevent water from entering the device while facilitating measuring, detecting and/or sampling changes in pressure via the altimeter sensor. For example, an exterior surface of the biometric monitoring device may include a vent type configuration or architecture (for example, a Gore™ vent) that allows ambient air to move in and out of the housing of the device (which allows the altimeter sensor to measure, detect and/or sample changes in pressure), but reduces, prevents, and/or minimizes water and other liquids from flowing into the housing of the device.

The altimeter sensor, in one embodiment, may be filled with gel that allows the sensor to experience pressure changes

| Sensor Integrations | Data derived from signal processing of multiple sensors |
| --- | --- |
| Skin Temp and Ambient Temp | Heat Flux |
| Heart Rate and Motion | Elevation gain |
| Motion detector and other user's motion detector (linked by wireless communication path) | Users in the proximity |
| Motion, any heartbeat waveform sensor, galvanic skin response | Sit/Standing detection |
| Any heart rate, heart rate variability sensor, respiration, motion | Sleep Phase detection<br>Sleep Apnea detection |
| Any heartbeat waveform sensor and/or wetness sensor, and/or motion detector | Resting Heart rate<br>Active Heart Rate<br>Heart rate while asleep<br>Heart rate while sedentary |
| Any heart rate detector | Early detection of heart problems:<br>Cardiac Arrhythmia<br>Cardiac Arrest |
| Multiple heart rate detectors | Pulse transit time |
| Audio and/or strain gauge | Typing detection |
| GPS and photoplethysmography (PPG) | Location-stress correlation:<br>determination of stressful regions<br>determination of low stress regions<br>Activity-specific heart rate<br>resting heart rate<br>active heart rate<br>Automatic activity classification and activity heart rate determination |
| Heart rate, galvanic skin response, accelerometer and respiration | User fatigue, for example while exercising |

In some embodiments, the biometric monitoring device may also include a near-field communication (NFC) receiver/transmitter to detect proximity to another device, such as a mobile phone. When the biometric monitoring device is brought into close or detectable proximity to the second device, it may trigger the start of new functionality on the second device (e.g., the launching of an "app" on the mobile phone and radio syncing of physiological data from the device to the second device). (See, for example, FIG. 10). Indeed, the biometric monitoring device of the present disclosure may implement any of the circuitry and techniques described and/or illustrated in U.S. Provisional Patent Application 61/606,559, filed Mar. 5, 2012, "Near Field Communication System, and Method of Operating Same", inventor: James Park (the contents of which are incorporated herein by reference for such purpose).

Figure 10:
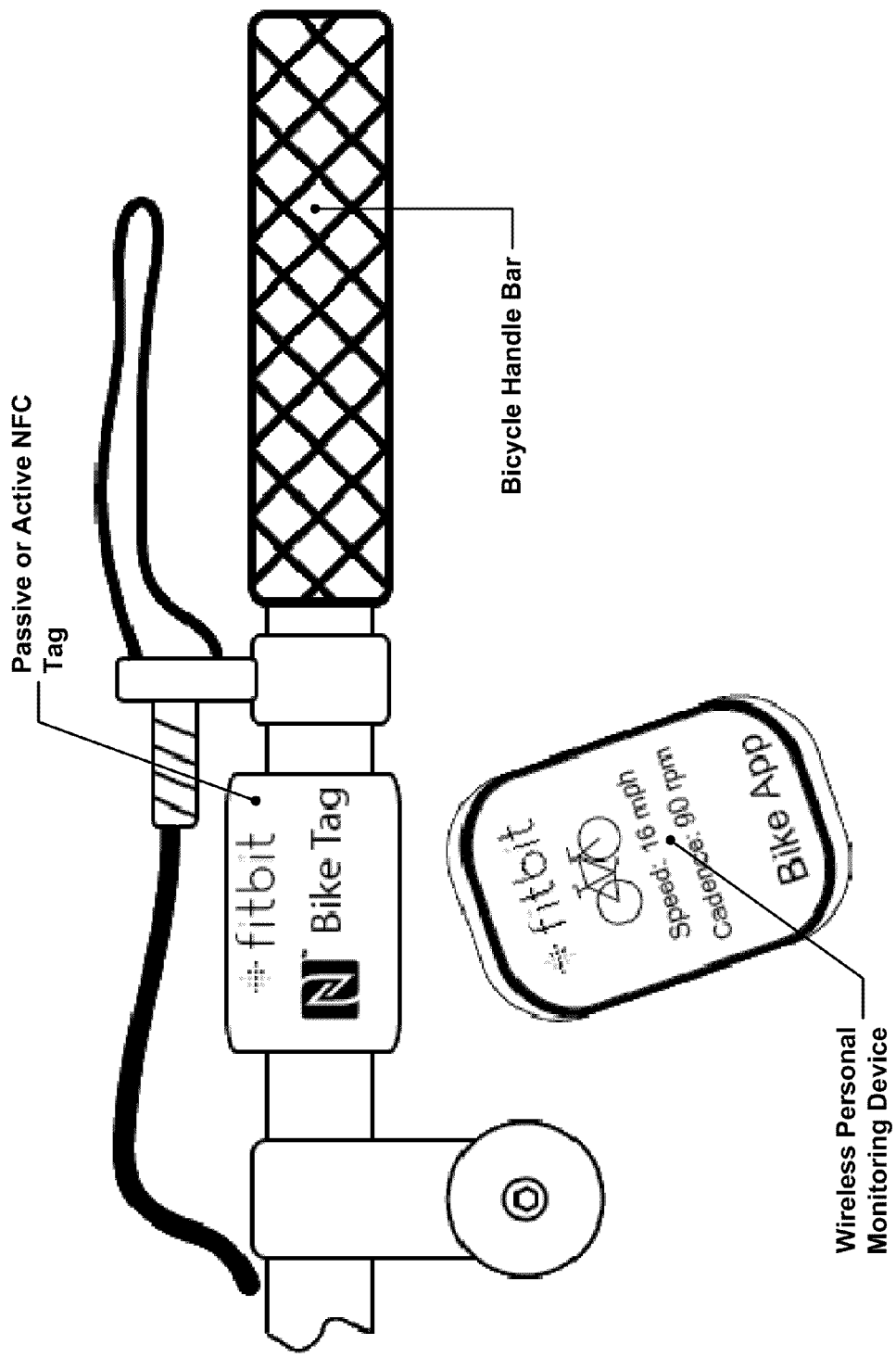
FIG. 10 illustrates an example of a portable biometric monitoring device that has a bicycle application on it that may display bicycle speed and/or pedaling cadence, among other metrics.

FIG. 10 illustrates an example of a portable biometric monitoring device that has a bicycle application on it that may display bicycle speed and/or pedaling cadence, among other metrics. The app may be activated whenever the biometric monitoring device comes into proximity of a passive or active NFC tag. This NFC tag may be attached to the user's handlebars.

In another embodiment, the biometric monitoring device may include a location sensor (for example, GPS circuitry) and heartbeat waveform sensor (for example, photoplethysmography circuitry) to generate GPS- or location-related data and heart rate-related data, respectively. (See, for example, FIGS. 12B and 12C). The biometric monitoring device may then fuse, process and/or combine data from these two sensors/circuitries to, for example, determine, correlate, and/or "map" geographical regions according to physiological data (for example, heart rate, stress, activity level, quantity of sleep and/or caloric intake). In this way, the biometric monitoring device may identify geographical regions that increase or decrease a measurable user metric including, but not limited to, heart rate, stress, activity, level, quantity of sleep and/or caloric intake.

In addition thereto, or in lieu thereof, some embodiments of biometric monitoring devices may employ GPS-related data and photoplethysmography-related data (notably, each of which may be considered data streams) to determine or correlate the user's heart rate according to activity levels—for example, as determined by the user's acceleration, speed, location and/or distance traveled (as measured by the GPS and/or determined from GPS-related data). (See, for example, FIGS. 12B and 12C). Here, in one embodiment, heart rate as a function of speed may be "plotted" for the user, or the data may be broken down into different levels including, but not limited to, sleeping, resting, sedentary, moderately active, active, and highly active.

Indeed, some embodiments of biometric monitoring devices may also correlate GPS-related data to a database of predetermined geographic locations that have activities associated with them for a set of predetermined conditions. For example, activity determination and corresponding physiological classification (for example, heart rate classification) may include correlating a user's GPS coordinates that correspond to location(s) of exercise equipment, health club and/or gym and physiological data. Under these circumstances, a user's heart rate during, for example a gym workout, may be automatically measured and displayed. Notably, many physiological classifications may be based on GPS-related data including location, acceleration, altitude, distance and/or velocity. Such a database including geographic data and physiological data may be compiled, developed and/or stored on the biometric monitoring device and/or external computing device. Indeed, in one embodiment, the user may create their own location database or add to or modify the location database to better classify their activities.

In another embodiment, the user may simultaneously wear multiple biometric monitoring devices (having any of the features described herein). The biometric monitoring devices of this embodiment may communicate with each other or a remote device using wired or wireless circuitry to calculate, for example, biometric or physiologic qualities or quantities that, for example, may be difficult or inaccurate to calculate otherwise, such as pulse transit time. The use of multiple sensors may also improve the accuracy and/or precision of biometric measurements over the accuracy and/or precision of a single sensor. For example, having a biometric tracking device on the waist, wrist, and ankle may improve the detection of the user taking a step over that of a single device in only one of those locations. Signal processing may be performed on the biometric tracking devices in a distributed or centralized method to provide measurements improved over that of a single device. This signal processing may also be performed remotely and communicated back to the biometric tracking devices after processing.

In another embodiment, heart rate or other biometric data may be correlated to a user's food log (a log of foods ingested by a user, their nutritional content, and portions thereof). Food log entries may be entered into the food log automatically or may be entered by the user themselves through interaction with the biometric monitoring device (or a secondary or remote device, e.g., a smartphone, in communication with the biometric monitoring device or some other device, e.g., a server, in communication with the biometric monitoring device). Information may be presented to the user regarding the biometric reaction of their body to one or more food inputs. For example, if a user has coffee, their heart rate may rise as a result of the caffeine. In another example, if a user has a larger portion of food late at night, it may take longer for them to fall asleep than usual. Any combination of food input and corresponding result in biometrics may be incorporated into such a feedback system.

The fusion of food intake data and biometric data may also enable some embodiments of biometric monitoring device to make an estimation of a user's glucose level. This may be particularly useful for users who have diabetes. With an algorithm which relates the glucose level to the user's activity (e.g. walking, running, calorie burn) and nutritional intake, a biometric monitoring device may be able to advise the user when they are likely to have an abnormal blood sugar level.

Processing Task Delegation

Embodiments of biometric monitoring devices may include one or more processors. For example, an independent application processor may be used to store and execute applications that utilize sensor data acquired and processed by one or more sensor processors (processor(s) that process data from physiological, environmental, and/or activity sensors). In the case where there are multiple sensors, there may also be multiple sensor processors. An application processor may have sensors directly connected to it as well. Sensor and application processors may exist as separate discrete chips or exist within the same packaged chip (multi-core). A device may have a single application processor, or an application processor and sensor processor, or a plurality of application processors and sensor processors.

In one embodiment, the sensor processor may be placed on a daughterboard that consists of all of the analog components. This board may have some of the electronics typically found on the main PCB such as, but not limited to, transimpedance amplifiers, filtering circuits, level shifters, sample-and-hold circuits, and a microcontroller unit. Such a configuration may allow the daughterboard to be connected to the main PCB through the use of a digital connection rather than an analog connection (in addition to any necessary power or ground connections). A digital connection may have a variety of advantages over an analog daughterboard to main PCB connection, including, but not limited to, a reduction in noise and a reduction in the number of necessary cables. The daughterboard may be connected to the main board through the use of a flex cable or set of wires.

Multiple applications may be stored on an application processor. An application may consist of executable code and data for the application, but is not limited to these. Data may consist of graphics or other information required to execute the application or it may be information output generated by the application. The executable code and data for the application may both reside on the application processor (or memory incorporated therein) or the data for the application may be stored and retrieved from an external memory. External memory may include but is not limited to NAND flash, NOR flash, flash on another processor, other solid-state storage, mechanical or optical disks, RAM, etc.

The executable code for an application may also be stored in an external memory. When a request to execute an application is received by the application processor, the application processor may retrieve the executable code and/or data from the external storage and execute it. The executable code may be temporarily or permanently stored on the memory or storage of the application processor. This allows the application to be executed more quickly on the next execution request, since the step of retrieval is eliminated. When the application is requested to be executed, the application processor may retrieve all of the executable code of the application or portions of the executable code. In the latter case, only the portion of executable code required at that moment is retrieved. This allows applications that are larger than the application processor's memory or storage to be executed.

The application processor may also have memory protection features to prevent applications from overwriting, corrupting, interrupting, blocking, or otherwise interfering with other applications, the sensor system, the application processor, or other components of the system.

Applications may be loaded onto the application processor and/or any external storage via a variety of wired, wireless, optical, or capacitive mechanisms including, but not limited to, USB, Wi-Fi, Bluetooth, Bluetooth Low Energy, NFC, RFID, Zigbee.

Applications may also be cryptographically signed with an electronic signature. The application processor may restrict the execution of applications to those that have the correct signature.

Integration of Systems in a Biometric Monitoring Device

In some implementations of biometric monitoring devices, some sensors or electronic systems in the biometric monitoring device may be integrated with one another or may share components or resources. For example, a photodetector for an optically-based heartbeat waveform sensor (such as may be used in the heart-rate sensors discussed in U.S. Provisional Patent Application No. 61/946,439, filed Feb. 28, 2014, and previously incorporated by reference herein), may also serve as a photodetector for determining ambient light level, such as may be used to correct for the effects of ambient light on the heartbeat waveform sensor reading. For example, if the light source for such a heart rate detector is turned off, the light that is measured by the photodetector may be indicative of the amount of ambient light that is present.

In some implementations of a biometric monitoring device, the biometric monitoring device may be configured or communicated with using onboard optical sensors such as the components in an optical heart rate monitor. For example, the photodetectors of an optical heart-rate sensor (or, if present, an ambient light sensor) may also serve as a receiver for an optically-based transmission channel, e.g., infrared communications.

In some implementations of a biometric monitoring device, a hybrid antenna may be included that combines a radio frequency antenna, e.g., a Bluetooth antenna or GPS antenna, with an inductive loop, such as may be used in a near-field communications (NFC) tag or in an inductive charging system. In such implementations, the functionality for two different systems may be provided in one integrated system, saving packing volume. In such a hybrid antenna, an inductive loop may be placed in close proximity to the radiator of an inverted-F antenna. The inductive loop may inductively couple with the radiator, allowing the inductive loop to serve as a planar element of the antenna for radio-frequency purposes, thus forming, for example, a planar inverted-F antenna. At the same time, the inductive loop may also serve its normal function, e.g., such as providing current to an NFC chip through inductive coupling with an electromagnetic field generated by an NFC reader. Examples of such hybrid antenna systems are discussed in more detail in U.S. Provisional Patent Application No. 61/948,470, filed Mar. 5, 2014, which was previously incorporated herein by reference in the "Cross-Reference to Related Applications" section and which is again hereby incorporated by reference with respect to content directed at hybrid antenna structures. Of course, such hybrid antennas may also be used in other electronic devices other than biometric monitoring devices, and such non-biometric-monitoring-device use of hybrid antennas is contemplated as being within the scope of this disclosure.

Methods of Wearing the Device

Some embodiments of biometric monitoring devices may include a housing having a size and shape that facilitates fixing the biometric monitoring device to the user's body during normal operation wherein the device, when coupled to the user, does not measurably or appreciably impact the user's activity. The biometric monitoring device may be worn in different ways depending on the specific sensor package that is integrated into the biometric monitoring device and the data that the user would like to acquire.

A user may wear some embodiments of the biometric monitoring devices of the present disclosure on their wrist or ankle (or arm or leg) with the use of a band that is flexible and thereby readily fitted to the user. The band may have an adjustable circumference, therefore allowing it to be fitted to the user. The band may be constructed from a material that shrinks when exposed to heat, therefore allowing the user to create a custom fit. The band may be detachable from the "electronics" portion of the biometric monitoring device and, if necessary, replaceable.

In some embodiments, the biometric monitoring device may consist of two major components—a body (containing the "electronics") and a band (that facilitates attaching the device to the user). The body may include a housing (made, for example, of a plastic or plastic-like material) and extension tabs projecting from the body (made, for example, from a metal or metal-like material). (See, for example, FIGS. 2C through 3C). The band (made, for example, of a thermoplastic urethane) may be attachable to the body, e.g., mechanically or adhesively. The band may extend out a fraction of the circumference of the user's wrist. The distal ends of the urethane band may be connected with a Velcro or a hook-and-loop elastic fabric band that loops around a D-Ring on one side and then attaches back to itself. In this embodiment, the closure mechanism may allow the user infinite band length adjustment (unlike an indexed hole and mechanical clasp closure). The Velcro or elastic fabric may be attached to the band in a manner that allows it to be replaced (for example, if it is worn or otherwise undesirable to wear before the useful end of life of the device). In one embodiment, the Velcro or fabric may be attached with screws or rivets and/or glue, adhesives, and/or a clasp to the band.

Embodiments of the biometric monitoring devices of the present disclosure may also be integrated into and worn in a necklace, chest band, bra, adhesive patch, glasses, earring, or toe band. Such biometric monitoring devices may be built in such a way that the sensor package/portion of the biometric monitoring device is removable and may be worn in any number of ways including, but not limited to, those listed above.

In another embodiment, embodiments of biometric monitoring devices of the present disclosure may be worn clipped to an article of clothing or deposited in clothing (e.g., pocket) or an accessory (e.g., handbag, backpack, wallet). Because such biometric monitoring devices may not be near the user's skin, in embodiments that include heart rate measurements, the measurements may be obtained in a discrete, "on demand" context by the user manually placing the device into a specific mode (e.g., by depressing a button, covering a capacitive touch sensor with a fingertip, etc., possibly with the heartbeat waveform sensor embedded in the button/sensor) or automatically once the user places the device against the skin (e.g., applying the finger to an optical heartbeat waveform sensor).

User Interface with the Device

Some embodiments of a biometric monitoring device may include functionality for allowing one or more methods of interacting with the device either locally or remotely.

In some embodiments, the biometric monitoring device may convey data visually through a digital display. The physical embodiment of this display may use any one or a plurality of display technologies including, but not limited to one or more of LED, LCD, AMOLED, E-Ink, Sharp display technology, graphical displays, and other display technologies such as TN, HTN, STN, FSTN, TFT, IPS, and OLET. This display may show data acquired or stored locally on the device or may display data acquired remotely from other devices or Internet services. The biometric monitoring device may use a sensor (for example, an Ambient Light Sensor, "ALS") to control or adjust the amount of screen backlighting, if backlighting is used. For example, in dark lighting situations, the display may be dimmed to conserve battery life, whereas in bright lighting situations, the display brightness may be increased so that it is more easily read by the user.

In another embodiment, the biometric monitoring device may use single or multicolor LEDs to indicate a state of the device. States that the biometric monitoring device may indicate using LEDs may include, but are not limited to, biometric states such as heart rate or application states such as an incoming message or that a goal has been reached. These states may be indicated through the LED's color, the LED being on or off (or in an intermediate intensity), pulsing (and/or rate thereof) of the LEDs, and/or a pattern of light intensities from completely off to highest brightness. In one embodiment, an LED may modulate its intensity and/or color with the phase and frequency of the user's heart rate.

In some embodiments, the use of an E-Ink display may allow the display to remain on without the battery drain of a non-reflective display. This "always-on" functionality may provide a pleasant user experience in the case of, for example, a watch application where the user may simply glance at the biometric monitoring device to see the time. The E-Ink display always displays content without compromising the battery life of the device, allowing the user to see the time as they would on a traditional watch.

Some implementations of a biometric monitoring device may use a light such as an LED to display the heart rate of the user by modulating the amplitude of the light emitted at the frequency of the user's heart rate. The device may depict heart rate zones (e.g., aerobic, anaerobic, etc.) through the color of an LED (e.g., green, red) or a sequence of LEDs that light up in accordance with changes in heart rate (e.g., a progress bar). The biometric monitoring device may be integrated or incorporated into another device or structure, for example, glasses or goggles, or communicate with glasses or goggles to display this information to the user.

Some embodiments of a biometric monitoring device may also convey information to a user through the physical motion of the device. One such embodiment of a method to physically move the device is the use of a vibration-inducing motor. The device may use this method alone, or in combination with a plurality of other motion-inducing technologies.

In some implementations, a biometric monitoring device may convey information to a user through audio feedback. For example, a speaker in the biometric monitoring device may convey information through the use of audio tones, voice, songs, or other sounds.

These three information communication methods—visual, motion, and auditory—may, in various embodiments of biometric monitoring devices, be used alone or in any combination with each other or another method of communication to communicate any one or plurality of the following information:

That a user needs to wake up at certain time
That a user should wake up as they are in a certain sleep phase
That a user should go to sleep as it is a certain time
That a user should wake up as they are in a certain sleep phase and in a preselected time window bounded by the earliest and latest time that the user wants to wake up.
That an email was received
That the user has been inactive for a certain period of time. Notably, this may integrate with other applications like, for instance, a meeting calendar or sleep tracking application to block out, reduce, or adjust the behavior of the inactivity alert.
That the user has been active for a certain period of time
That the user has an appointment or calendar event
That the user has reached a certain activity metric
That the user has gone a certain distance
That the user has reached a certain mile pace
That the user has reached a certain speed
That the user has accumulated a certain elevation gain
That the user has taken a certain number of steps
That the user has had a heart rate measurement recently
That the user's heart rate has reached a certain level
That the user has a normal, active, or resting heart rate of a specific value or in a specific range
That the user's heart rate has enter or exited a certain goal range or training zone
That the user has a new heart rate "zone" goal to reach, as in the case of heart rate zone training for running, bicycling, swimming, etc. activities
That the user has swum a lap or completed a certain number of laps in a pool
An external device has information that needs to be communicated to the user such as an incoming phone call or any one of the above alerts
That the user has reached a certain fatigue goal or limit. In one embodiment, fatigue may be determined through a combination of heart rate, galvanic skin response, motion sensor, and/or respiration data These examples are provided for illustration and are not intended to limit the scope of information that may be communicated by such embodiments of biometric monitoring devices (for example, to the user). Note that the data used to determine whether or not an alert condition is met may be acquired from a first device and/or one or more secondary devices. The biometric monitoring device itself may determine whether the criteria or conditions for an alert have been met. Alternatively, a computing device in communication with the biometric monitoring device (e.g., a server and/or a mobile phone) may determine when the alert should occur. In view of this disclosure, other information that the biometric monitoring device may communicate to the user may be envisioned by one of ordinary skill in the art. For example, the biometric monitoring device may communicate with the user when a goal has been met. The criteria for meeting this goal may be based on physiological, contextual, and environmental sensors on a first device, and/or other sensor data from one or more secondary devices. The goal may be set by the user or may be set by the biometric monitoring device itself and/or another computing device in communication with the biometric monitoring device (e.g. a server). In an example embodiment, the biometric monitoring device may vibrate when a biometric goal is met.

Some embodiments of biometric monitoring devices of the present disclosure may be equipped with wireless and/or wired communication circuitry to display data on a secondary device in real time. For example, such biometric monitoring devices may be able to communicate with a mobile phone via Bluetooth Low Energy in order to give real-time feedback of heart rate, heart rate variability, and/or stress to the user. Such biometric monitoring devices may coach or grant "points" for the user to breathe in specific ways that alleviate stress (e.g. by taking slow, deep breaths). Stress may be quantified or evaluated through heart rate, heart rate variability, skin temperature, changes in motion-activity data and/or galvanic skin response.

Some embodiments of biometric monitoring devices may receive input from the user through one or more local or remote input methods. One such embodiment of local user input may use a sensor or set of sensors to translate a user's movement into a command to the device. Such motions could include but may not be limited to tapping, rolling the wrist, flexing one or more muscles, and swinging one's arm. Another user input method may be through the use of a button such as, but not limited to, capacitive touch buttons, capacitive screen buttons, and mechanical buttons. In one embodiment, the user interface buttons may be made of metal. In embodiments where the screen uses capacitive touch detection, it may always be sampling and ready to respond to any gesture or input without an intervening event such as pushing a physical button. Such biometric monitoring devices may also take input through the use of audio commands. All of these input methods may be integrated into biometric monitoring devices locally or integrated into a remote device that can communicate with such biometric monitoring devices, either through a wired or wireless connection. In addition, the user may also be able to manipulate the biometric monitoring device through a remote device. In one embodiment, this remote device may have Internet connectivity.

Alarms

In some embodiments, the biometric monitoring device of the present disclosure may act as a wrist-mounted vibrating alarm to silently wake the user from sleep. Such biometric monitoring devices may track the user's sleep quality, waking periods, sleep latency, sleep efficiency, sleep stages (e.g., deep sleep vs REM), and/or other sleep-related metrics through one or a combination of heart rate, heart rate variability, galvanic skin response, motion sensing (e.g., accelerometer, gyroscope, magnetometer), and skin temperature. The user may specify a desired alarm time or window of time (e.g., set alarm to go off between 7 am and 8 am). Such embodiments may use one or more of the sleep metrics to determine an optimal time within the alarm window to wake the user. In one embodiment, when the vibrating alarm is active, the user may cause it to hibernate or turn off by slapping or tapping the device (which is detected, for example, via motion sensor(s), a pressure/force sensor, and/or capacitive touch sensor in the device). In one embodiment, the device may attempt to arouse the user at an optimum point in the sleep cycle by starting a small vibration at a specific user sleep stage or time prior to the alarm setting. It may progressively increase the intensity or noticeability of the vibration as the user progresses toward wakefulness or toward the alarm setting. (See, for example, FIG. 8).

Figure 8:
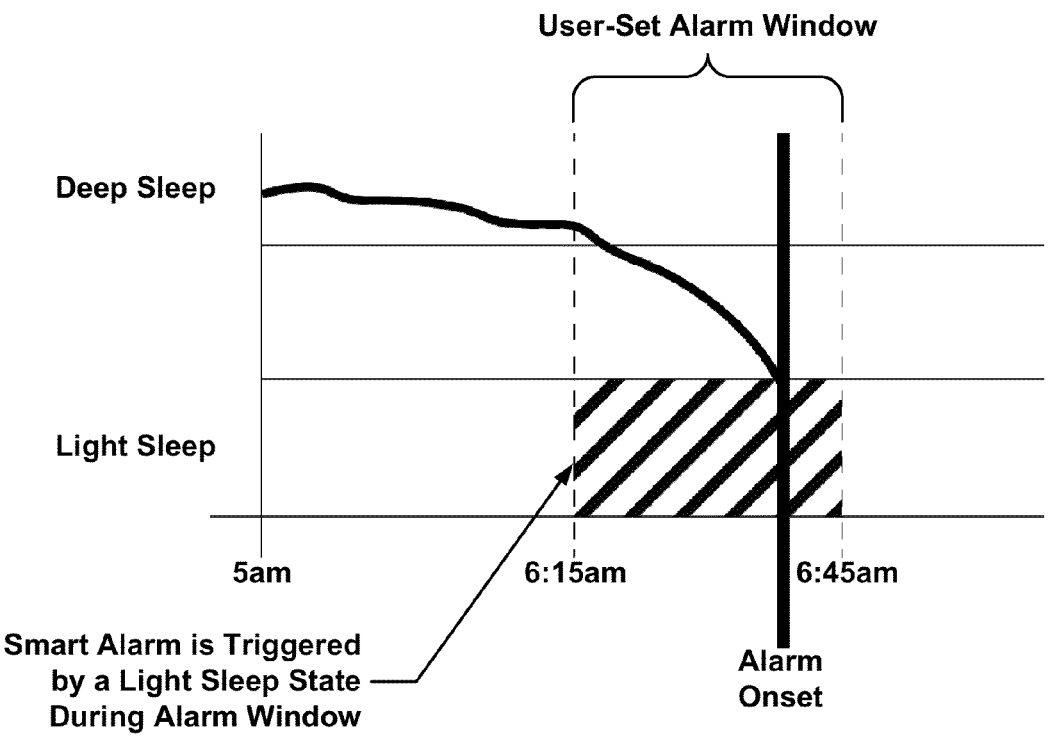
FIG. 8 illustrates functionality of an example biometric monitoring device smart alarm feature.

FIG. 8 illustrates functionality of an example portable biometric monitoring device smart alarm feature. The biometric monitoring device may be able to detect or may be in communication with a device that can detect the sleep stage or state of a user (e.g., light or deep sleep). The user may set a window of time which they would like to be awoken (e.g., 6:15 am to 6:45 am). The smart alarm may be triggered by the user going into a light sleep state during the alarm window.

The biometric monitoring device may be configured to allow the user to select or create an alarm vibration pattern of their choice. The user may have the ability to "snooze" or postpone an alarm event. In one embodiment, the user may be able to set the amount of delay for the "snooze" feature—the delay being the amount of time before the alarm will go off again. They may also be able to set how many times the snooze feature may be activated per alarm cycle. For example, a user may choose a snooze delay of 5 minutes and a maximum sequential snooze number to be 3. Therefore, they can press snooze up to 3 times to delay the alarm by 5 minutes each time they press snooze to delay the alarm. In such embodiments, the snooze function will not turn off the alarm if the user attempts to press snooze a fourth time.

Some biometric monitoring devices may have information about the user's calendar and/or schedule. The user's calendar information may be entered directly into the biometric monitoring device or it may be downloaded from a different device (e.g. a smartphone). This information may be used to automatically set alarms or alarm characteristics. For example, if a user has a meeting at 9 am in the morning, the biometric monitoring device may automatically wake the user up at 7:30 am to allow the user enough time to prepare for and/or get to the meeting. The biometric monitoring device may determine the amount of time required for the user to prepare for the meeting based on the user's current location, the location of the meeting, and the amount of time it would take to get the location of the meeting from the user's current location. Alternatively, historical data about how long the user takes to get to the meeting location and/or prepare to leave for the meeting (e.g. how long it takes to wake up, take a shower, have breakfast, etc. in the morning) may be used to determine at what time to wake the user. A similar functionality may be used for calendar events other than meetings such as eating times, sleeping times, napping times, and exercise times.

In some embodiments, the biometric monitoring device may use information on when the user went to sleep to determine when an alarm should go off to wake the user. This information may supplement calendar information described herein. The user may have a goal of approximately how many hours of sleep they would like to get each night or week. The biometric monitoring device may set the morning alarm at the appropriate time for the user to meet these sleep goals. In addition to amount of time that the user would like to sleep each night, other sleep goals that the user may set may include, but are not limited to, the amount of deep sleep, REM sleep, and light sleep that the user experiences while sleeping, all of which may be used by the biometric monitoring device to determine when to set an alarm in the morning. Additionally, the user may be alerted at night when they should go to bed to meet their sleep goals. Additionally, the user may be alerted during the day when they should take a nap to meet their sleep goals. The time at which to alert a user that they should take a nap may be determined by factors that optimize the user's sleep quality during the nap, subsequent naps, or night-time sleep. For example, the user is likely to have a hard time falling asleep at night if they took a nap in the early evening. The user may also be advised to eat certain foods or drinks or avoid certain foods or drinks to optimize their sleep quality. For example, a user may be discouraged from drinking alcohol close to their bed time as it is likely to decrease their sleep quality. The user may also be advised to perform certain activities or avoid certain activities to optimize their sleep quality. For example, a user may be encouraged to exercise in the early afternoon to improve their sleep quality. A user may be discouraged from exercising or watching TV close to their bedtime to improve their sleep quality.

User Interface with a Secondary Device

In some embodiments, the biometric monitoring device may transmit and receive data and/or commands to and/or from a secondary electronic device. The secondary electronic device may be in direct or indirect communication with the biometric monitoring device. Direct communication refers herein to the transmission of data between a first device and a secondary device without any intermediary devices. For example, two devices may communicate to one another over a wireless connection (e.g. Bluetooth) or a wired connection (e.g. USB). Indirect communication refers to the transmission of data between a first device and a secondary device with the aid of one or multiple intermediary third devices which relay the data. Third devices may include, but are not limited to, a wireless repeater (e.g. WiFi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In some embodiments, the secondary device that acts as a user interface to the biometric monitoring device may consist of a smartphone. An app on the smart phone may facilitate and/or enable the smartphone to act as a user interface to the biometric monitoring device. The biometric monitoring device may send biometric and other data to the smartphone in real-time or with some delay. The smartphone may send a command or commands to the biometric monitoring device, for example, to instruct it to send biometric and other data to the smartphone in real-time or with some delay. For example, if the user enters a mode in the app for tracking a run, the smartphone may send a command to the biometric device to instruct it to send data in real-time. Therefore, the user can track their run on their app as they go along without any delay.

Such a smartphone may have one or multiple apps to enable the user to view data from their biometric device or devices. The app may, by default, open to a "dashboard" page when the user launches or opens the app. On this page, summaries of data totals such as the total number of steps, floors climbed miles traveled, calories burned, calories consumed and water consumed may be shown. Other pertinent information such as the last time the app received data from the biometric monitoring device, metrics regarding the previous night's sleep (e.g. when the user went to sleep, woke up, and how long they slept for), and how many calories the user can eat in the day to maintain their caloric goals (e.g. a calorie deficit goal to enable weight loss) may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping to the left or right may enable the user to navigate through current and previous metrics.

The smartphone app may also have another page which provides a summary of the user's activities. Activities may include, but are not limited to, walking, running, biking, cooking, sitting, working, swimming, working out, weightlifting, commuting, and yoga. Metrics pertinent to these activities may be presented on this page. For example, a bar graph may show how the number of steps the user took for different portions of the day (e.g. how many steps every 5 minutes or 1 hour). In another example, the amount of time the user spent performing a certain activity and how many calories were burned in this period of time may be displayed. Similar to the dashboard page, the app may provide navigational functionality to allow the user to see these and other metrics for past days. Other time periods such as an hour, minute, week, month or year may also be selected by the user to enable them to view trends and metrics of their activities over shorter or larger spans of time.

The smartphone app may also have an interface to log food that has been, or will be, eaten by the user. This interface may have a keyword search feature to allow the user to quickly find the food that they would like to enter into their log. As an alternative to, or in addition to, searching for foods, users may have the ability to find a food to log by navigating through a menu or series of menus. For example, a user may choose the following series of categories—breakfast/cereal/healthy/oatmeal to arrive at the food which they would like to log (e.g., apple-flavored oatmeal). At any one of these menus, the user may be able to perform a keyword search. For example, the user may search for "oatmeal" after having selected the category "breakfast" to search for the keyword "oatmeal" within the category of breakfast foods. After having selected the food that they would like to log, the user may be able to modify or enter the serving size and nutritional content. After having logged at least one food, the app may display a summary of the foods that were logged in a certain time period (e.g. a day) and the nutritional content of the foods (individual and total calorie content, vitamin content, sugar content, etc.).

The smartphone app may also have a page that displays metrics regarding the user's body such as the user's weight, body fat percentage, BMI, and waist size. It may display a graph or graphs showing the trend of one or multiple of these metrics over a certain period of time (e.g., two weeks). The user may be able to choose the value of this period of time and view previous time periods (e.g., last month).

The smartphone app may also have a page which allows the user to enter how much water the user has consumed. Each time the user drinks some water, they may enter that amount in the unit of their choice (e.g., ozs., cups, etc.). The app may display the total of all of the water the user has logged within a certain time period (e.g., a day). The app may allow the user to see previously-logged water entries and daily totals for previous days as well as the current day.

The smartphone app may also have a page that displays online friends of the user. This "friends" page may enable the user to add or request new friends (e.g., by searching for their name or by their email address). This page may also display a leaderboard of the user and his or her friends. The user and his or her friends may be ranked based on one or more metrics. For example, the user and his or her friends may be ranked using the total of the past seven days' step counts.

The smartphone app may also have a page that shows metrics regarding the user's sleep for the previous night and/or previous nights. This page may also enable the user to log when they slept in the past by specifying when they went to bed and when they woke. The user may also have the ability to enter a subjective metric about their sleep (e.g., bad night's rest, good night's rest, excellent night's rest, etc.). The user may be able to view these metrics for days or time periods (e.g., two weeks) in the past. For example, the sleep page may default to showing a bar graph of the amount of time the user slept each night in the last two weeks. The user may be able to also view a bar graph of the amount of time the user slept each night in the last month.

The user may also be able to access the full capabilities of the smartphone app described herein (e.g., the ability to enter food logs, view dashboard, etc.) through an alternative or additional interface. In one embodiment, this alternative interface may consist of a webpage that is hosted by a server in indirect communication with the biometric monitoring device. The webpage may be accessed through any internet connected device using a program such as a web browser.

Wireless Connectivity and Data Transmission

Some embodiments of biometric monitoring devices of the present disclosure may include a means of wireless communication to transmit and receive information from the Internet and/or other devices. The wireless communication may consist of one or more interfaces such as Bluetooth, ANT, WLAN, power-line networking, and cell phone networks. These are provided as examples and should not be understood to exclude other existing wireless communication methods or protocols, or wireless communications techniques or protocols that are yet to be invented.

The wireless connection may be bi-directional. The biometric monitoring device may transmit, communicate and/or push its data to other devices, e.g., smart phones, computers, etc., and/or the Internet, e.g., web servers and the like. The biometric monitoring device may also receive, request and/or pull data from other devices and/or the Internet.

The biometric monitoring device may act as a relay to provide communication for other devices to each other or to the Internet. For example, the biometric monitoring device may connect to the Internet via WLAN but also be equipped with an ANT radio. An ANT device may communicate with the biometric monitoring device to transmit its data to the Internet through the biometric monitoring device's WLAN (and vice versa). As another example, the biometric monitoring device may be equipped with Bluetooth. If a Bluetooth-enabled smart phone comes within range of the biometric monitoring device, the biometric monitoring device may transmit data to, or receive data from, the Internet through the smart phone's cell phone network. Data from another device may also be transmitted to the biometric monitoring device and stored (or vice versa) or transmitted at a later time.

Embodiments of biometric monitoring devices of the present disclosure may also include functionality for streaming or transmitting web content for display on the biometric monitoring device. The following are typical examples of such content:

1. Historical graphs of heart rate and/or other data measured by the device but stored remotely
2. Historical graphs of user activity and/or foods consumed and/or sleep data that are measured by other devices and/or stored remotely (e.g., such as at a website like fitbit.com)
3. Historical graphs of other user-tracked data that are stored remotely. Examples include heart rate, blood pressure, arterial stiffness, blood glucose levels, cholesterol, duration of TV watching, duration of video game play, mood, etc.
4. Coaching and/or dieting data based on one or more of the user's heart rate, current weight, weight goals, food intake, activity, sleep, and other data.
5. User progress toward heart rate, weight, activity, sleep, and/or other goals.
6. Summary statistics, graphics, badges, and/or metrics (e.g., "grades") to describe the aforementioned data
7. Comparisons between the aforementioned data for the user and similar data for his/her "friends" with similar devices and/or tracking methods
8. Social content such as Twitter feeds, instant messaging, and/or Facebook updates
9. Other online content such as newspaper articles, horoscopes, weather reports, RSS feeds, comics, crossword puzzles, classified advertisements, stock reports, and websites
10. Email messages and calendar schedules Content may be delivered to the biometric monitoring device according to different contexts. For instance, in the morning, news and weather reports may be displayed along with the user's sleep data from the previous night. In the evening, a daily summary of the day's activities may be displayed.

Various embodiments of biometric monitoring devices as disclosed herein may also include NFC, RFID, or other short-range wireless communication circuitry that may be used to initiate functionality in other devices. For instance, a biometric monitoring device may be equipped with an NFC antenna so that when a user puts it into close proximity with a mobile phone, an app is launched automatically on the mobile phone.

These examples are provided for illustration and are not intended to limit the scope of data that may be transmitted, received, or displayed by the device, nor any intermediate processing that may occur during such transfer and display. In view of this disclosure/application, many other examples of data that may be streamed to or via a biometric monitoring device may be envisioned by one reasonably skilled in the art.

Charging and Data Transmission

Some embodiments of biometric monitoring devices may use a wired connection to charge an internal rechargeable battery and/or transfer data to a host device such as a laptop or mobile phone. In one embodiment, similar to one discussed earlier in this disclosure, the biometric monitoring device may use magnets to help the user align the biometric monitoring device to a dock or cable. The magnetic field of magnets in the dock or cable and the magnets in the device itself may be strategically oriented so as to force the biometric monitoring device to self-align with the dock or cable (or, more specifically, a connector on the cable) and so as to provide a force that holds the biometric monitoring device in the dock or to the cable. The magnets may also be used as conductive contacts for charging or data transmission purposes. In another embodiment, a permanent magnet may only be used in the dock or cable side and not in the biometric monitoring device itself. This may improve the performance of the biometric monitoring device where the biometric monitoring device employs a magnetometer. If there is a magnet in the biometric monitoring device, the strong field of a nearby permanent magnet may make it significantly more difficult for the magnetometer to accurately measure the earth's magnetic field. In such embodiments, the biometric monitoring device may utilize a ferrous material in place of a magnet, and the magnets on the dock or cable side may attach to the ferrous material.

In another embodiment, the biometric monitoring device may contain one or more electromagnets in the biometric monitoring device body. The charger or dock for charging and data transmission may also contain an electromagnet and/or a permanent magnet. The biometric monitoring device could only turn on its electromagnet when it is close to the charger or dock. The biometric monitoring device may detect proximity to the dock or charger by looking for the magnetic field signature of a permanent magnet in the charger or dock using a magnetometer. Alternatively, the biometric monitoring device may detect proximity to the charger by measuring the Received Signal Strength Indication (RSSI) of a wireless signal from the charger or dock, or, in some embodiments, by recognizing an NFC or RFID tag associated with the charger or dock. The electromagnet could be reversed, creating a force that repels the device from the charging cable or dock either when the device doesn't need to be charged, synced, or when it has completed syncing or charging. In some embodiments, the charger or dock may include the electromagnet and may be configured (e.g., a processor in the charger or dock may be configured via program instructions) to turn the electromagnet on when a biometric monitoring device is connected for charging (the electromagnet may normally be left on such that a biometric monitoring device that is placed on the charger is drawn against the charger by the electromagnet, or the electromagnet may be left off until the charger determines that a biometric monitoring device has been placed on the charger, e.g., through completion of a charging circuit, recognition of an NFC tag in the biometric monitoring device, etc., and then turned on to draw the biometric monitoring device against the charger. Upon completion of charging (or of data transfer, if the charger is actually a data transfer cradle or a combined charger/data transfer cradle), the electromagnet may be turned off (either temporarily or until the biometric monitoring device is again detected as being placed on the charger) and the biometric monitoring device may stop being drawn against the charger. In such embodiments, it may be desirable to orient the interface between the biometric monitoring device and the charger such that, in the absence of a magnetic force generated by the electromagnet, the biometric monitoring device would fall off of the charger or otherwise shift into a visibly different position from the charging position (to visually indicate to a user that charging or data transfer is complete).

Sensor Use in Data Transfer

In some implementations, biometric monitoring devices may include a communications interface that may switch between two or more protocols that have different data transmission rates and different power consumption rates. Such switching may be driven by data obtained from various sensors of the biometric monitoring device. For example, if Bluetooth is used, the communications interface may switch between using Bluetooth base rate/enhanced data rate (BR/EDR) and Bluetooth low energy (BLE) protocols responsive to determinations made based on data from the sensors of the biometric monitoring device. For example, the lower-power, slower BLE protocol may be used when sensor data from accelerometers in a biometric monitoring device indicates that the wearer is asleep or otherwise sedentary. By contrast, the higher-power, faster BR/EDR protocol may be used when sensor data from the accelerometers in a biometric monitoring device indicates that the wearer is walking around. Such adaptive data transmission techniques and functionality are discussed further in U.S. Provisional Patent Application No. 61/948,468, filed Mar. 5, 2014, which was previously incorporated herein by reference in the "Cross-Reference to Related Applications" section and which is again hereby incorporated by reference with respect to content directed at adaptive data transfer rates in biometric monitoring devices.

Such communication interfaces may also serve as a form of sensor for a biometric monitoring device. For example, a wireless communications interface may allow a biometric monitoring device to determine the number and type of devices that are within range of the wireless communications interface. Such data may be used to determine if the biometric monitoring device is in a particular context, e.g., indoors, in a car, etc., and to change its behavior in various ways in response to such a determination. For example, as discussed in U.S. Provisional Patent Application No. 61/948,468 (incorporated by reference above), such contexts may be used to drive the selection of a particular wireless communications protocol to use for wireless communications.

Configurable App Functionality

In some embodiments, biometric monitoring devices of the present disclosure may include a watch-like form factor and/or a bracelet, armlet, or anklet form factor and may be programmed with "apps" that provide specific functionality and/or display specific information. Apps may be launched or closed by a variety of means including, but not limited to, pressing a button, using a capacitive touch sensor, performing a gesture that is detected by an accelerometer, moving to a specific location or area detected by a GPS or motion sensor, compressing the biometric monitoring device body (thereby creating a pressure signal inside the device that may be detected by an altimeter inside the biometric monitoring device), or placing the biometric monitoring device close to an NFC tag that is associated with an app or set of apps. Apps may also be automatically triggered to launch or close by certain environmental or physiological conditions including, but not limited to, detection of a high heart rate, detection of water using a wet sensor (to launch a swimming application, for example), a certain time of day (to launch a sleep tracking application at night, for example), a change in pressure and motion characteristic of a plane taking off or landing to launch and close an "airplane" mode app. Apps may also be launched or closed by meeting multiple conditions simultaneously. For example, if an accelerometer detects that a user is running and the user presses a button, the biometric monitoring device may launch a pedometer application, an altimeter data collection application, and/or display. In another case where the accelerometer detects swimming and the user presses the same button, it may launch a swimming lap-counting application.

In some embodiments, the biometric monitoring device may have a swim-tracking mode that may be launched by starting a swimming app. In this mode, the biometric monitoring device's motion sensors and/or magnetometer may be used to detect swim strokes, classify swim stroke types, detect swimming laps, and other related metrics such as stroke efficiency, lap time, speed, distance, and calorie burn. Directional changes indicated by the magnetometer may be used to detect a diversity of lap turn methods. In a preferred embodiment, data from a motion sensor and/or pressure sensor may be used to detect strokes.

In another embodiment, a bicycling app may be launched by moving the biometric monitoring device within proximity of an NFC or RFID tag that is located on the bicycle, on a mount on the bicycle, or in a location associated with a bicycle including, but not limited to, a bike rack or bike storage facility. (See, for example, FIG. 10). The app launched may use a different algorithm than is normally used to determine metrics including, but not limited to, calories burned, distance travelled, and elevation gained. The app may also be launched when a wireless bike sensor is detected including, but not limited to, a wheel sensor, GPS, cadence sensor, or power meter. The biometric monitoring device may then display and/or record data from the wireless bike sensor or bike sensors.

Additional apps include, but are not limited to, a programmable or customizable watch face, stop watch, music player controller (e.g., mp3 player remote control), text message and/or email display or notifier, navigational compass, bicycle computer display (when communicating with a separate or integrated GPS device, wheel sensor, or power meter), weight-lifting tracker, sit-up reps tracker, pull up reps tracker, resistance training form/workout tracker, golf swing analyzer, tennis (or other racquet sport) swing/serve analyzer, tennis game swing detector, baseball swing analyzer, ball throw analyzer (e.g., football, baseball), organized sports activity intensity tracker (e.g., football, baseball, basketball, volleyball, soccer), disk throw analyzer, food bite detector, typing analyzer, tilt sensor, sleep quality tracker, alarm clock, stress meter, stress/relaxation biofeedback game (e.g., potentially in combination with a mobile phone that provides auditory and/or visual cues to train user breathing in relaxation exercises), teeth brushing tracker, eating rate tracker (e.g., to count or track the rate and duration by which a utensil is brought to the mouth for food intake), intoxication or suitability to drive a motor vehicle indicator (e.g., through heart rate, heart rate variability, galvanic skin response, gait analysis, puzzle solving, and the like), allergy tracker (e.g., using galvanic skin response, heart rate, skin temperature, pollen sensing and the like (possibly in combination with external seasonal allergen tracking from, for instance, the internet and possibly determining the user's response to particular forms of allergen, e.g., tree pollen, and alerting the user to the presence of such allergens, e.g., from seasonal information, pollen tracking databases, or local environmental sensors in the biometric monitoring device or employed by the user), fever tracker (e.g., measuring the risk, onset, or progress of a fever, cold, or other illness, possibly in combination with seasonal data, disease databases, user location, and/or user provided feedback to assess the spread of a particular disease (e.g., flu) in relation to a user, and possibly prescribing or suggesting the abstinence of work or activity in response), electronic games, caffeine affect tracker (e.g., monitoring the physiologic response such as heart rate, heart rate variability, galvanic skin response, skin temperature, blood pressure, stress, sleep, and/or activity in either short term or long term response to the intake or abstinence of coffee, tea, energy drinks and/or other caffeinated beverages), drug affect tracker (e.g., similar to the previously mentioned caffeine tracker but in relation to other interventions, whether they be medical or lifestyle drugs such as alcohol, tobacco, etc.), endurance sport coach (e.g., recommending or prescribing the intensity, duration, or profile of a running/bicycling/swimming workout, or suggesting the abstinence or delay of a workout, in accordance with a user specified goal such as a marathon, triathlon, or custom goal utilizing data from, for instance, historical exercise activity (e.g., distance run, pace), heart rate, heart rate variability, health/sickness/stress/fever state), weight and/or body composition, blood pressure, blood glucose, food intake or caloric balance tracker (e.g., notifying the user how many calories he may consume to maintain or achieve a weight), pedometer, and nail biting detector. In some cases, the apps may rely solely on the processing power and sensors of the present disclosure. In other cases, the apps may fuse or merely display information from an external device or set of external devices including, but not limited to, a heart rate strap, GPS distance tracker, body composition scale, blood pressure monitor, blood glucose monitor, watch, smart watch, mobile communication device such as a smart phone or tablet, or server.

In one embodiment, the biometric monitoring device may control a music player on a secondary device. Aspects of the music player that may be controlled include, but are not limited to, the volume, selection of tracks and/or playlists, skipping forward or backward, fast forwarding or rewinding of tracks, the tempo of the track, and the music player equalizer. Control of the music player may be via user input or automatic based on physiological, environmental, or contextual data. For example, a user may be able to select and play a track on their smart phone by selecting the track through a user interface on the biometric monitoring device. In another example, the biometric monitoring device may automatically choose an appropriate track based on the activity level of the user (the activity level being calculated from biometric monitoring device sensor data). This may be used to help motivate a user to maintain a certain activity level. For example, if a user goes on a run and wants to keep their heart rate in a certain range, the biometric monitoring device may play an upbeat or higher tempo track if their heart rate is below the range which they are aiming for.

Automated Functions Triggered by User's Activity

Sleep Stage Triggered Functionality

Sleep stages can be monitored through various biometric signals and methods disclosed herein, such as heart rate, heart rate variability, body temperature, body motions, ambient light intensity, ambient noise level, etc. Such biometrics may be measured using optical sensors, motion sensors (accelerometers, gyroscopic sensors, etc.), microphones, and thermometers, for example, as well as other sensors discussed herein.

The biometric monitoring device may have a communication module as well, including, but not limited to, Wi-Fi (802.xx), Bluetooth (Classic, low power), or NFC. Once the sleep stages are estimated, the sleep stages may be transmitted to a cloud-based system, home server, or main control unit that is connected to communication-enabled appliances (with Wi-Fi, Bluetooth, or NFC) wirelessly. Alternatively, the biometric monitoring device may communicate directly with the communication-enabled appliances. Such communication-enabled appliances may include, for example, kitchen appliances such as, microwave ovens, coffee grinders/makers, toasters, etc.

Once the sleep stages indicate that it is close the time for the user to wake up, the biometric monitoring device may send out a trigger to the appliances that the user has indicated should be operated automatically. For example, the coffee grinder and maker may be caused to start making coffee, and the toaster may be caused to start warming up bread. The microwave oven may be caused to start cooking oatmeal or eggs as well, and electric kettle to start boiling water. So long as the ingredients are appropriately prepared, this automated signal may trigger breakfast-cooking.

Alertness Detection

Alertness, e.g., a low alertness may correlate with a person being drowsy, may also be detected from the biometrics listed above, and may be used to trigger an appliance such as a coffee maker to start brewing coffee automatically.

Hydration

The portable biometric monitoring device in combination with an activity level tracker may submit the user's activity level to a cloud-based system, home server, main control unit, or appliances directly. This may trigger some actions of the appliances, especially related to hydration, such as starting the ice cube maker of a refrigerator, or lowering operating temperature of a water purifier.

Power Saving

Many appliances typically operate in a low-power idle state that consumes power. Using aggregated information of the user's biometric signals, communication-enabled appliances may be caused to go into a super-low power mode. For example, a water dispenser at home may shut itself down into a super-low-power mode when the user is asleep or out for work, and may start cooling/heating water once the user's activity at home is expected.

Restaurant Recommendation System Based on Location and Activity

Aggregation of real-time biometric signals and location information may be used to create an educated-guess on one or multiple users' needs for a given time, e.g., ionized drink. Combining this guessed need with historical user data on the user's activity levels, activity types, activity time, and activity durations, as well as food intake data logged by the users, an app on a smart phone and/or smart watch may recommend a restaurant that would meet the user's life-style and current need.

For example, a user who just finished a six mile circuit may launch this app. The app may know that this person maintained a high activity level for the past hour, and thus determine that the person may be dehydrated. From the historical user data, the app may also know, for example, that the user's diet is heavy on vegetables but low in sugar. With an optimization algorithm that considers the user's current location, price ranges, and other factors mentioned above, the app may recommend a restaurant that offers smoothies, for example.

Swim Tracking

In some embodiments of a biometric tracking device, the biometric tracking may include a swimming algorithm that may utilize data from one or more motion sensors, altitude sensors (e.g., such as a barometric pressure sensor), orientation sensors (e.g., magnetometer), location service sensor (e.g., GPS, wireless triangulation), and/or temperature sensors. The sensors may be embedded in a single device mounted to, for instance, the wrist. In other embodiments, extra sensor devices may be attached to the swimmer's forehead, back of the head, goggles, back, hip, shoulder, thighs, legs, and/or feet.

Three potential functional components of swimming exercise analysis are as follows:

Stroke count detection—provides stroke counts per lap, where a lap is defined to be a one-way traverse from one end of the pool to the opposite end.

Stroke type classification—describes the swimming stroke type of the user (e.g., crawl stroke, breast stroke, back stroke, butterfly stroke, side stroke, kicking without strokes, body streamline, etc.) and can be any or a combination of:

a. Classification of each stroke that a user takes
b. Classification of the predominant stroke type used per complete lap.
c. Classification of stroke type used per fractional lap (e.g. half a lap of freestyle, half a lap of breast stroke)

Lap count—counts the laps traversed by the user. One method of determining a lap is by detecting when the user turns in a pool.

Turning is defined to be a 180 degree change in heading direction. As a turn is detected, start and end of a lap may be inferred. Taking a break (no motion for a certain period of time) at a point in the pool (typically at one end or the other) before starting to swim again is also considered a turn as long as the following heading direction is opposite the heading prior to the break.

In some embodiments, these functional components may be combined in a multitude of ways.

Algorithm Structure

The three functional components of the swimming exercise analysis may be performed sequentially, in parallel, or in hybrid order (a combination of some sequential blocks and some parallel blocks).

Figure 15A:
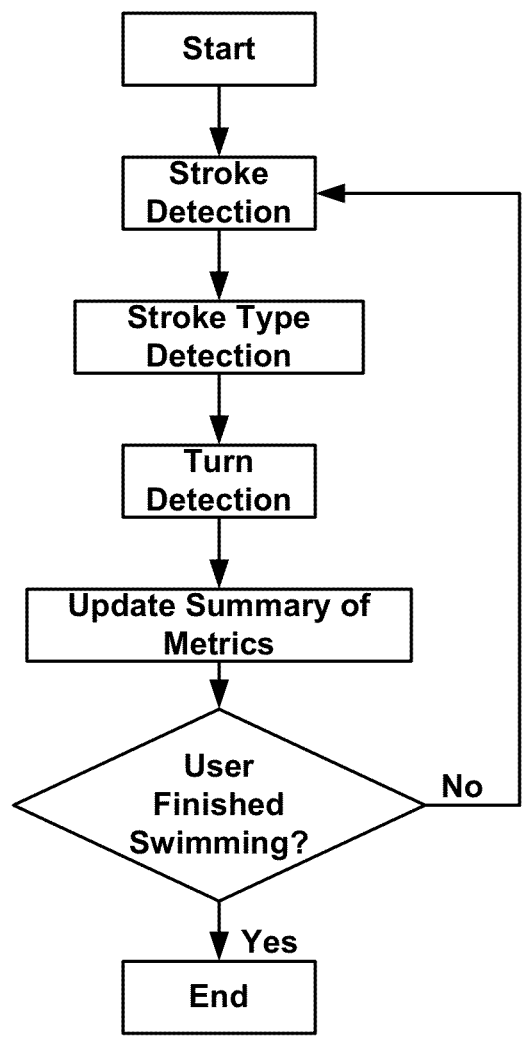
FIG. 15A illustrates an example of a swim detection algorithm using a sequential algorithm flow.

Sequential Approach (See FIG. 15A)

In one embodiment, raw and/or pre-processed sensor signals may first be analyzed by a stroke detector algorithm. The stroke detector algorithm may use temporal peaks (local maxima and/or local minima) in a motion sensor (e.g., accelerometer, gyroscope) as an indication that a stroke has been taken. Then one or more heuristic rules may also be applied to remove peaks that do not represent strokes. For example, the magnitudes of the peaks, temporal distance of two adjacent peaks, peak-to-peak amplitude, and/or morphological characteristics of the peaks (e.g., sharpness) may indicate that certain peaks do not represent strokes. When sensors provide more than one dimensional data, e.g., such as 3-axis accelerometers, or 3 axis motion sensors+altimeter (totaling 4-axis data), timings and relevant sizes of peaks in all axes may be taken into account to determine whether or not the peaks in one or more of the axes are generated by a stroke or not.

If a single peak representing a stroke or group of peaks from multiple data axes representing strokes are observed, features may be extracted from a segment of data that are obtained from the time between when the previous peak is detected and when the current peak is detected. Features include, but are not limited to, maximum and minimum values, number of ripples in the segment, powers measured in various metrics, e.g., L1 power and L2 power, standard deviation, mean, etc. The extracted features may then be put through a machine learning system where the system coefficients are computed off-line (supervised learning) or are adapted as the user uses the biometric monitoring device (unsupervised learning). The machine learning system may then return a stroke classification for each detected stroke.

The turn-detector algorithm may search for sudden changes in motion by calculating derivatives, moving average, and/or using high-pass filtering on the signals of the sensors (the sensors including, but not limited to, those listed in this disclosure). Principal Component Analysis (PCA) can also and/or alternatively be performed on the signal(s). If one principle component is different from the sub-sequential one, then it may be determined that a turn occurred. Whole or partial coefficients of a transform, such as the Fast Fourier Transform (FFT) may be used as features as well. Parametric models such as Autoregressive (AR) models may also be used. Time-varying model parameters may then be estimated using Linear Prediction Analysis (LPA), Least Mean Squares filtering (LMS), Recursive Least Squares filtering (RLS), and/or Kalman filtering. Estimated model parameters are then compared to determine if there is an abrupt change in their values.

In one embodiment, the skill level and/or swimming styles (e.g., speed) of the swimmer may be inferred from sensor data, and then used in turn detection. For example, advanced swimmers typically have more powerful strokes (i.e., large accelerometer peak magnitudes) and take fewer strokes to complete a lap. Therefore, metrics that estimate the swimmer's skill level or characteristics may be used in a turn detection algorithm. These metrics may include, but are not limited to averaged motion signals, or integrated motion signals in particular arm movements, estimated heading speed, and detected patterns of an advanced swimmer in motion signals. The swimmer's skill level or other characteristics may also be determined through user input. For example, the user may input that they are an advanced, intermediate, or beginner swimmer.

One or many (combined) features from these analyses may be used to detect if a given data sample, and/or neighboring data samples, have characteristics of a turn. To obtain the optimal combination of the features and decision boundary, one can utilize machine learning techniques such as logistic regression, decision tree, neural nets, etc.

In some embodiments, if a turn is detected, the swimming data accrued since the previous turn may be summarized, such as the number of strokes, stroke type for each stroke and for the lap, split time, etc. If no turn is detected, the stroke counter and type may be updated. Unless the user quits swimming, the algorithm may go back to stroke count detection.

Figure 15B:
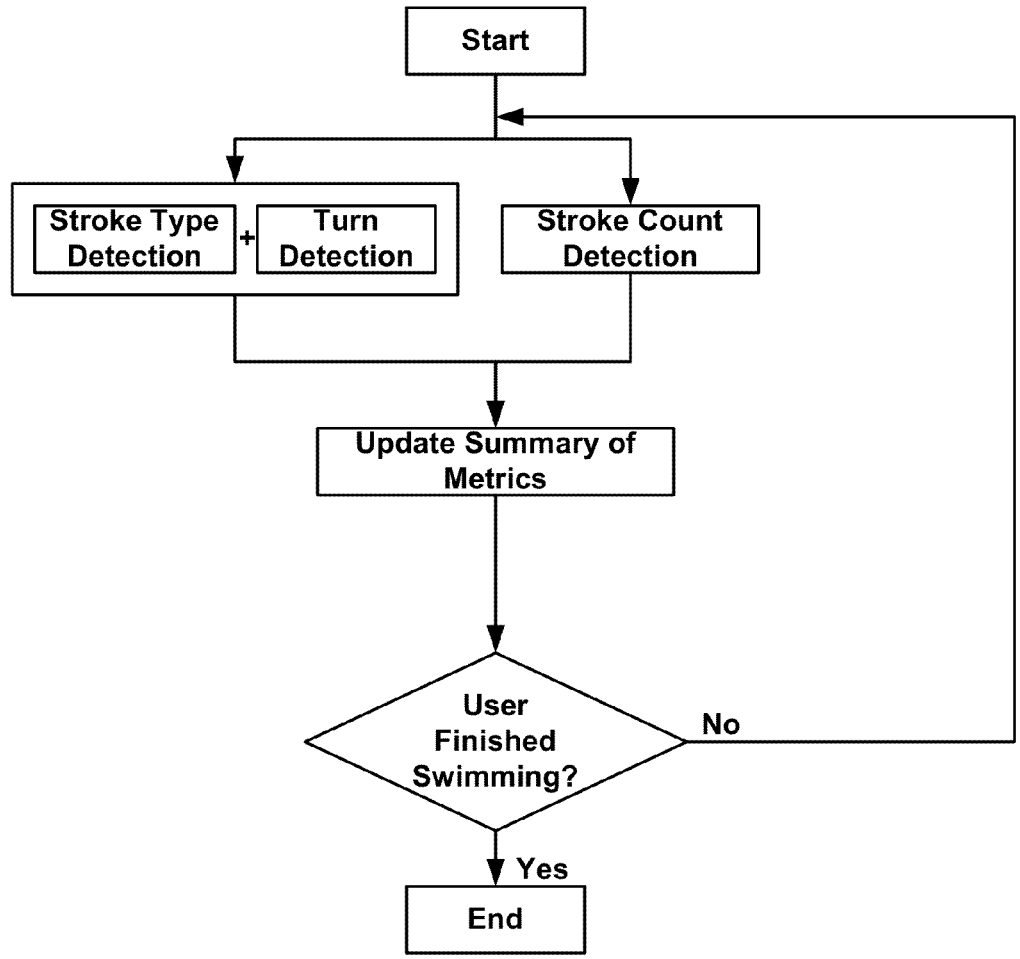
FIG. 15B illustrates an example of a swim detection algorithm which uses a parallel algorithm flow.

Parallel Approach (See FIG. 15B)

In the parallel approach, some or all of the three functional components may be executed in parallel. For example, stroke-type detection and turn detection may be performed jointly, while stroke count detection is run independently.

In such embodiments, two functional components, stroke-type and turn detection, may be implemented in a single algorithm that simultaneously detects stroke-types and turns. For example, a classifier of swimming stroke types, e.g., movement analysis that detects free style strokes, breast stroke strokes, back strokes, butterfly strokes, and of turn types (e.g. tumble turn, flip turn, two hand touch) may return a detected type of stroke or a type of detected turn. During the detection, temporal as well as spectral features may be extracted. A moving window may first be applied to multiple axes of data. Statistics of this windowed segment may then be computed, namely, maximum and minimum value, number of ripples in the segment, powers measured in various metrics (e.g., L1 power and L2 power, standard deviation, mean). Independent component analysis (ICA) and/or principal component analysis (PCA) can be applied as well to find any hidden signals that better represent turn-type and stroke-type characteristics. Temporal features may then be computed from this (potentially improved) signal representation. For temporal features, various nonparametric filtering schemes, low-pass filtering, band-pass filtering, high-pass filtering, may be applied to enhance desired signal characteristics.

Spectral analysis such as FFT, wavelet transform, Hilbert transform, etc., may be applied to this windowed segment as well. Whole or partial transform coefficients may be chosen as features. Parametric models such as AR, moving average (MA), or ARMA (autoregressive and moving average) models may be used, and the parameters of such a model may be found via autocorrelation and/or partial autocorrelation, or LPA, LMS, RLS, or Kalman filter. The entire or part of estimated coefficients may be used as features.

Different lengths of moving average windows may be run in parallel, and provide features listed above, and the whole or part of the features may be utilized as features as well.

Machine-learned coefficients (supervised learning) may then be applied to these extracted features. One or more machine learning techniques, namely multiple layers of binomial linear discriminant analysis (e.g., logistic regression), multinomial logistic regression, neural net, decision tree/forest, or support vector machine, can be trained, and then used.

As the window of interest moves, the features may be extracted and these newly-extracted features will return either a stroke type or detected turn via a machine learning system.

The stroke detector algorithm may run in parallel independent of stroke type and turn detection. Temporal peaks of raw or pre-filtered sensor signals may be detected and chosen by heuristic rules.

At the summarizing stage (the stage where metrics regarding the swim may be determined, displayed, and/or stored) of the algorithm, post-processing may be applied to the sequence of stroke type and turn detections. If a turn is confirmed with certain confidence, the swimming metric data from the previous turn may be summarized along with stroke counts detected. If no turn is confirmed, the moving average window may proceed. Until the user stops swimming, the algorithm may continue to update swimming metrics regarding the exercise of the user, including, but not limited to, a total number of turns, total number of laps, total number of strokes, average strokes per lap, number of strokes in the last lap, the change in number of strokes per lap, etc.

Figure 15C:
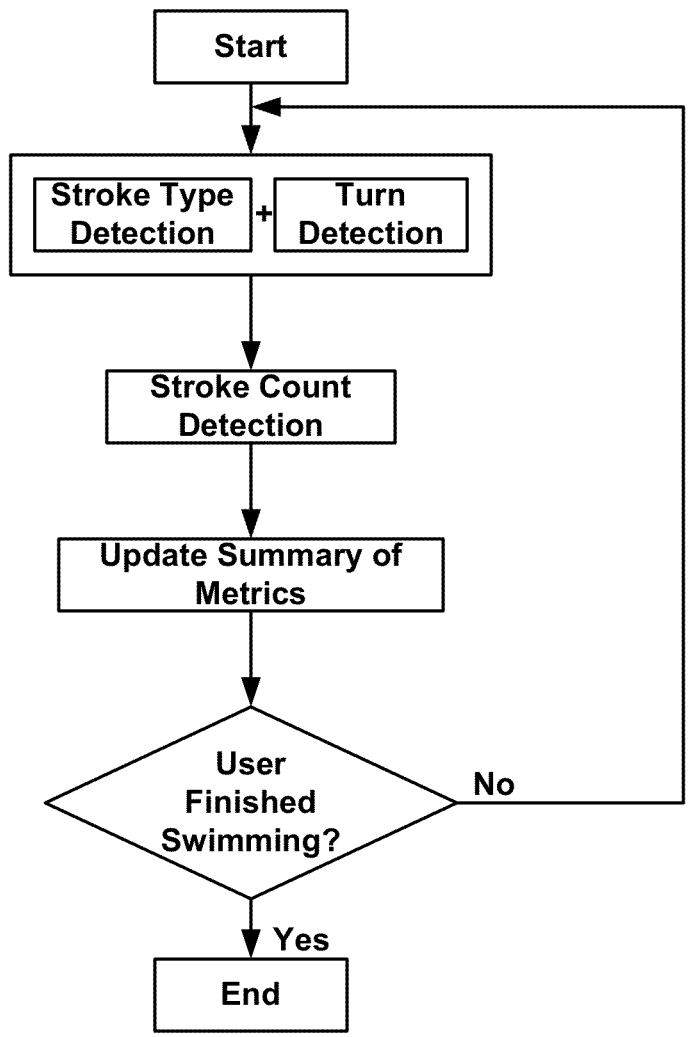
FIG. 15C illustrates an example of a swim detection algorithm which uses a hybrid of sequential and parallel algorithm flow.
Figure 15D:
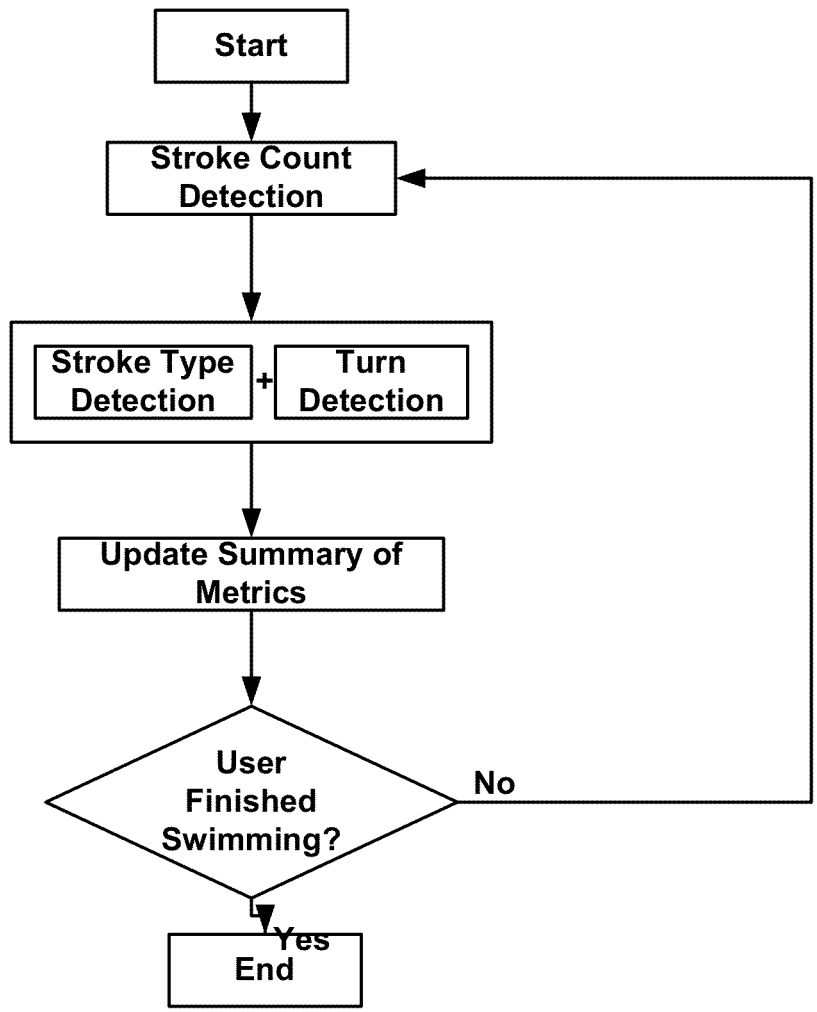
FIG. 15D illustrates an example of a swim detection algorithm which uses a hybrid of sequential and parallel algorithm flow.

Hybrid Approach (See FIGS. 15C and 15D)

In a hybrid approach, the stroke type and stroke count detection may be run in parallel, followed by turn detection.

Stroke-type detection may return a stroke type via machine learned coefficients. A first moving window may take segments of sensor signals. Then features, either entire features or a subset of the moving window features listed in herein, may be extracted. The machine learning coefficients, trained off-line, may then be applied to the features to determine which stroke-type generated the given segments of sensor signals.

Along with stroke type detection, stroke count detection may be run simultaneously.

Once the stroke type and counts are detected, turn detection may be performed with either the entire feature or a subset of the features listed.

If a turn is detected, completion of a lap may be recorded in the swimming summary metrics of the user. A post process may be applied to detected stroke types to determine the most prominent stroke type for the completed lap. Then the algorithm may move to the stroke-type and count detection stages unless the user stops swimming. If no turn is detected, the algorithm may continue updating stroke types and counts of the current lap until a turn is detected.

Blood Glucose Level and Heart Rate

Biometric monitoring devices that continuously measure biometric signals may provide meaningful information on preconditions of, progress towards, and recoveries from diseases. Such biometric monitoring devices may have sensors and run algorithms accordingly to measure and calculate biometric signals such as heart rate, heart rate variability, steps taken, calories burned, distance traveled, weight and body fat, activity intensity, activity duration and frequency, etc. In addition to the measured biometric signals, food intake logs provided by users may be used.

In one embodiment, a biometric monitoring device may observe heart rate and its changes over time, especially before and after a food intake event or events. It is known that heart rate is affected by blood sugar level, whereas it is well known that high blood sugar level is a pre-diabetic condition. Thus, mathematical models that describe the relation between time elapsed (after food intake) and blood sugar level may be found via statistical regression, where data are collected from normal, pre-diabetic, and diabetic individuals to provide respective mathematical models. With the mathematical models, one may predict whether an individual with specific heart rate patterns is healthy, pre-diabetic, or diabetic.

Knowing that many heart failures are associated with pre-diabetic or diabetic conditions, it is possible to further inform users of biometric monitoring devices with possible heart failures, e.g., coronary heart disease, cerebrovascular disease and peripheral vascular disease etc., of such risks based on their biometric data.

Users' activity intensity, type, duration, and frequency may also be taken into account, when developing the mathematical models, as an argument that controls "probability" of the disease onset, using recommended exercise guidelines such as guidelines provided by American Heart Association (http://www.heart.org/). Many guidelines on nutrition and weight management are also available in academia and to the general public to prevent cardiovascular and diabetic disease. Such guidelines may be incorporated into the mathematical models with the user data accumulated over time, such as ingredients of the food that the users consumed, and weight and body fat trends.

If users have set their family members as their friends on a social network site, which stores and displays biometric data, the likelihood of the family members getting a disease may also be analyzed and the users informed of the results.

In addition to informing users regarding a potential development of disease, recommended life-style including exercise regime and recipes with healthier ingredients and methods of preparation may be provided to the users.

Unification of Grocery Shopping, Cooking, and Food Logging

Grocery Organizing and Recipe Recognition System

Receipts from grocery shopping may contain copious information, especially regarding an individual's eating habits. A novel system that combines information from grocery store receipts with an individual's biometric data, as collected by a biometric monitoring device, for example, is presented here. The system may collect and analyze data (information) regarding an individual, and may then recommend options that may change the individual's life-style so as to improve their health. The implementation of this system may involve cloud computing, hardware platform development for sensing and interface, and mobile/website site development.

In one embodiment, when a user checks out at a grocery store, the list of groceries (as obtained from the receipt or, for example, from an email receipt or invoice) may be transmitted automatically to a remote database (e.g., a cloud server), that may also store the user's biometric data. When the user gets home and organizes items in their refrigerator and/or pantry, an app on their smart phone/watch may recommend which items in the pantry or refrigerator to throw away based on historical data on food items (e.g., if food items are expired or likely to have gone bad). Alerts indicating when food has expired or that it should be consumed in the near future to avoid spoilage may be automatically sent to the user independently of such activity. For example, these alerts may be sent out to the user whenever a certain threshold has been met (e.g., in two days the milk will expire). The alerts may also be sent to the user through means other than through a smart phone/watch. For example, the alerts may be presented to the user through a web interface, through email, through an alert on a laptop computer, on a tablet computer, desktop computer, or any other electronic device which is in direct or indirect communication with the computer which maintains and/or analyzes the database of food Using the updated list of food items, and based on the user's historical food consumption data, the app may recommend recipes to the user. In one embodiment, preference may be given to recipes that use the items what should be eaten first (e.g., before they expire, go bad, or become less fresh faster than other ingredients). To recommend the optimal recipe that is nutritionally balanced, correctly portioned, and tailored to the user's activity, the app may also analyze the user's activity data as well. For example, if the user lifted weights in the morning, high-protein meals may be recommended. In another example, if the user was not very active, the size of the recipe may be decreased to lower the number of calories that the final meal contains.

Note that these strategies may be applied to multiple users that either share the same food and/or meals. For example, a combined food database may be created for a household so that if one member of the house got eggs and another member of the house got milk from the grocery store that both eggs and milk would be represented in the food database. Similarly, the nutritional preferences (e.g., vegetarian, allergic to certain foods, etc.), activity, basal metabolic rate, and total calorie burn may be used to form a recommendation on what food/recipe to prepare and/or purchase.

Biometric signals including, but not limited to, heart rate and heart rate variability may provide indications of pre-conditions of diseases. This information may be used to recommend that the user purchase, consume, and/or prepare particular foods so as to reduce their risk of the disease(s) for which they have the pre-conditions. For example, if a user has a precondition for cardiac problems, it may be recommended that they purchase more vegetables, consume less fatty foods, and prepare food in methods which require less oil (e.g., not deep frying).

Control "Smart Appliance"

In another embodiment, various appliances may all be Wi-Fi enabled, and may communicate with servers. Since the app (which may be connected to the appliances via, for example, the cloud or the Internet) may know which food items the refrigerator contains, the app may communicate with the refrigerator to lower or raise the temperature of the refrigerator depending on the food items. For example, if many of the food items are more sensitive to cold, such as vegetables, the refrigerator may be instructed to raise the temperature. The app may also directly communicate with the refrigerator as well via Bluetooth, BTLE, or NFC.

Food Logging

The app may also provide items to log in as the user's food based on a grocery shopping list (which may, for example, be a list maintained within the app) and food recipes that the app recommended. In case of precooked meals (e.g., frozen dinner) or produce that does not require any further processing before being eaten, the user may simply input their serving size (or in the case that the user eats the whole meal, the user may not need to enter a serving size), and then the food logging will be completed. Since the grocery list or receipt provides the exact brand and maker of certain foods, more accurate nutritional information may be logged into the user's account.

When a user logs a food item that is cooked by following a recipe suggested by the app, the app may calculate nutritional information from the ingredients and cooking procedure. This may provide more accurate estimate of calorie intake than a simple categorization of the end product/meal, since many recipes exist to prepare a particular type of food, e.g., meatballs for pasta may be made with beef, turkey, pork, etc., and may include varying degrees of carbohydrates.

Sport Metric Acquisition Using a Sensor Device

In some embodiments, a sensor may be mounted on a racket, e.g., tennis racket, to help to measure the different strokes of the player. This may be applicable to most, if not all, racket sports including, but not limited to, tennis, racquetball, squash, table tennis, badminton, lacrosse, etc., as well as sports played with a bat like baseball, softball, cricket, etc. Similar techniques may also be used to measure different aspects of golf. Such a device can be mounted on the base of the racket, on the handle or on the shock absorber typically mounted on the strings. This device may have various sensors like an accelerometer, gyroscope, magnetometer, strain sensor, and/or microphone. The data from these sensors may either be stored locally or transmitted wirelessly to a host system on a smartphone or other wireless receiver.

In some embodiments of a biometric monitoring device, a wrist mounted biometric monitoring device including an accelerometer, gyroscope, magnetometer, microphone, etc. may perform similar analysis of the user's game or motions. This biometric monitoring device may take the form of a watch or other band worn on the user's wrist. Racket- or bat-mounted sensors that measure or detect the moment of impact between the bat or racket and the ball and wirelessly transmit such data to the wrist-mounted biometric monitoring device may be used to improve accuracy of such algorithms by accurately measuring the time of impact with the ball.

Both wrist and racket-/bat-mounted devices may help measure different aspects of the user's game including, but not limited to, stroke-type (forehand, backhand, serve, slice, etc.), number of forehands, number of backhands, ball spin direction, topspin, service percentage, angular velocity of racket head, backswing, shot power, shot consistency, etc. The microphone or the strain sensor may be used in addition to the accelerometer to identify the moment at which the ball impacts the racket/bat. In cricket and baseball, such a device may measure the backswing, the angular velocity of the bat at the time of impact, the number of shots on the off-side vs. leg-side (cricket). It may also measure the number of swings and misses and the number of defensive vs. offensive strokes. Such a device may also have a wireless transmitter to transmit such statistics in real time to a scoreboard or to individual devices held by spectators.

The wrist- or racket-mounted device may have a small number of buttons (e.g., two) that may be used by the player to indicate when a volley is won or when an unforced error occurs. This will allow the algorithm to calculate the fraction of winners and unforced errors that are forehands vs. backhands. The algorithm may also keep track of the number of aces vs. double-faults in tennis. If both players use such a system, the system may also automatically keep track of the score.

Bicycle Handlebar Based ECG

In some embodiments of biometric monitoring devices, a user's heart rate may be monitored using an electrode in contact with the left hand and an electrode in contact with the right hand (an ECG heart rate measurement). As riding a bicycle requires the user to make hand contact with either side of the handlebars, this particular activity is well suited to tracking user heart rate using ECG techniques. By embedding electrodes in the handlebars or handlebar grips or tape, the user's heart rate may be measured whenever the user is holding the handlebars. For bicycles that have grips (as opposed to using handlebar tape), electrodes may be incorporated into a special grip that may be used to replace the existing grips, e.g., the factory-installed grips, which are typically non-conductive. The left and right grips may be electrically connected to electronics that measure the ECG signal, using a wire, for example. In the case that the handlebars themselves are conductive, the handlebars may be used to electrically connect one of the grips to the electronics that measure the ECG signal. The electronics that measure the ECG signal may be incorporated into one or both of the grips. Alternatively, the electronics that measure the ECG signal may be located in a separate housing. In one embodiment, this separate housing may be mounted on the bicycle handlebar or stem. It may have functions and sensors that typical bicycle computers have (e.g., speed sensor, cadence sensor, GPS sensor). It may also have atypical sensors such as a wind speed sensor, GSR sensor(s), and accelerometer sensor (potentially also incorporated into the handlebars). This embodiment may use techniques described in this disclosure to calculate activity metrics including, but not limited to, calorie burn, and transmit these metrics to secondary and tertiary device(s) (e.g. smartphones and servers).

Electrodes for the ECG may be incorporated into parts of the bike or accessories other than into grip tape and handlebar grips such as into gloves, brake hoods, brake levers, or the handlebars themselves. These electrodes or additional electrodes may be used to measure GSR, body fat and hydration in addition to, or in alternative to, heart rate. In one example, the user's heart rate may be measured using conductive threads (used as ECG electrodes) sewn into grip tape installed on the handlebar. The grip tape electrodes may be connected to a central bike computer unit that contains electronics to measure GSR, hydration, and/or heart rate. The biometric monitoring device may display this information on a display. If the user's hydration or heart rate exceeds a certain threshold, the user may be alerted to drink more, drink less, increase intensity or decrease intensity. In the case that the bike computer measures only one or two of GSR, hydration or heart rate, algorithms may be used to estimate metrics which that cannot be measured directly. For example, if the biometric monitoring device can only measure heart rate and duration of exercise, a combination of heart rate and duration of exercise may be used to estimate hydration and alert the user when they should drink. Similarly, heart rate and exercise duration may be used to alert the user when they should eat or drink something other than water (e.g., a sports drink).

Indirect Metric Estimation

Bicycle computers typically measure a variety of metrics including, but not limited to, speed, cadence, power, and wind speed. In the case that the portable monitoring device does not measure these metrics or is not in communication with devices which may be able to supply these metrics, these and other metrics may be inferred using the sensors that the portable biometric monitoring device does have. In one embodiment, the portable biometric monitoring device may measure heart rate. It may use this measurement to infer/estimate the amount of power that the user is outputting. Other metrics such as the user's age, height, and weight may help inform the power measurement. Additional sensor data such as GPS-measured speed, altitude gain/descent, bicycle attitude (so as the measure the incline or decline of a slope), and accelerometer signals may be used to further inform the power estimate. In one embodiment, an approximately linear relationship between heart rate and power output may be used to calculate the user's power output.

In one embodiment, a calibration phase may occur where the user takes data from the portable biometric monitoring device and a secondary device that may be used during calibration as a baseline but not be used at a later time (e.g., a power meter). This may allow a relationship between sensor data measured by the portable monitoring device and sensor data measured by the secondary device data to be determined. This relationship may then be used when the secondary device is not present to calculate estimated values of data that is explicitly provided by the secondary device but not by the biometric monitoring device.

Activity Based Automatic Scheduling

In one embodiment, the day's travel requirements (to work, from work, between meetings) may be scheduled for the user based on the information in their calendar (or emails or text messages etc.), with the aim of meeting daily activity goal(s)

or long term activity goal(s). The user's historical data may be used to help plan both meeting the goal(s) and also the transit time required. This feature may be combined with friends or colleagues. The scheduling may be done such that a user may meet a friend along the way as they walk to work, or meet a colleague on the way to a meeting (the user might need to set a rendezvous point, though). If there is real-time communication between biometric monitoring devices of the user and the user's friend, the user may be directed to walk a longer route if data from the friend's biometric monitoring device indicates that their friend is running late.

In another embodiment, walking/running/fitness routes may be suggested to the user based (in whole or in part) on their proximity to the user. The data for such recommendations could also or additionally be based on GPS info from other users. If there is real-time communication, the user may be directed to a busy route or a quiet route as preferred. Knowing heart rate and basic fitness information about other users may allow the system to suggest a route to match a user's fitness level and the desired exercise/exertion level. Again this information may be used for planning/guiding a user to longer term activity/fitness goals.

Location/Context Sensing and Applications

Through one or more methods, embodiments of the biometric monitoring devices disclosed herein may have sensors that can determine or estimate the location and or context (e.g. in a bus, at home, in a car) of the biometric monitoring device. Purpose-built location sensors such as GPS, GLONASS, or other GNSS (Global Navigation Satellite System) sensors may be used. Alternatively, location may be inferred, estimated or guessed using less precise sensors. In some embodiments in which it is difficult to know the user's location, user input may aid in the determination of their location and or context. For example, if sensor data makes it difficult to determine if a user was in a car or a bus, the biometric monitoring device or a portable communication device in communication with the biometric monitoring device or a cloud server which is in communication with the biometric monitoring device may present a query to the user asking them if they took the bus today or took a car. Similar queries may occur for locations other than vehicular contexts. For example, if sensor data indicate that the user completed a vigorous workout, but there is no location data that indicates that the user went to a gym, the user may be asked if they went to the gym today.

Vehicular Transportation Detection

In some embodiments, sensors of the biometric monitoring device and/or a portable electronic device in communication with the biometric monitoring device and/or a server which communicates with the biometric monitoring device may be used to determine what type of vehicle (if any) the user is, or was, in. Note that in the embodiments below, a sensor in one or more biometric monitoring devices and/or portable electronic devices may be used to sense the relevant signal. Also note that while specific network protocols such as WiFi or Bluetooth may be used in the following descriptions, one or more alternative protocols such as RFID, NFC, or cellular telephony may also be used.

In one embodiment, the detection of a Bluetooth device associated with a vehicle may be used to infer that the user is in a vehicle. For example, a user may have a car that has a Bluetooth multimedia system. When the user gets close enough to their car for a long enough period of time, the sensor device may recognize the Bluetooth identification of the multimedia system and assume that the user is in the car. Data from other sensors may be used to corroborate the assumption that the user is in the vehicle. Examples of data or signals from other sensors that may be used to confirm that the user is in a car include a GPS speed measurement that is higher than 30 mph and accelerometer signals that are characteristic of being in a car. Information intrinsic to the Bluetooth ID may be used to determine that it is a Wi-Fi router of a vehicle or type of vehicle. For example, the Bluetooth ID of a router in a car may be "Audi In-Car Multimedia." The keyword "Audi" or "Car" may be used to guess that the router is associated with a vehicle type of "car." Alternatively, a database of Bluetooth ID's and their associated vehicles may be used.

In one embodiment, a database of Bluetooth ID's and their associated vehicles may be created or updated by the user of a biometric monitoring device or through portable communication device data. This may be done with and/or without the aid of user input. In one embodiment if a biometric monitoring device can determine whether or not it is in a vehicle, vehicle type, or specific vehicle without the use of Bluetooth ID, and it encounters a Bluetooth ID that moves with the vehicle, it may send the Bluetooth ID and information regarding the vehicle to a central database to be catalogued as a Bluetooth ID that corresponds with a vehicle. Alternatively, if a user inputs information about the vehicle they are in or were in at a previous point in time and there is a Bluetooth ID that was encountered during or close to the time that the user indicated they were in the vehicle, the Bluetooth ID and vehicle information may be sent to a central database and associated with one another.

In another embodiment, the detection of a Wi-Fi device associated with a vehicle may be used to infer that the user is in that vehicle or type of vehicle. Some trains, buses, airplanes, cars, and other vehicles have Wi-Fi routers in them. The SSID of the router may be detected and used to infer or aid an inference that a user is in a specific vehicle or type of vehicle.

In one embodiment, a database of SSID's and their associated vehicles may be created or updated with the user of a biometric monitoring device or through portable communication device data. This may be done with and/or without the aid of user input. In one embodiment, if a biometric monitoring device can determine whether or not it is in a vehicle, vehicle type, or specific vehicle without the use of an SSID, and it encounters an SSID that moves with the vehicle, the biometric monitoring device may send the SSID and information regarding the vehicle to a central database to be catalogued as an SSID that corresponds with a vehicle. Alternatively, if a user inputs information about the vehicle they are in or were in at a previous point in time and there is an SSID that was encountered during or close to the time that the user indicated they were in the vehicle, the SSID and vehicle information may be sent to a central database and associated with one another.

In another embodiment of a biometric monitoring device, location sensors may be used to determine the track of a user. This track may then be compared to a database of routes for different modes of transit. Modes of transit may include, but are not limited to walking, running, biking, driving, taking a bus, taking a train, taking a tram, taking the subway, and/or motorcycling. If the user's track corresponds well with a route of a specific mode of transit, it may be assumed that the user used that mode of transit for the period of time that it took them to traverse the route. Note that the speed with which the route or sections of the route were completed may improve the guess of the mode of transit. For example, a bus and a car may both be able to take the same route, but the additional stopping of the bus at bus stops may allow the device to determine that the user was taking a bus rather than a car.

Similarly, the discrimination between biking and driving a route may be aided by the typical difference of speed between the two. This difference in speed may also depend on the time of day. For example, some routes may be slower by car during rush hour.

In another embodiment, a biometric monitoring device may be able to detect that the user is in or near a vehicle based on measurements of the magnetic field of vehicle. In some embodiments, the magnetic field signature of a location typically associated with the vehicle (e.g., train station, subway station, bus stop, car garage) may also be used to infer that the user is currently in, will be, or has been in a vehicle. The magnetic field signature may be time invariant or time varying.

If it is determined that the user was indeed in a vehicle for a period of time, other metrics about the user may be modified to reflect such a status. In the case that the biometric monitoring device and/or portable electronic device can measure activity metrics such as steps taken, distance walked or run, altitude climbed, and/or calories burned, these metrics may be modified based on information about vehicular travel. If any steps taken or altitude climbed were incorrectly logged during the time that the user is in a vehicle, they may be removed from the log of metrics about the user. Metrics derived from the incorrectly logged steps taken or altitude climbed such as distance travelled and calories burned may also be removed from the log of metrics about the user. In the case that it can be determined in real-time or near real-time whether or not the user is in a vehicle, the sensors detecting metrics which should not be measured while in a vehicle (e.g. steps taken, stairs climbed) may be turned off or algorithms which are used to measure these metrics may be turned off to prevent incorrectly logged metrics (as well to save power). Note that metrics regarding vehicle use such as type of vehicle taken, when it was taken, which route was taken, and how long the trip took may be recorded and used later to present the user with this data and/or to correct other activity and physiological metrics about the user.

Location Sensing Using Bluetooth

Methods similar to those described above may also be used by a biometric monitoring device to determine when the user comes into proximity of static locations. In one embodiment, Bluetooth ID's from computers (e.g., tablet computers) at restaurants or stores may be used to determine the user's location. In another embodiment, semi-fixed Bluetooth ID's from portable communication devices (e.g., smartphones) may be used to determine a user's location. In the case of semi-fixed Bluetooth ID sources, multiple Bluetooth ID's may be need to reach an acceptable level of confidence of the location of the user. For example, a database of Bluetooth ID's of the coworkers of a user may be created. If the user is within range of several of these Bluetooth ID's during typical working hours, it may be assumed that the user is at work. The detection of other Bluetooth ID's may also be used to record when two users meet up. For example, it may be determined that a user went for a run with another user by analyzing pedometer data and Bluetooth ID's. Similar such concepts are discussed in further detail in U.S. Provisional Patent Application No. 61/948,468, filed Mar. 5, 2014, and previously incorporated by reference with regard to such concepts.

Uncertainty Metric for GPS Based on Location

When fusing sensor signals with GPS signal to estimate informative biometrics, such as steps, live pace, speed, or trajectory of trips, quality of the GPS signal is often very informative. However, GPS signal quality is known to be time-varying, and one of the factors that affects the signal quality is environmental surroundings.

Location information may be used to estimate GPS signal quality. A server may store a map of area types, where the area types are pre-determined by number and kind of objects that deteriorate GPS signals. The types may, for example, be: large building area, small building area, open area, side-by-water area, and forested area. These area types are then queried when GPS sensor gets turned on with its very first few location estimates, which are expected to be rough and inaccurate. With the rough GPS estimates of the location, possible types of areas may be returned, and these area types may then be taken into account in the calculation of the GPS signal quality and reliability.

For example, if a user is in or near an urban canyon (an area surround by tall buildings) such as downtown San Francisco, a low certainty may be associated with any GNSS location measurements. This certainty may be used later by algorithms that attempt to determine the user's track, speed, and/or elevation based on, at least in part, GPS data.

In one embodiment, a database of location and GPS signal quality may be created automatically using data from one or more GNSS sensors. This may be automatically performed by comparing the GNSS tracks with a map of streets and seeing when the GNSS sensors show characteristics of a user travelling along a street (e.g., having a speed of 10 mph or higher), but their track is not located on a road. The database of GPS certainty based on approximate location may also be inferred from maps showing where there are tall buildings, canyons, or dense forests.

Location Sensing Using Vehicular GNSS and/or Dead Reckoning

Many vehicles have integrated GNSS navigation systems. Users of vehicles that don't have integrated GNSS navigations systems often buy a GNSS navigation system for their car that is typically mounted non-permanently in the driver's field of view. In one embodiment, a portable biometric monitoring device may be able to communicate with the vehicle's GNSS system. In the case where the portable biometric monitoring device is also used to track location, it may receive location information from the vehicle GNSS. This may enable the biometric monitoring device to turn off its own GNSS sensor (in the case that it has one), therefore reducing its power consumption.

In addition to GNSS location detection, a vehicle may be able to transmit data about its steering wheel orientation and/or its orientation with respect to the earth's magnetic field in addition to its speed as measured using the tire size and tire rotational velocity. This information may be used to perform dead-reckoning to determine a track and/or location in the case that the vehicle does not have a GNSS system or the vehicle's GNSS system cannot get a reliable location measurement. Dead-reckoning location information may supplement GNSS sensor data from the biometric monitoring device. For example, the biometric monitoring device may reduce the frequency with which it samples GNSS data and fill in the gap between GNSS location data with locations determined through dead reckoning.

Step Counter Data Fusion with Satellite-Based Location Determination

In some implementations of a biometric monitoring device, data from various different sensors may be fused together to provide new insights as to activities of the wearer of the biometric monitoring device. For example, data from an altimeter in the biometric monitoring device may be combined with step count data obtained by performing peak detection analysis on accelerometer data from an accelerometer of the biometric monitoring device to determine when the wearer of the biometric monitoring device is, for example, climbing stairs or walking uphill (as opposed to riding an elevator or an escalator or walking across flat ground).

In another example of sensor data fusion, data from a step counter such as that discussed above may be combined with distance measurements derived from GPS data to provide a refined estimate of total distance traveled within a given window. For example, GPS-based distance or speed data may be combined with step-counter-based distance or speed (using steps taken multiplied by stride length, for example) using a Kalman filter in order to obtain a refined distance estimate that may be more accurate than either the GPS-based distance or speed measurement or the step-counter-based distance or speed measurement alone. In another implementation, a GPS-based distance measurement may be filtered using a smoothing constant that is a function of the step rate as measured by, for example, an accelerometer. Such implementations are discussed further in U.S. Provisional Patent Application No. 61/973,614, filed Apr. 1, 2014, which was previously incorporated herein by reference in the "Cross-Reference to Related Applications" section and which is again hereby incorporated by reference with respect to content directed at distance or speed estimation refinement using data from satellite-based location systems and step count sensors.

Biometric and Environmental/Exercise Performance Correlation

Some embodiments of portable monitoring devices described herein may detect a variety of data including biometric data, environmental data, and activity data. All of this data may be analyzed or presented to a user to facilitate analysis of or correlation between two or more types of data. In one embodiment, a user's heart rate may be correlated to car speed, biking speed, running speed, swimming speed or walking speed. For example, the user may be presented with a graph that plots biking speed on the X axis and heart rate on the Y axis. In another example, a user's heart rate may be correlated to music that they were listening to. The biometric monitoring device may receive data regarding what music the user was listening to through a wireless connection (e.g., Bluetooth) to a car radio. In another embodiment, the biometric monitoring device may also function as a music player itself, and therefore can record which song was played when.

Weight Lifting Aid

Without the aid of a personal trainer or partner, it may be difficult to do a weight-lifting routine properly. A portable biometric monitoring device may aid a user in completing a weight lifting routine by communicating to the user how long they should hold up each weight, how quickly they should lift it, how quickly they should lower it, and how many repetitions of each lift to perform. The biometric monitoring device may measure the user's muscle contractions using one or more EMG sensors or strain sensors. The user's muscle contractions may also be inferred by measuring vibrations of one or more body parts (for example using an accelerometer), sweat (e.g., using a GSR sensor), rotation of one or multiple body parts (e.g., using a gyroscope), and/or a temperature sensor on one or more body parts. Alternatively, a sensor may be placed on the weight lifting apparatus itself to determine when the using is lifting, with how much speed they are lifting or lowering, how long they are lifting for, and how many repetitions of lifts they have performed.

In one embodiment, if the biometric monitoring device or weight lifting apparatus detects that the user is approaching their failure limit (when the user can no longer support the weight), the weight lifting apparatus may automatically lift the weight or prevent the weight from being lowered. In another embodiment, a robot in communication with the biometric monitoring device or weight lifting apparatus may automatically lift the weight or prevent the weight from being lowered. This may allow the user to push themselves to their limit without needing a partner/spotter (to lift the weight in case of failure) and without risking injury from dropping the weight.

Glucose Level Monitoring Aid

In some embodiments, a portable biometric monitoring device may be configured to aid users who need to monitor their glucose levels (e.g., diabetics). In one embodiment, the portable biometric monitoring device may indirectly infer a user's glucose level or a metric related to the user's glucose level. Sensors other than those typically used in monitoring glucose monitoring (using continuous or discrete finger-prick types of sensors) may be used in addition to, as an alternative to, or as an aid to the typical glucose monitoring methods. For example, an biometric monitoring device may alert the user that they should check their blood glucose level based on data measured from sensors on the biometric monitoring device. If the user has performed a certain type of activity for a certain amount of time, their blood glucose level is likely to have decreased, and therefore, the biometric monitoring device may display an alert, create an auditory alert, or vibrate to alert the user that their blood glucose may be low and that they should check it using a typical glucose measurement device (e.g., a finger-prick type glucose monitor). The biometric monitoring device may allow the user to input the glucose level that is measured from the glucose meter. Alternatively, the glucose measurement may be automatically transmitted to the biometric monitoring device and/or a third device in direct or indirect communication with the biometric monitoring device (e.g., a smart phone or server). This glucose measurement may be used to inform the algorithm used by the biometric monitoring device to determine when the next glucose level alert should be delivered to the user. The user may also be able to enter what food they ate, are eating, or are planning to eat into the biometric monitoring device or a device in direct or indirect communication with the biometric monitoring device. This information may also be used to determine when the user should be alerted to check their blood glucose level. Other metrics and sensor data described herein (e.g., heart rate data) may also be used alone or in combination to determine when the user should be alerted to check their blood glucose.

In addition to being alerted when glucose levels should be checked, a biometric monitoring device may also display an estimate of the current glucose level. In another embodiment, data from the biometric monitoring device may be used by a secondary device (e.g., a smart phone or server) to estimate the user's glucose level and/or present this data to the user (e.g., by displaying it on a smartphone, on a webpage, and/or by communicating the data through audio).

A biometric monitoring device may also be used to correlate exercise, diet, and other factors to blood glucose level. This may aid users in seeing the positive or negative effects of these factors on their blood glucose levels. The blood glucose levels with which the activity is correlated to may be measured by the user using a different device (e.g., a finger-prick monitor or continuous blood glucose monitor), by the biometric monitoring device itself, and/or by inferring the blood glucose level or a metric related to the glucose level using other sensors. In some embodiments of biometric monitoring devices, a user may wear a continuous glucose monitoring device and a biometric monitoring device. These two devices may automatically upload data regarding activities and glucose levels to a third computing device (e.g., a server). The server may then analyze the data and/or present the data to the user so that they become more aware of the relationship between their activities and glucose levels. The server may also receive input on the user's diet (e.g., the user may enter what foods they eat) and correlate the diet with glucose levels. By helping the user understand how diet, exercise, and other factors (e.g., stress) affects their blood glucose levels, biometric monitoring devices may aid users who have diabetes.

UV Exposure Detection

In one embodiment, the biometric monitoring device may have the ability to monitor an individual's exposure to UV radiation. UVA and UVB may be measured with one or multiple sensors. For example, a photodiode having a bandpass filter which passes only UVA may detect UVA exposure and a photodiode having a bandpass filter which passes only UVB may detect UVB exposure. The user's skin pigmentation may also be measured using a camera or reflectometer (light emitter and light detector which determines the efficiency with which light is reflected off the skin). Using UVA, UVB, and skin pigmentation data, the biometric monitoring device may provide a user with information regarding the amount of UV exposure they have been subjected to. The biometric monitoring device may also provide estimates or alarms regarding over exposure to UV, potential for sunburn, and potential for increasing their risk of skin cancer.

Screen Power Saving Using User Presence Sensors

The portable biometric monitoring device may have one or more a displays to present information to the user. In one embodiment sensors on the biometric monitoring device may determine the user is using the biometric monitoring device and/or wearing the biometric monitoring device to determine the state of the display. For example, a biometric monitoring device having a PPG sensor may use the PPG sensor as a proximity sensor to determine when the user is wearing the biometric monitoring device. If the user is wearing the biometric monitoring device, the state of the screen (e.g. a color LCD screen) may be changed to "on" or "standby" from its typical state of being off.

Power Conservation with Respect to Satellite-Based Location Determination Systems In some implementations, certain systems included in a biometric monitoring device may consume relatively large amounts of power compared to other systems in the biometric monitoring device. Due to the small space constraints of many biometric monitoring devices, this may seriously affect overall battery charge life for the biometric monitoring device. For example, in some biometric monitoring devices, a satellite-based location determination system may be included. Each time the satellite-based location determination system is used to obtain a position fix using data from the GPS satellite constellation, it uses power drawn from the biometric monitoring device battery. The biometric monitoring device may be configured to alter the frequency with which the satellite-based location determination system obtains a location fix based on data from one or more sensors of the biometric monitoring device. This adaptive location fix frequency functionality may help conserve power while still allowing the satellite-based location determination system to provide location fixes at useful intervals (when appropriate).

For example, if a biometric monitoring device has an ambient light sensor, data from the ambient light sensor may be used to determine whether the lighting conditions indicate that the biometric monitoring device is likely indoors as opposed to outdoors. If indoors, the biometric monitoring device may cause the location fix frequency to be set to a level that is lower than the location fix frequency that may be used when the lighting conditions appear to indicate that the biometric monitoring device is outdoors. This has the effect of decreasing the number of location fixes that are attempted when the biometric monitoring device is indoors and thus less likely to obtain a good location fix using a satellite-based location determination system.

In another example, if motion sensors of the biometric monitoring device indicate that the wearer of the biometric monitoring device is substantially stationary, e.g., sleeping or generally not moving more than a few feet every minute, the location fix frequency of the satellite-based location determination system may be set to a lower level than if the motion sensors indicate that the wearer of the biometric monitoring device is in motion, e.g., walking or running from one location to another, e.g., moving more than a few feet.

In yet another example, the biometric monitoring device may be configured to determine if the biometric monitoring device is actually being worn by a person—if not, the biometric monitoring device may set the location fix frequency to a lower level than if the biometric monitoring device is actually being worn. Such determinations regarding whether or not the biometric monitoring device is being worn may be made, for example, when motion data collected from motion sensors of the biometric monitoring device indicate that the biometric monitoring device is substantially immobile, e.g., not even demonstrating small movements experienced by biometric monitoring devices when the wearer is sleeping or sedentary, or when data, for example, from a heartbeat waveform sensor indicates that no heart rate is detected. For optical heartbeat waveform sensors, if there is little or no change in the amount of light detected by the light detection sensor when the light source is turned on and off, this may be indicative of the fact that the heartbeat waveform sensor is not pressed against a person's skin and that, by inference, the biometric monitoring device is not being worn. Such adaptive satellite-based location determination system fix frequency concepts are discussed in more detail in U.S. Provisional Patent Application No. 61/955,045, filed Mar. 18, 2014, which was previously incorporated herein by reference in the "Cross-Reference to Related Applications" section and which is again hereby incorporated by reference with respect to content directed at power conservation in the context of satellite-based location determination systems.

It is to be understood that biometric monitoring devices, in addition to including the features discussed below in more detail, may also include one or more features or functionalities discussed above or discussed in the various applications incorporated by reference in the above discussion. Such implementations are to be understood as being within the scope of this disclosure.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

Importantly, the present disclosure is neither limited to any single aspect nor embodiment, nor to any combinations and/ or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

What is claimed is:

1. A method of determining a user's heart rate using a worn biometric monitoring device comprising a plurality of sensors including a heartbeat waveform sensor and a motion detecting sensor, the method comprising:
   (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats;
   (b) processing the output data from the motion detecting sensor to determine a periodic component of the output data from the motion detecting sensor, and removing the periodic component from the output data from the heartbeat waveform sensor;
   (c) determining an activity state of the user and from the activity state determining a duty cycle for operating the heartbeat waveform sensor, wherein the duty cycle has (i) an active phase during which the heartbeat waveform sensor is on and collects enough data to determine the user's heart rate and (ii) an inactive phase during which the heartbeat waveform sensor is off and does not provide output data
   (d) operating the heartbeat waveform sensor at the duty cycle;
   (e) determining the user's heart rate; and
   (f) presenting the user's heart rate,. wherein at least operations (a)-(e) are carried out by one or more processors.

2. The method of claim 1, wherein the duty cycle's active phase has a duration of about 5 to 15 seconds for acquiring output data from the heartbeat waveform sensor and determining the user's heart rate, followed by an inactive phase.

3. The method of claim 2, wherein successive active phases are separated by about 1 to 10 minutes.

4. The method of claim 2, wherein the active phase is triggered by receiving user input requesting a heart rate measurement.

5. The method of claim 1, wherein output data from the heartbeat waveform sensor and output data from the motion detecting sensor is collected in (a) for about 5-15 seconds during each minute of the duty cycle.

6. The method of claim 1, further comprising:
   detecting that the user is attempting to read a heart rate; and
   temporarily suspending the duty cycling.

7. The method of claim 1, further comprising:
   analyzing the output data from the motion detecting sensor to infer a low activity level; and
   temporarily suspending the duty cycling.

8. The method of claim 1, wherein the periodic movement detected by the motion sensor is a wearer's limb movements.

9. The method of claim 8, wherein the limb movements are steps, swim strokes, ankle revolutions while bicycling, and leg movements on cardio machines.

10. The method of claim 1, wherein the motion detecting sensor is an accelerometer or a gyroscope.

11. The method of claim 1, wherein the heartbeat waveform sensor comprises a photoplethysmography sensor or an ECG sensor.

12. The method of claim 1, wherein collecting the output data from the heartbeat waveform sensor comprises:
   pulsing a light source in the worn biometric monitoring device at a first frequency; and
   detecting light from the light source at the first frequency.

13. The method of claim 1, wherein presenting the user's heart rate comprises presenting the heart rate on the worn biometric monitoring device.

14. A wearable fitness monitoring device comprising:
   a motion sensor configured to provide output corresponding to motion by a user wearing the fitness monitoring device;
   a heartbeat waveform sensor; and
   control logic comprising instructions for:
   (a) collecting concurrent output data from the heartbeat waveform sensor and output data from the motion detecting sensor, wherein the output data from the heartbeat waveform sensor provides information about the user's heart rate and wherein the output data from the motion detecting sensor provides information about the user's periodic physical movements other than heartbeats;
   (b) processing the output data from the motion detecting sensor to determine a periodic component of the output data from the motion detecting sensor, and removing the periodic component from the output data from the heartbeat waveform sensor;
   (c) determining an activity state of the user and from the activity state determining a duty cycle for operating the heartbeat waveform sensor, wherein the duty cycle has (i) an active phase during which the heartbeat waveform sensor is on and collects enough data to determine the user's heart rate and (ii) an inactive phase during which the heartbeat waveform sensor is off and does not provide output data
   (d) operating the heartbeat waveform sensor at the duty cycle;
   (e) determining the user's heart rate; and
   (f) presenting the user's heart rate.

15. The wearable fitness monitoring device of claim 14, wherein the heartbeat waveform sensor is a photoplethysmographic sensor comprising (i) a periodic light source, (ii) a photo detector positioned to receive periodic light emitted by the light source after interacting with the user's skin, and (iii) circuitry determining the user's heart rate from output of the photo detector.

16. The wearable fitness monitoring device of claim 15, wherein the photoplethysmographic sensor further comprises a housing having a recess in which the photo detector is disposed.

17. The wearable fitness monitoring device of claim 16, wherein the housing of the photoplethysmographic sensor further comprises a second recess in which the periodic light source is disposed.

18. The wearable fitness monitoring device of claim 17, wherein the housing protrudes at least about 1 mm above a base surface of the wearable fitness monitoring device arranged to press against the user's skin when worn.

19. The wearable fitness monitoring device of claim 15, wherein the photoplethysmographic sensor further comprises an in-mold-labeling (IML) film over the photo detector and the periodic light source.

20. The wearable fitness monitoring device of claim 14, wherein the duty cycle's active phase has a duration of about 5 to 15 seconds for acquiring output data from the heartbeat waveform sensor and determining the user's heart rate, followed by an inactive phase.

21. The wearable fitness monitoring device of claim 20, wherein successive active phases are separated by about 1 to 10 minutes.

22. The wearable fitness monitoring device of claim 20, wherein the control logic further comprises instructions for triggering the active phase by receiving user input requesting a heart rate measurement.

23. The wearable fitness monitoring device of claim 14, wherein the control logic further comprises instructions for collecting output data from the heartbeat waveform sensor and output data from the motion detecting sensor in (a) for about 5-15 seconds during each minute of the duty cycle.

24. The wearable fitness monitoring device of claim 14, further wherein the control logic comprises instructions for:
    detecting that the user is attempting to read a heart rate; and
    temporarily suspending the duty cycling.

25. The wearable fitness monitoring device of claim 14, wherein the control logic comprises instructions for:
    analyzing the output data from the motion detecting sensor to infer a low activity level; and
    temporarily suspending the duty cycling.

26. The wearable fitness monitoring device of claim 14, wherein the motion detecting sensor is an accelerometer or a gyroscope.

27. The wearable fitness monitoring device of claim 14, wherein the instructions for collecting the output data from the heartbeat waveform sensor comprise instructions for:
    pulsing a light source in the wearable biometric monitoring device at a first frequency; and
    detecting light from the light source at the first frequency.

28. The wearable fitness monitoring device of claim 27, wherein the instructions for pulsing the light source at the first frequency comprise instructions for emitting a succession of light pulses of substantially constant intensity.

29. The wearable fitness monitoring device of claim 14, wherein the instructions for presenting the user's heart rate comprise instructions for presenting the heart rate on the wearable biometric monitoring device.

30. The wearable fitness monitoring device of claim 14, wherein the heartbeat waveform sensor is configured to pulse a light source in the biometric monitoring device at a first frequency and detect light from the light source at the first frequency, and wherein during the active phase, pulsing continues and during the inactive phase pulsing stops.

* * * * *